US008093295B2

(12) United States Patent
Wong et al.

(10) Patent No.: US 8,093,295 B2
(45) Date of Patent: Jan. 10, 2012

(54) FORMULATIONS OF SUBEROYLANILIDE HYDROXAMIC ACID AND METHODS FOR PRODUCING THE SAME

(75) Inventors: Jeannie Chow Wong, Jersey City, NJ (US); Benjamin Max Cohen, Cranford, NJ (US); Aaron S. Cote, West Windsor, NJ (US); Erik A. Dienemann, Metuchen, NJ (US); Kimberly Gallagher, Green Lane, PA (US); Craig Ikeda, Harleysville, PA (US); Justin Moser, Collegeville, PA (US); Pavol Rajniak, Lansdale, PA (US); Robert A. Reed, Line Lexington, PA (US); Brian Sell, Royersford, PA (US); Cindy Starbuck, Doylestown, PA (US); Hsien-Hsin Tung, Grayslake, IL (US); Qingxi Wang, Ambler, PA (US); Vincent R. Capodanno, Hillsborough, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 11/663,165

(22) PCT Filed: May 16, 2006

(86) PCT No.: PCT/US2006/018795
§ 371 (c)(1),
(2), (4) Date: Mar. 19, 2007

(87) PCT Pub. No.: WO2006/127321
PCT Pub. Date: Nov. 30, 2006

(65) Prior Publication Data
US 2008/0132575 A1 Jun. 5, 2008

Related U.S. Application Data

(60) Provisional application No. 60/682,875, filed on May 20, 2005, provisional application No. 60/693,128, filed on Jun. 23, 2005.

(51) Int. Cl.
*A61K 31/19* (2006.01)
(52) U.S. Cl. ......... 514/575; 514/613; 514/619; 564/161
(58) Field of Classification Search .................. 514/613, 514/619, 575; 564/161
See application file for complete search history.

(56) References Cited

U.S. PATENT DOCUMENTS

| | | | |
|---|---|---|---|
| 4,690,918 A | 9/1987 | Beppu et al. | |
| 5,055,608 A | 10/1991 | Marks et al. | |
| 5,175,191 A | 12/1992 | Marks et al. | |
| 5,369,108 A | 11/1994 | Breslow et al. | |
| 5,608,108 A | 3/1997 | Marks et al. | |
| 5,654,333 A | 8/1997 | Samid | |
| 5,700,811 A | 12/1997 | Breslow et al. | |
| 5,773,474 A | 6/1998 | Breslow et al. | |
| 5,932,616 A | 8/1999 | Breslow et al. | |
| 6,087,367 A | 7/2000 | Breslow et al. | |
| 6,231,880 B1 | 5/2001 | Perrine et al. | |
| 6,239,176 B1 | 5/2001 | Nudelman et al. | |
| 6,262,116 B1 | 7/2001 | Pandolfi et al. | |
| 6,451,334 B2 | 9/2002 | Perrine | |
| 6,495,719 B2 | 12/2002 | Lan-Hargest et al. | |
| 6,511,990 B1 | 1/2003 | Breslow et al. | |
| RE38,506 E | 4/2004 | Breslow et al. | |
| 6,905,669 B2 | 6/2005 | DiMartino et al. | |
| 7,148,257 B2 | 12/2006 | Bacopoulos et al. | |
| 7,375,137 B2 | 5/2008 | Richon et al. | |
| 7,399,787 B2 | 7/2008 | Chiao et al. | |
| 2003/0082666 A1 | 5/2003 | Kammer et al. | |
| 2003/0114525 A1 | 6/2003 | Kammer et al. | |
| 2003/0161830 A1 | 8/2003 | Jackson et al. | |
| 2003/0235588 A1 | 12/2003 | Richon et al. | |
| 2004/0002506 A1 | 1/2004 | Breslow et al. | |
| 2004/0018968 A1 | 1/2004 | Sgouros et al. | |
| 2004/0072735 A1 | 4/2004 | Richon et al. | |
| 2004/0087631 A1 | 5/2004 | Bacopoulos et al. | |
| 2004/0122101 A1 | 6/2004 | Miller et al. | |
| 2004/0127522 A1 | 7/2004 | Chiao et al. | |
| 2004/0127523 A1 | 7/2004 | Bacopoulos et al. | |
| 2004/0132643 A1 | 7/2004 | Fojo et al. | |
| 2004/0132825 A1 | 7/2004 | Bacopoulos et al. | |
| 2004/0167184 A1 | 8/2004 | Wiech et al. | |
| 2004/0266818 A1 | 12/2004 | Breslow et al. | |
| 2006/0079551 A1 | 4/2006 | Richon et al. | |
| 2006/0167103 A1 | 7/2006 | Bacopoulos et al. | |

(Continued)

FOREIGN PATENT DOCUMENTS

WO WO 95/31977 11/1995
(Continued)

OTHER PUBLICATIONS

Abdou, Remington's Pharmaceutical Sciences, 18th edition, 1990, Chapter 31, Dissolution, pp. 589-602.* U.S. Appl. No. 11/980,994, filed Oct. 30, 2007, Miller, et al.
U.S. Appl. No. 11/981,500, filed Oct. 30, 2007, Miller, et al.
U.S. Appl. No. 12/077,396, filed Mar. 18, 2008, Miller, et al.
U.S. Appl. No. 10/413,422 Office Action mailed on Oct. 12, 2005.
U.S. Appl. No. 0/413,422 Office Action mailed on Jun. 29, 2006.
U.S. Appl. No. 10/413,422 Office Action mailed on Dec. 22, 2006.
U.S. Appl. No. 11/282,420 Office Action mailed on Mar. 5, 2007.
U.S. Appl. No. 11/282,420 Office Action mailed on Nov. 26, 2007.
U.S. Appl. No. 11/592,443 Office Action mailed on Feb. 5, 2008.

(Continued)

*Primary Examiner* — James D Anderson
(74) *Attorney, Agent, or Firm* — Li Su; David A. Muthard

(57) ABSTRACT

The present invention provides a pharmaceutical composition or crystalline composition with a specific dissolution profile, which comprises suberoylanilide hydroxamic acid or a pharmaceutically acceptable salt or hydrate thereof as an active ingredient. The present invention provides a process of producing said crystalline composition or pharmaceutical composition. The present invention also provides compositions with a specific particle size distribution.

68 Claims, 20 Drawing Sheets

U.S. PATENT DOCUMENTS

| | | |
|---|---|---|
| 2006/0276547 A1 | 12/2006 | Bacopoulos et al. |
| 2007/0060614 A1 | 3/2007 | Bacopoulos et al. |
| 2007/0117815 A1 | 5/2007 | Pluda et al. |
| 2007/0197473 A1 | 8/2007 | Frankel et al. |
| 2007/0197568 A1 | 8/2007 | Bunn et al. |
| 2008/0119562 A1 | 5/2008 | Richon et al. |
| 2008/0194692 A1 | 8/2008 | Miller et al. |

FOREIGN PATENT DOCUMENTS

| | | |
|---|---|---|
| WO | WO 98/39965 | 9/1998 |
| WO | WO 98/40080 | 9/1998 |
| WO | WO 98/55449 | 12/1998 |
| WO | WO 00/21979 | 4/2000 |
| WO | WO 00/71703 | 11/2000 |
| WO | WO 01/16106 | 3/2001 |
| WO | WO 01/18171 | 3/2001 |
| WO | WO 01/38322 | 5/2001 |
| WO | WO 01/70675 | 9/2001 |
| WO | WO 02/15921 | 2/2002 |
| WO | WO 02/22577 | 3/2002 |
| WO | WO 02/30879 | 4/2002 |
| WO | WO 02/46144 | 6/2002 |
| WO | WO 02/055017 | 7/2002 |
| WO | WO 02/085400 | 10/2002 |
| WO | WO 03/075839 | 9/2003 |
| WO | WO2005/018578 | 3/2005 |
| WO | WO2007/022408 | 2/2007 |
| WO | WO2007/056135 | 5/2007 |
| WO | WO2007/056162 | 5/2007 |
| WO | WO2007/056232 | 5/2007 |
| WO | WO2007/056244 | 5/2007 |

OTHER PUBLICATIONS

U.S. Appl. No. 11/282,420 Office Action mailed on Apr. 22, 2008.
U.S. Appl. No. 10/413,422 Office Action mailed on Jul. 8, 2008.
U.S. Appl. No. 11/282,420 Office Action mailed on Aug. 20, 2008.
Batch 1136-1136-00-001, of which the dissolution rate profile and particle size distribution is described in Tables 15 and 17 of the instant application, was made according to the methods in Example 1 of US2004/0072735.
"Aton Pharma, Inc. Announces Initiation of Two Phase II Trials to Evaluate Efficacy of HDAC Inhibitor SAHA", Oct. 30, 2002.
"Aton Pharma, Inc. Announces Phase I Clinical Trial of SAHA in Advanced Leukemias", Jul. 1, 2003.
"Aton Pharma, Inc. Appoints Jul. H. Chiao, M.D. as Vice President, Oncology Clinical Research and Development", Sep. 20, 2002.
"Aton Pharma, Inc. Presents Phase I Trial Data of Anti-Cancer Agent SAHA in Patients with Hematological Malignancy at ASCO", Jun. 2, 2003.
"Aton Pharma, Inc. Presents Phase I Trial Data on Anti-Cancer Agent Saha at EORTC/NCI/AACR Symposium", Nov. 21, 2002.
"Aton Pharma, Inc. Received Orphan Drug Designation for SAHA in Multiple Myeloma and Initiates Phase I Trial", Oct. 13, 2003.
"Aton Pharma, Inc. Reports on Phase I Trial of SAHA", Aug. 14, 2002.
Heaney, et al., "Clinical Experience with the Histone Deacetylase (HDAC) Inhibitor Suberoylanilide Hydroxamic Acid (SAHA) in Heavily Pre-Treated Patients with Hematological Malignancies", 2003 ASCO Annual Meeting, Proceedings of the American Society of Clinical Oncology, vol. 22, p. 577, Abstract 2321, 2003.
O'Connor, et al., Journal of the American Society of Hematology 611a, Abstract No. 2562 (2001).
Kelly, et al., Clinical Cancer Research 9, pp. 3578-3588 (2003).
Rubartelli, et al., "High Rates of Thioredoxin Secretion Correlate with Growth Arrest in Hepatoma Cells"; Cancer Research, vol. 55, pp. 675-680, 1995.
Clinicl Trial: An Investigational Study of a Histone Deacetylase (HDAC) Inhibitor Plus Targretin in Cutaneous T-Cell Lymphoma Patients, Aug. 2, 2005.
Clinical Trial: Vorinostat and Bortezomib in Treating Patients with Relapsed or Refractory Multiple Myeloma, Mar. 29, 2006.
Clinical Trial: Vorinostat With or Without Isotretinoin in Treating Young Patients with Recurrent or Refractory Solid Tumors, Lymphoma, or Leukemia, Sep. 20, 2005.
Clinical Trial: Study of Oral Suberoylanilide Hydroxamic Acid (SAHA) in Combination with Bortezomib in Patients with Advanced Multiple Myeloma, May 25, 2005.
Clinical Trial: A Phase I/II Clinical Trial of an Experimental Cancer Drug in Combination with an FDA Approved Cancer Drug for Patients with Relapsed/Refractory Non-Small-Cell Lung Cancer, Nov. 7, 2005.
Clinical Trial: Flavopiridol and Vorinostat in Treating Patients with Relapsed or Refractory Acute Leukemia or Chronic Myelogenous Leukemia or Refractory Anemia, Jan. 16, 2006.
Clinical Trial: Vorinostat in Treating Patients with Acute Myeloid Leukemia, Mar. 21, 2006.
Clinical Trial: Suberoylanilide Hydroxamic Acid (SAHA) Versus Placebo in Advanced Malignant Pleural Mesothelioma, Aug. 5, 2005.
Clinical Trial: Suberoylanilide Hydroxamic Acid, Fluorouracil, Leucovorin, and Oxaliplatin in Treating Patients with Progressive Metastatic or Unresectable Colorectal Cancer or Other Solid Tumors, Aug. 29, 2005.
Clinical Trial: Suberoylanilide Hydroxamic Acid in Advanced Solid Tumors, Mar. 28, 2005.
Clinical Trial: Suberoylanilide Hydroxamic Acid in Treating Patients with Stage IIIB, State IV, or Recurrent Non-Small Cell Lung Cancer, Aug. 29, 2005.
Clinical Trial: Vorinostat and Bevacizumab in Treating Patients with Unresectable or Metastatic Kidney Cancer, May 10, 2006.
Clinical Trial: Vorinostat in Treating Women Who are Undergoing Surgery for Newly Diagnosed Stage I, Stage II, or Stage III Breast Cancer, Dec. 6, 2005.
Clinical Trial: Vorinostat and Gemcitabine in Treating Patients with Metastatic or Unresectable Solid Tumors, Oct. 20, 2005.
Clinical Trial: Vorinostat in Treating Patients with Relapsed or Refractory Indolent Non-Hodgkin's Lymphoma, Nov. 11, 2005.
Clinical Trial: Vorinostat and Bortezomib in Treating Patients with Metastatic or Unresectable Solid Tumors, Sep. 26, 2005.
Clinical Trial: Vorinostat in Treating Patients with Kidney Cancer, Jan. 16, 2006.
Clinical Trial: Vorinostat and Trastuzumab in Treating Patients with Metastatic or Locally Recurrent Breast Cancer, Nov. 22, 2005.
Clinical Trial: Vorinostat in Treating Patients with Progressive or Recurrent Glioblastoma Multiforme, Oct. 12, 2005.
Clinical Trial: Vorinostat and Capecitabine in Treating Patients with Metastatic or Unresectable Solid Tumors, Jul. 19, 2005.
Clinical Trial: Vorinostat in Treating Patients with Metastatic or Unresectable Melanoma, Jul. 19, 2005.
Clinical Trial: Vorinostat and Flavopiridol in Treating Patients with Advanced Solid Tumors, May 10, 2006.
Clinical Trial: Vorinostat and Isotretinoin in Treating Patients with Advanced Kidney Cancer, May 10, 2006.
Clinical Trial: Vorinostat and Temozolomide in Treating Patients with Malignant Gliomas, Dec. 20, 2005.
Clinical Trial: Vorinostat and Decitabine in Treating Patients with Advanced Solid Tumors or Relapsed or Refractory Non-Hodgkin's Lymphoma, Acute Myeloid Leukemia, Acute Lymphocytic Leukemia, or Chronic Myelogenous Leukemia, Jan. 10, 2006.
Garcia-Manero, et al., "Phase I study of oral suberoylanilide hydroxamic acid (SAHA), a histone deacetylase inhibitor, in patients (pts) with advanced leukemias or myelodysplastic syndromes (MDS)", Abstract No. 3027. J. of Clin. One., vol. 22 (14S) 2004 ASCO Annual Meeting Proceedings (2004).
Andrews et al. (2000). Intl. J. Parasitol. 30: 761-768.
Archer et al. (1998). Proc. Natl. Acad. Sci. USA 95: 6791-6796.
Bhalla et al. (2002). "Co-treatment With The Histone Deacetylase Inhibitor Suberoylanilide Hydroxamic Acid (SAHA) Enhances the Cytotoxic Effects of Gleevec and Arsenic Trioxide (AT) Against Bcr-Abl Positive Human Leukemia Cells." American Society of Hematology, 44th Meeting of the American Society of Hematology, Abstract 4611.
Butler et al. (2000). Cancer Res. 60: 5165-5170.
Butler et al. (2001). Clincal Cancer Res. 7: 962-970.
Butler et al. (2002). Proc. Natl. Acad. Sci. USA 99: 11700-11705.
Coffey et al. (2000). Medical and Pediatric Oncology 35: 577-581.
Coffey et al. (2001). Cancer Res. 61: 3591-3594.
Cohen et al. (1999). Anticancer Res. 19: 4999-5006.

Cohen et al. (2002). Anticancer Res. 22: 1497-1504.
Curtin (2002). Exp. Opin. Ther. Patents 12: 1375-1384.
Dressel (2000). Anticancer Res. 20: 1017-1022.
Fei et al. (2002). "Co-treatment With the Histone Deacetylase Inhibitor Suberoylanilide Hydroxamic Acid (SAHA) Enhances Apo-2L/TRAIL-induced Death Inducing Signaling Complex and Apoptosis of Human Acute Lymphoid Leukemia Cells." American Society of Hematology, 44th Meeting of the American Society of Hematology Abstract No. 4602.
Feinman et al. (2002). "The Histone Deacetylase Inhibitor, Suberoylanilide Hydroxamic Acid, Induces Apoptosis of Multiple Myeloma Cells." American Society of Hematology, 44th Meeting of the American Society of Hematology, Abstract No. 3195.
Finnin et al. (1999). Nature 401: 188-193.
Furamai et al. (2001). Proc. Natl. Sci. USA 98: 87-92.
Grunstein (1997). Nature 389: 349-352.
He et al. (2001). J. Clin. Investigation 108: 1321-1330.
Hockly et al. (2003). Proc. Natl. Acad. Sci. USA 100: 2041-2046.
Kelly et al. (2001). "Suberoylanilide Hydroxamic Acid (SAHA), a Histone Deacetylase Inhibitor: Biologic Activity Without Toxicity." American Society of Clinical Oncology, Abstract No. 344.
Kelly et al. (2002). "Histone deacetylase inhibitor, suberoylanilide hydroxamic acid (SAHA), orally administered has good bioavailability and biologic activity." American Society of Clinical Oncology, 38th Annual Meeting of the American Society of Clinical Oncology, Nov. 7-10, 2002, Abstract No. 1831.
Kelly et al. (2002). "A phase I clinical trial of an oral formulation of the histone deacetylase inhibitor suberoylanilide hydroxamic acid (SAHA)." European J. Cancer 38(Suppl. 7): 88, Abstract No. 286.
Kim et al. (1999). Oncogene 18: 2461-2470.
Kohge et al. (1998). Biochem. Pharmacol. 56: 1359-1364.
Komatsu et al. (2001). Cancer Res. 61: 4459-4466.
Kouraklis and Theocharis (2002). Curr. Med. Chem.-Anti-Cancer Agents 2: 477-484.
Lee et al. (2001). Cancer Res. 61: 931-934.
Lin et al. (1998). Nature 391: 811-814.
Mai et al. (2001). OPPI Briefs 33: 391-394.
Marks et al. (2000). J. of the Natl. Cancer Institute 92: 1210-1215.
Marks et al. (2001). Clinical Cancer Res. 7: 759-760.
Marks et al. (2001). Curr. Opin. In Oncology 13: 477-483.
Marks et al. (2001). Nature Reviews 1: 194-202.
Miller et al. (2003). J Med Chem. 46: 5097-5116.
Munster et al. (2001). Cancer Res. 61: 8492-8497.
O'Connor et al. (2002). "Clinical experience of the histone deacetylase inhibitor suberoylanalide hydroxamic acid (SAHA) in heavily pre-treated patients with aggressive non-hodgkin's lymphoma (NHL0 and hodgkin's disease (HD))." American Society of Clinical Oncology, Dec. 6-10, 2002, Abstract No. 4742.
Qui et al. (2000). Mol. Biol. Cell 11: 2069-2083.
Richon et al. (1996). Proc. Natl. Acad. Sci. USA 93: 5705-5708.
Richon et al. (1998). Proc. Natl. Acad. Sci. USA 95: 3003-3007.
Richon et al. (2000). Proc. Natl. Acad. Sci. USA 97: 10014-10019.
Richon and O'Brien (2002). Clinical Cancer Res. 8: 662-664.
Saito et al. (1999). Proc. Natl. Acad. Sci. USA 96: 4592-4597.
Sgouros et al. (2002). "Synergistic Interaction of Suberoylanilide Hydroxamic Acid (SAHA) and Radiation in Human Prostate Tumor Spheroids." American Society of Clinical Oncology, Abstract No. 105.
Stowell et al. (1995). J. Med. Chem. 38: 1411-1413.
Su et al. (2000). Cancer Res. 60: 3137-3142.
Suzuki et al. (1999). J. Med. Chem. 42: 3001-3003.
Van Lint et al. (1996). Gene Expression 5: 245-253.
Webb et al. (1999). J. Biol. Chem. 274: 14280-14287.
Yoshida et al. (1990). J. Biol. Chem. 265: 17174-17179.
Yoshida et al. (1995). BioEssays 17: 423-430.
Zhou et al. (1999). Gene 233: 13-19.
Zhou et al. (2000). Proc. Natl. Acad. Sci. USA 97: 1056-1061.
Zhou et al. (2000). Proc. Natl. Acad. Sci. USA 97: 14329-14333.
Zhou et al. (2001). Proc. Natl. Acad. Sci. USA 98: 10572-10577.
Adams and Elliott (2000). Oncogene 19: 6687-6692.
Bates et al. (1999). Proc. American Society of Clinical Oncology 18: 180a, Abstract No. 693.
Foster et al. (1997). Invest. New Drugs 15: 187-194.
Gojo et al. (2002). Blood 100: Abstract No. 2198.
Gore and Carducci (2000). Exp. Opin. Invest. Drugs 9: 2923-2934.
Huang and Pardee (2000). Molecular Medicine 6: 849-866.
Johnstone, R. (2002). Nature Reviews Drug Discovery 1: 287-299.
Kelly et al. (2002). Exp. Opin. Invest. Drugs 11: 1695-1713.
Kosugi et al. (2001). Jpn. J. Cancer Res. 92: 529-536.
Marshall et al. (2002). J. Exp. Therapeutics and Oncology 2: 325-332.
Piekarz et al. (2001). Blood 98: 2865-2868.
Prakash et al. (2001). Invest. New Drugs 19: 1-11.
Rha et al. (1993). J. Korean Med. Sci. 8:251-256.
Riflcind et al. (2002). 224th ACS National Meeting, Boston, MA, Abstract No. 226.
Sandor et al. (2002). Clincal Cancer Research 8: 718-728.
Secrist et al. (2003). Curr. Opin. Invest. Drugs 4:1422-1427.
Summerhayes, M. (2001). J. Oncol. Pharm. Prac. 7: 107-125.
Vigushin, D. (2002). Current Opin. Invest. Drugs 3: 1396-1402.
Warrell et al. (1998). J. Natl. Cancer Institute 90: 1621-1625.
Wu et al. (2001). "Negative Regulation of bcl-2 Expression by p53 in Hematopoietic Cells." Oncogene 20(2): 240-251, Abstract, Database CAPLUS on STN, Acc. No. DN134:293668.
Adhikari, D et al., Proceedings of the American Association for Cancer Research Annual Meeting, (1998), vol. 39, p. 312, "Radiosensitization of Lymphoma Cell Lines by Sodium Butyrate".
Alexandrov, I et al., FEBS Letters, (1998), vol. 434, pp. 209-214, "Sodium Butyrate Suppresses Apoptosis in Human Burkitt Lymphomas and Murine Plasmacytomas Bearing c-myc Translocations".
Almenara, J et al., Leukemia (2002), vol. 16, pp. 1331-1343, "Synergistic Induction of Mitochondrial Damage and Apoptosis in Human Leukemia Cells by Flavopiridol and the Histone Deacetylase Inhibitor Suberoylanilide Hydroxamic Acid (SAHA)".
Amin HM et al., British Journal of Haematology (2001), vol. 115, pp. 287-297, "Histone Deacetylase Inhibitors Induce Caspase-Dependent Apoptosis and Downregulation of Daxx in Acute Promyelocytic Leukaemia with t(15;17)".
Aron, JL et al., Blood (2003), vol. 102, No. 2, pp. 652-658, "Depsipeptide (FR901228) Induces Histone Acetylation and Inhibition of Histone Deacetylase in Chronic Lymphocytic Leukemia Cells Concurrent With Activation of Caspase 8-mediated Apoptosis and Down-Regulation of c-FLIP Protein".
Benoit, NE et al., Immunopharmacology, (1996), vol. 35, pp. 129-139, "Increased inhibition of Proliferation of Human B Cell Lymphomas Following Litigation of CD40, and Either CD19, CD20, CD95 or Surface Immunoglobulin".
Bode, J et al., Journal of Interferon Research, (1982), vol. 2, No. 2, pp. 159-166, "Links Between Effectsof Butyrate on Histone Hyperacetylation and Regulation of interferon Synthesis in Namalva and FS-4 Cell Lines".
Buckley, AR et al., Cell Growth & Differentiation (1996), vol. 7, pp. 1713-1721, "Alterations in pim-1 and c-myc Expression Associated with Sodium Butyrate-induced Growth Factor Dependency in Autonomous Rat Nb2 Lymphoma Cells".
Buckley, AR et al., Proceedings of the American Association for Cancer Research Annual Meeting,Abstract No. 1294 (1997), vol. 38, p. 193, "Reversal of Apoptosis Resistance by Butyrate in rat Nb2 Lymphoma Cells".
Byrd, JC et al., Blood (1999), vol. 94, No. 4, pp. 1401-1408, "Depsipeptide (FR901228): A Novel Therapeutic Agent with Selective, In Vitro Activity Against Human B-Cell Chronic Lymphocytic Leukemia Cells".
Cao, et al. (2001), Am. J. Respir. Cell Mol. Biol., 25:562-8, "Histone Deacetylase Inhibitor Downregulation of bcl-xl Gene Expression Leads to Apoptotic Cell Death in Mesothelioma".
Carducci, MA et al., Clinical Cancer Research (2001), vol. 7, No. 10, pp. 3047-3055, "A Phase I Clinical and Pharmacological Evaluation of Sodium Phenylbutyrate on an 120-h Infusion Schedule".
Dear, AE et al., Biochimica et Biophysics Acta, (2000), vol. 1492, pp. 15-22, "The Novel Anti-Tumour Agent Oxarnflatin Differentially Regulates Urokinase and Plasminogen Activator Inhibitor Type 2 Expression and Inhibits Urokinase-Mediated Proteolytic Activity".
Desai, D et al., Anticancer Research (2003), vol. 23, pp. 499-504, "Chemopreventive Efficacy of Suberoylanilide Hydroxamic Acid (SAHA) Against 4-(Methylnitrosamino)-1-(3-pyridyl)-1-butanone (NNK)-induced Lung Tumorigenesis in Female A/J Mice".

Dhordain, p. et al., Nucleic Acids Research, (1998), vol. 26, No. 20, pp. 4645-4651, "The LAZ3(BCL-6) Oncoprotein Recruits a SMRT/mSIN3A/Histone Deacetylase Containing Complex to Mediate Transcriptional Repression".

Edelman, MJ et al., Cancer Chemotherapy and Pharmacology (2003), vol. 51, pp. 439-444, "Clinical and Pharmacologic Study of Tributyrin: An Oral Butyrate Prodrug".

Feinman, Ret al., Blood (2002), vol. 100, No. 11, pp. Abstract 3195, "The Histone Deacetylast Inhibitor, Suberoylanilide Hydroxyamic Acid, Induces Apoptosis of Multiple Myeloma Cells".

Fillppovich, I et al., Biochemical and Biophysical Research Communications, (1994), vol. 198, pp. 257-265, "Butyrate Induced Apoptosis in Lymphoid Cells Preceded by Transiet Over-Expression of HSP70 mRNA".

Foss, FM et al., Blood, (1993), vol. 82, No. 10, Suppl. 1, p. 564A, "Biomodulatory Effects of Butyric Acid Derivatives on Leukemia and Lymphoma Cells". Abstract No. 2239.

Gelmetti, V et al., Molecular and Cellular Biology (1998), vol. 18; No. 12, pp. 7185-7191, "Aberrant Recruitment of the Nuclear Receptor Corepressor-Histone Deacetylase Complex by the Acute Myeloid Leukemia Fusion Partner ETO".

Gerbitz, A, Oncogene, (1999), vol. 18, pp. 1745-1753, "Deregulation of the Proto-Oncogene c-myc Through t(8;22) Translocation in Burkitt's Lymphoma".

Gilbert, J et al., Clinical Cancer Research (2001), vol. 7, No. 8, pp. 2292-2300, "A Phase I Dose Escalation and Bioavailability Study of Oral Sodium Phenylbutyrate in Patients with Refractory Solid Tumor Malignancies".

Grisolano, JL et al., Proceedings of the National Academy of Sciences (2003), vol. 100, No. 16, pp. 9506-9511, "An Activated Receptor Tyrosine Kinase, TEL/PDGEbetaR, Cooperates with AML1/ETO to Induce Acute Myeloid Leukemia in Mice".

Harris, NL et al., Blood (1994), vol. 84, No. 5, pp. 1361-1392, "A Revised European-American Classification of Lymphold Neoplasms: A Proposal From the International Lymphoma Study Group".

Jaboin, J et al., Cancer Research (2002), vol. 62, No. 21, pp. 6108-6115, "MS-27-275, an Inhibitor of Histone Deacetylase, Has Marked in Vitro and in Vivo Antitumor Activity against Pediatric Solid Tumors".

Kurita-Ochiai, T et al., Infection and Immunity, (1998), vol. 66, No. 6, pp. 2587-2594, "Volatile Fatty Acid, Metabolic By-Product of Periodontopathic Bacteria, Induces Apoptosis in WEHI 231 and RAJI B Lymphoma Cells and Splenic B Cells".

Liu, Z et al., Journal of Cancer Research and Clinical Oncology, (1998), vol. 124, pp. 541-548, "Synergistic Effect of Epstein-Barr Virus and Tumor Promoters on Induction of Lymphoma and Carcinoma in Nude Mice".

Madisen, L et al., Molecular and Cellular Biology, (1998), vol. 18, No. 11, pp. 6281-6292, "The Immunoglobulin Heavy Chain Locus Control Region Increases Histone Acetylation along Linked c-myc Genes".

Niitsu, N et al., Molecular Pharmacology, (2000), vol. 58, pp. 27-36, "Anticancer Derivative of Butyric Acid (Pivalyloxymethyl Butyrate) Specifically Potentiates the Cytotoxicity of Doxorubicin and Daunorubicin Through the Suppression of Microsomal Glycosidic Activity".

Orr, D et al., 2000 ASCO Annual Meeting, Abstract No. 763, "Phase I Pharmacokinetic (PK) Study of CI-994 in Combination with Gemcitabine (GEM) in Patients with Advanced Solid Tumors".

Polack, A et al., The EMBO Journal, (1993), vol. 12, No. 10, pp. 3913-3920, "Regulatory Elements in the Immunoglobulin Kappa Locus Induce c-myc Activation and the Promoter Shift in Burkitt's Lymphoma Cells".

Rezuke, WN et al., Clinical Chemistry (1997), vol. 43, No. 10, pp. 1814-1823, "Molecular Diagnosis of B- and T-cell Lymphomas: Fundamental Principles and Clinical Applications".

Rottleb, C et al., International Journal of Cancer, (1995), vol. 62, pp. 697-702, "Among 17 Inducers of Differentiation Only Sodium Butyrate Causes a Permanent Down-Regulation of c-myc in Burkitt's Lymphoma".

Rottleb, C et al., International Journal of Cancer, (1996), vol. 67, pp. 724-729, "Structure-Activity Relationship of 17 Structural Analogues of N-Butyric Acid Upon c-myc Expression".

Rubio, MA et al., Blood, (1995), vol. 86, No. 10, pp. 3715-3724, "Granulocyte-Macrophase Colony-Stimulating Factor, Phorbol Ester, and Sodium Butyrate Induce the CD11c Integrin Gene Promoter Activity During Myeloid Cell Differentiation".

Schrump, DS et al., Clinical Lung Cancer (2002), vol. 4, No. 3, pp. 186-192, "Phase I Study of Sequential Deoxyazacytidine/depsipeptide Infusion in Patients with Malignancies Involving Lungs or Pleura".

Vrana JA et al., Oncogene (1999), vol. 18, pp. 7016-7025, "Induction of Apoptosis in U937 Human Leukemia Cells by Suberoylanilide Hydroxamic Acid (SAHA) Proceeds Through Pathways That are Regulated by Bcl-2/Bcl-XL, c-Jun, and p21CIP1, but independent of p53".

Waheed et al. (2000), Proceedings of the American Association for Cancer Research Meeting, (91st, San Francisco, 41:808, Abstract 5135, "The Histone Deacetylase Inhibitor FR 901228 Induces SV40T/T Antigen Expression and P53 Hyperacetylation in Human Pleural Mesothelioma Cells".

Watanabe, M et al., Cancer Research (1990), vol. 50, pp. 3245-3248, "Effect of liposomes containing sodium butyrate conjugated with anti-CD19 monoclonal antibody on in vitro and in vivo growth of malignant lymphoma".

Weiser et al. (2001), J. Immunotherapy, 24:151-61, "Sequencial 5-Aza-2'deoxyctidine-Depsipeptide FR901228 Treatment Induces Apoptosis Preferentially in Cancer Cells and Facilitates Their Recognition by Cytolytic T Lymphocytes Specific for NY-ESO-1".

Yu, C et al., Cancer Research (2001), vol. 63, pp. 2118-2126, "Histone Deacetylase Inhibitors Promote STI571-Mediated Apoptosis in STI571-Sensitive and -Resistant Bcr/Abl+ Human Myeloid Leukemia Cells".

Zhang, M et al., Cell Stress & Chaperones, (1998), vol. 3, No. 1, pp. 57-66, "Heat-Induced Proteolysis of HSF Causes Premature Deactivation of the Heat Shock Response in Nb2 Lymphoma Cells".

Bruner, RJ et al., Blood (2002), 44th Annual Meeting of the American Society of Hematology, vol. 100, No. 11, pp. Abstract No. 1492, "Phase I trial of the histone deacetylase inhibitor depsipeptide (FR901228) in fludarabine refractory chronic lymphocytic leukemia".

Guo, F et al., American Society of Hematology, (Dec. 6-10, 2002), p. 268b, Abstract 4602 "Co-treatment with the histone deacetylase inhibitor suberoylanilide hydroxamic acid (SAHA) enhances Apo-2L/TRAIL-induced death inducing signaling complex and apoptosis of human acute lymphoid leukemia cells".

Marcucci, G et al., Blood, (2002), 44th Annual Meeting of the American Society of Hematology, vol. 100, No. 11, pp. Abstract No. 317, "Phase I trial of the histone deacetylase inhibitor depsipeptide (FR901228) in acute myeloid leukemia (AML)".

Nimmanapalli, R et al., American Society of Hematology, (Dec. 6-10, 2002), 14 pages, "Co-treatment with the histone deacetylase inhibitor suberoylanilide hydroxamic acid (SAHA) enhances Gleevec-induced apoptosis of Bcr-Abl positive human acute leukemia cells".

Nimmanapalli, R et al., Blood (2003), vol. 101, No. 8, pp. 3236-3239, "Cotreatment with the histone deacetylase inhibitor suberoylanilide hydroxamic acid (SAHA) enhances imatinib-induced apoptosis of Bcr-Abl-positive human acute leukemia cells".

Tabe, Y et al., Blood (2002), 44th Annual Meeting of the American Society of Hematology, vol. 100, No. 11, pp. Abstract No. 3028, "Effects of histone deacetylase inhibitor suberoylanikide hydroxamic acid (SAHA) and DNA methylation inhibitor 5-aza-2'-deoxycytidine (DAC) on the transcriptional activation of RARbeta and p21WAF in acute promyelocytic leukemia cells".

Zhang, C et al, The Journal of Investigative Dermatology (2003), vol. 121, No. 1, pp. Abstract 1189, "The histone inhibitor suberoylanilide hydroxamic acid induces apoptosis in cutaneous T cell lymphoma cells".

O'Connor, et al., "Clinical Experience with Intravenous and Oral Formulations of the Novel Histone Deacetylase Inhibitor Suberoylanilide Hydroxamic Acid in Patients with Advanced Hematologic Malignancies", J. of Clin. Onc., vol. 24, No. 1, Jan. 1, 2006, pp. 166-173.
Kelly, et al., "Phase I Study of an Oral Histone Deacetylase Inhibitor, Suberoylanilide Hydroxamic Acid, in Patients with Advanced Cancer", J. of Clin. One., vol. 23, No. 17, Jun. 10, 2005, pp. 3923-3931.
Zolinza Label.
Parker, et al., AIChE J. pp. 1290-1299 (2000).
Nunez, et al., Chem. Eng. Sci., pp. 2075-2083 (1986).
Levenspiel, O., Chemical Reaction Enginering, 2nd edition, p. 373 (1972).
Vanni, M., Journal of Colloid and Interface Science, pp. 143-160 (2000).
Hill, P.J., et al., AIChE J., pp. 1204-1216 (1995).
Rubin, et al., AACR Meeting Abstracts, Apr. 2006, 683, Proc Amer Assoc Cancer Res, vol. 47, Abstract #2907 (2006).
Richardson, et al., "A Phase 2 Study of Bortezomib in Relapsed, Refractory Myeloma", The New England Journal of Medicine, vol. 348, Issue 26, pp. 2609-2617, Jun. 26, 2003.
50 mg SAHA capsules from a lot were used in: "A phase I study of oral SAHA in patients with advanced solid tumors and hematological malignancies starting Sep. 2002." A Phase II study of oral SAHA in patients with cutaneous T-cell lymphoma and peripheral T-cell lymphomas unresponsive to conventional treatment starting Oct. 2002. ; "A Phase II study of orall SAHA in patients with recurrent and/or metastatic head and neck cancer starting oct. 2002"; "A Phase I study of oral SAHA in patients with advanced leukemia starting May 2003."
50 mg SAHA capsules from a lot were used in: "A phase I study of oral SAHA in patients with advanced solid tumors and hematological malignancies starting Jun. 2003."; "A Phase II study of oral SAHA in patients with cutaneous T-cell lymphoma and peripheral T-cell lymphomas unresponsive to conventional treatment starting Oct. 2003."; "A Phase I study of oral SAHA in patients with advanced leukemia starting Sep. 2003."; "A Phase I Study of oral SAHA in patients with advanced multiple myeloma starting Dec. 2003."; The in vitro dissolution profile of 100 mg of SAHA taken from combining the contents of two 50 mg SAHA capsules was f2—49.9. 37.1% dissolved at 10 minutes, 54.8% dissolved at 15 minutes, 67.3% dissolved at 20 minutes, 82.9% dissolved at 30 minutes, 93.8% dissolved at 45 minutes, 98.2% dissolved at 60 minutes.
200 mg SAHA capsules from a lot were used in a phase I study of oral SAHA in patients with advanced solid tumors and hematological malignancies starting Aug. 2001. The in vitro dissolution profile of 100 mg of SAHA taken from half of the contents of a 200 mg capsule was t2—50.3, 62.4% dissolved at 10 minutes, 71.4% dissolved at 15 minutes, 77.8% dissolved at 20 minutes, 86.0% dissolved at 30 minutes, 92.8% dissolved at 45 minutes, 95.6% dissolved at 60 minutes.
200 mg SAHA capsules from a lot were used in: "A phase I study of oral SAHA in patients with advanced solid tumors and hematological malignancies starting Dec. 2003."; "A Phase I study of oral SAHA in patients with advanced leukemia starting Apr. 2004."; "A Phase IIb study of oral SAHA in patients with advanced T-cell lymphoma starting Mar. 2004." The in vitro dissolution profile of 100 mg of SAHA taken from half of the contents of a 200 mg capsule was f2—54.7, 58.1% dissolved at 10 minutes, 68.6% dissolved at 15 minutes, 75.9% dissolved at 20 minutes, 84.9% dissolved at 30 minutes, 91.9% dissolved at 45 minutes, 95.0% dissolved at 60 minutes.
200 mg SAHA capsules from a lot were used in: "A phase I study of oral SAHA in patients with advanced solid tumors and hematological malignancies starting Nov. 2002."; "A Phase II study of oral SAHA in patients with cutaneous T-cell lymphoma and peripheral T-cell lymphomas unresponsive conventional treatment starting Oct. 2002."; "A Phase II study of oral SAHA in patients with recurrent and/or metastatic head and neck cancer starting Oct. 2002."; "A Phase I study of oral SAHA in patients with advanced leukemia starting Aug. 2003."; "A Phase I study of oral SAHA in patients with advanced multiple myeloma starting Sep. 2003."; "The in vitro dissolution profile of 100 mg of SAHA taken from half of the contents of a 200 mg capsule was f2—69.1, 47.8% dissolved at 10 minutes, 59.4% dissolved at 15 minutes, 68.1% dissolved at 20 minutes, 78.6% dissolved at 30 minutes, 87.6% dissolved at 45 minutes, 92.8% dissolved at 60 minutes."
100 mg SAHA capsules from a lot were used in: "A Phase IIb study of oral SAHA in Advanced T-cell Lymphoma starting Nov. 2004."; The in vitro dissolution profile of 100 mg of SAHA taken from the contents of a 100 mg capsule was f2—100, 52.7% dissolved at 10 minutes, 61.7% dissolved at 15 minutes, 67.7% dissolved at 20 minutes, 75.5% dissolved at 30 minutes, 82.6% dissolved at 45 minutes, 87.0% dissolved at 60 minutes.
EPO Correspondence dated Mar. 22, 2010 of EP Application 06759843.3. (23 pages).
Committee for proprietary medicinal products, A: Oral Dosage Forms, B: Transdermal dosage forms, Section I Quality, 1999, The European Agency for the evaluation of medicinal products, London, UK, XP002585113, pp. 1-15.
Nishimura, Kenji, "Design and Evaluation of Oral Administration Drugs", Jiho, (1995), pp. 81-85, 168-172, 251-259.

* cited by examiner

US 8,093,295 B2

FORMULATIONS OF SUBEROYLANILIDE HYDROXAMIC ACID AND METHODS FOR PRODUCING THE SAME

PRIORITY CLAIM

This application is a §371 National Stage Application of PCT/US2006/018795, filed on May 16, 2006, which claims priority from U.S. Provisional Application Ser. Nos. 60/682,875 filed on May 20, 2005 and 60/693,128 filed on Jun. 23, 2005.

FIELD OF THE INVENTION

The present invention provides a pharmaceutical composition or crystalline composition with a specific dissolution profile, which comprises suberoylanilide hydroxamic acid or a pharmaceutically acceptable salt or hydrate thereof as an active ingredient. The present invention provides a process of producing said crystalline composition or pharmaceutical composition. The present invention also provides compositions with a specific particle size distribution.

BACKGROUND OF THE INVENTION

Throughout this application various publications are referenced by arabic numerals within parentheses. Full citations for these publications may be found at the end of the specification immediately preceding the claims.

Cancer is a disorder in which a population of cells has become, in varying degrees, unresponsive to the control mechanisms that normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations.

Cancer therapy is also being attempted by the induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

Despite many advances in the field of oncology, the majority of solid tumors remain incurable in the advanced stages. Cytotoxic therapy is used in most cases, however, it often causes significant morbidity to the patient without significant clinical benefit. Less toxic and more specific agents to treat and control advanced malignancies are being explored.

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5, 7-9), derivatives of vitamin D and retinoic acid (10-12), steroid hormones (13), growth factors (6,14), proteases (15,16), tumor promoters (17,18), and inhibitors of DNA or RNA synthesis (4, 19-24), can induce various transformed cell lines and primary human tumor explants to express more differentiated characteristics.

Histone deacetylase inhibitors such as suberoylanilide hydroxamide acid (SAHA), belong to this class of agents that have the ability to induce tumor cell growth arrest, differentiation and/or apoptosis (25). These compounds are targeted towards mechanisms inherent to the ability of a neoplastic cell to become malignant, as they do not appear to have toxicity in doses effective for inhibition of tumor growth in animals (26). There are several lines of evidence that histone acetylation and deacetylation are mechanisms by which transcriptional regulation in a cell is achieved (27). These effects are thought to occur through changes in the structure of chromatin by altering the affinity of histone proteins for coiled DNA in the nucleosome. There are five types of histones that have been identified in nucleosomes (designated H1, H2A, H2B, H3 and H4). Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery. The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

SAHA (ZOLINZA™ (vorinostat)) has been shown to be useful for treating cancer, selectively inducing terminal differentiation of neoplastic cells, inducing cell growth arrest and/or inducing apoptosis. The inhibition of HDAC by SAHA is thought occur through direct interaction with the catalytic site of the enzyme as demonstrated by X-ray crystallography studies (28). The result of HDAC inhibition is not believed to have a generalized effect on the genome, but rather, only affects a small subset of the genome (29). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (30). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (31).

SUMMARY OF THE INVENTION

The present invention provides a pharmaceutical composition with a specific dissolution profile, which comprises suberoylanilide hydroxamic acid or a pharmaceutically acceptable salt or hydrate thereof as an active ingredient. In one embodiment, the active ingredient of the pharmaceutical composition has an in vitro dissolution profile with a similarity factor (f2) of at least 50 to 100 compared to the reference dissolution profile shown in FIG. 1. The invention also provides pharmaceutical compositions for oral administration, and unit dosage forms based thereon.

The present invention also provides a crystalline composition comprising suberoylanilide hydroxamic acid or a pharmaceutically acceptable salt or hydrate thereof as an active ingredient, wherein about 100 mg of the active ingredient has an in vitro dissolution profile with a similarity factor (f2) of at least 50 to 100 compared to the reference dissolution profile shown in FIG. 2.

The present invention also provides methods of producing the pharmaceutical compositions. The invention also provides compositions with specific particle size distributions.

BRIEF DESCRIPTION OF THE DRAWINGS

FIG. 7 shows x-ray diffractograms for SAHA.

DETAILED DESCRIPTION OF THE INVENTION

Figure 1:
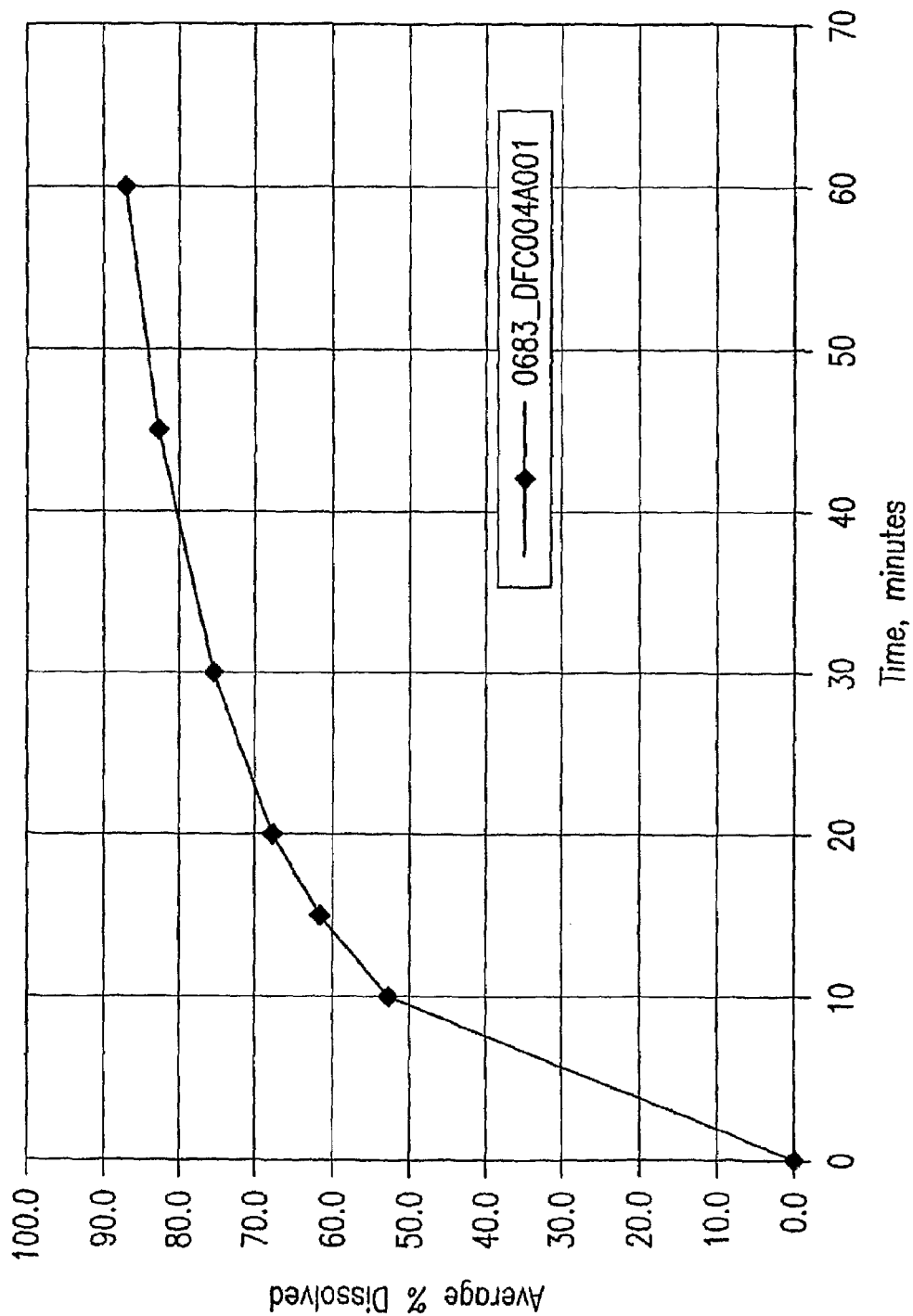
FIG. 1 shows the dissolution profile of SARA from the reference capsule lot 0683_004A001. The capsules contain about 100 mg of active ingredient SAHA, and excipients.

The term "pharmaceutically acceptable carrier" is intended to include any and all solvents, dispersion media, coatings, antibacterial and antifungal agents, isotonic and absorption delaying agents, and the like, compatible with pharmaceutical administration, which would maintain the specified dissolution rate of the active ingredient in the pharmaceutical composition. Suitable carriers are described in the most recent edition of Remington's Pharmaceutical Sciences, a standard reference text in the field, which is incorporated herein by reference. Liposomes and non-aqueous vehicles such as fixed oils may also be used. The use of such media and agents for pharmaceutically active substances is well known in the art. Except insofar as any conventional media or agent is incompatible with the active ingredient, use thereof in the compositions is contemplated. Supplementary active compounds can also be incorporated into the compositions.

The term "f2" or "F2" refers to a similarity factor determined through a point by point comparison of a new in vitro dissolution profile to a reference in vitro dissolution profile, as shown in equation 1.

$$f_2 = 50 \log \left\{ \left[ 1 + 1/n \sum_{t=1}^{n} (R_t - T_t)^2 \right]^{-0.5} \times 100 \right\}$$ (Equation 1)

$R_t$ refers to the percent of compound dissolved at each time point (t) for the reference. $T_t$ refers to the percent of compound dissolved at each time point (t) for the test sample. n refers to the number of time points used for the calculation. $f_2$ values of 50 or greater are considered to reflect similar in vitro dissolution rates.

For the purpose of this invention, dissolution rates or profiles in vitro of the entire active ingredient of the pharmaceutical composition is measured from the entire pharmaceutical composition according to the steps and conditions in Example 14. In one embodiment, dissolution rates or profiles in vitro is measured by using a USP Dissolution Apparatus II with a helical sinker (Quality Lab Accessories L.L.C., Manville, N.J.) in 900 mL of 2.0% Tween (TCI America, Portland, Oreg.) at a temperature of 37±0.5° C., and paddles rotated at 100 rpm. The entire pharmaceutical composition includes the entire active ingredient and if the pharmaceutical composition contains a capsule shell, carrier, excipient, diluent, disintegrating agent, lubricant, binder or any additional agent described in the Pharmaceutical Composition Section below, the measurement is performed with those components.

For the purpose of this invention, dissolution rates or profiles in vitro of "a portion of the single oral dosage unit form comprising about 100 mg of the active ingredient" is measured by retrieving a composition comprising about 100 mg of the active ingredient from the single oral dosage unit form, and using a USP Dissolution Apparatus II with a helical sinker (Quality Lab Accessories L.L.C., Manville, N.J.) in 900 mL of 2.0% Tween (TCI America, Portland, Oreg.) at a temperature of 37±0.5° C., and paddles rotated at 100 rpm. If the single oral dosage unit form contains a capsule shell, carrier, excipient, diluent, disintegrating agent, lubricant, binder or any additional agent described in the Pharmaceutical Composition Section below, the measurement is performed with those components.

Dissolution rates or profiles in vitro of "about 100 mg of the active ingredient of the pharmaceutical composition" is measured according to the steps and conditions in Example 15. In one embodiment, it is measured by using a USP Dissolution Apparatus II with a helical sinker (Quality Lab Accessories L.L.C., Manville, N.J.) in 900 mL of 2.0% Tween (TCI America, Portland, Oreg.) at a temperature of 37±0.5° C., and paddles rotated at 100 rpm.

For the purpose of this invention, particle size distribution (% volume at each particle size) is measured via a Sympatec laser diffraction analyzer (HELOS H1006, Clausthal-Zellerfeld, Germany) equipped with a RODOS powder dispersion system. The sample is atomized through a laser beam using 0.1 bar air pressure, and particle size distribution is collected using a focal length lens of 850 or 1750-μm with targeted obscuration range of 5-20%. A fraunhofer optical model is utilized to deconvolute the sample scattering patterns to yield the resultant particle size distributions.

For the purpose of this invention, % volume of active ingredient is measured by retrieving the particle content (i.e., active ingredient and the excipients) from the pharmaceutical composition, measuring the particle size distribution (% volume of each particle size) of the particle content, subtracting the particle size distribution of particles that are not active ingredient, and normalizing % volume of active ingredient. The % volume of active ingredient is normalized by multiplying the % volume by 100%/percentage of active ingredient relative to particle content.

The term "about" when used in the context of an amount refers to ±10% of the specified amount.

For the purpose of this invention, for X-ray diffraction patterns, depending on the calibration, sample or instrumentation, peaks at 2θ can shift up to ±0.3 degrees (error). In one embodiment, all peaks in X-ray diffraction pattern shift up to +0.3 degrees, or up to −0.3 degrees. An X-ray diffraction pattern or peaks within that error is considered the same or substantially similar.

Compositions with Specific Dissolution Rate

The present invention provides a pharmaceutical composition comprising suberoylanilide hydroxamic acid or a pharmaceutically acceptable salt or hydrate thereof as an active ingredient, wherein the entire active ingredient of the pharmaceutical composition is 43-63% dissolved at 10 minutes, 66-86% dissolved at 30 minutes, and 77-97% dissolved at 60 minutes in vitro. In one embodiment, the entire active ingredient of the pharmaceutical composition is 52-72% dissolved at 15 minutes, 66-86% dissolved at 30 minutes, and 73-93% dissolved at 45 minutes in vitro. In another embodiment, the entire active ingredient of the pharmaceutical composition is 43-63% dissolved at 10 minutes, 52-72% dissolved at 15 minutes, 58-78% dissolved at 20 minutes, 66-86% dissolved at 30 minutes, 73-93% dissolved at 45 minutes and 77-97% dissolved at 60 minutes in vitro. In one embodiment, the entire active ingredient of the pharmaceutical composition is 46-60% dissolved at 10 minutes, 55-69% dissolved at 15 minutes, 61-75% dissolved at 20 minutes, 69-83% dissolved at 30 minutes, 76-90% dissolved at 45 minutes, and 80-94% dissolved at 60 minutes in vitro. In one embodiment, at least 45% but less than or equal to 75% of the entire active ingredient is dissolved at 15 minutes, at least 75% of the entire active ingredient is dissolved in 60 minutes.

In another embodiment, the invention provides a pharmaceutical composition comprising suberoylanilide hydroxamic acid or a pharmaceutically acceptable salt or hydrate thereof as an active ingredient, wherein the entire active ingredient of the pharmaceutical composition has an in vitro dissolution profile with a similarity factor (f2) of at least 50 to 100 compared to the reference dissolution profile shown in FIG. 1. In one embodiment, f2 is 56 to 100. In one embodiment, f2 is 60 to 100. In one embodiment, f2 is 65 to 100. In another embodiment, f2 is 80 to 100.

In one embodiment, the active ingredient is crystalline. In another embodiment, the active ingredient is crystalline suberoylanilide hydroxamic acid. In a particular embodiment, the crystalline suberoylanilide hydroxamic acid is SAHA Form I and characterized by an X-ray diffraction pattern substantially similar to that set forth in FIG. 7A. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0 degrees 2θ.

In one embodiment, SAHA Form I is characterized by an X-ray diffraction pattern including characteristic peaks at about 9.0, 9.4, 17.5, 19.4, 20.0, 24.0, 24.4, 24.8, 25.0, 28.0, and 43.3 degrees 2θ. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0, 43.3 degrees 2θ and lacking a peak at 13.4-14.0 and 22.7-23.0 degrees 2θ. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0 degrees 2θ and lacking a peak at 13.4-14.0 and 22.7-23.0 degrees 2θ. In one embodiment, SAHA Form I is additionally characterized by the lack of at least one peak at about <8.7, 10.0-10.2, 13.4-14.0, 15.0-15.2, 17.5-19.0, 20.1-20.3, 21.1-21.3, 22.0.-22.22, 22.7-23.0, 25.0-25.5, 26.0-26.2, and 27.4-27.6 degrees 2θ. In another embodiment, SAHA Form I is further characterized by a Differential Scanning Calorimetry (DSC) thermogram having a single maximum value at about 164.4±2.0, as measured by a Perkins Elmer DSC 6 Instrument. 5. In one embodiment, the crystalline suberoylanilide hydroxamic acid has unit cell parameters of a=10.9 Å, b=7.9 Å, c=16.4 Å, α=90°, β=97.8°, γ=90°, space group $P2_1/n$.

In a particular embodiment, the crystalline suberoylanilide hydroxamic acid is SAHA Form IV and is characterized by an X-ray diffraction pattern including characteristic peaks at about 8.8, 9.3, 11.0, 12.4, 17.4, 19.4, 19.9, 22.4, 22.9, 23.83, 24.2, 24.8, 25.8, 27.0, 27.8, 28.4 degrees 2θ.

In one embodiment, the invention provides a single capsule comprising about 100 mg suberoylanilide hydroxamic acid or a pharmaceutically acceptable salt or hydrate thereof as an active ingredient, wherein the entire active ingredient has an in vitro dissolution profile characterized by: at least 45% but less than or equal to 75% of the entire active ingredient is dissolved at 15 minutes, at least 75% of the entire active ingredient is dissolved in 60 minutes, wherein the active ingredient is crystalline suberoylanilide hydroxamic acid and characterized by an X-ray diffraction pattern including characteristic peaks at 9.0, 9.4, 17.5, 19.4, 20.0, 24.0, 24.4, 24.8, 25.0, 28.0 degrees θ, and lacking a peak at 13.4-14.0 and 22.7-23.0 degrees 2θ.

In another embodiment, the invention provides a single capsule comprising about 100 mg suberoylanilide hydroxamic acid or a pharmaceutically acceptable salt or hydrate thereof as an active ingredient, wherein the entire active ingredient has an in vitro dissolution profile with a similarity factor (f2) of at least 50 to 100 compared to the reference dissolution profile shown in FIG. 1, wherein the active ingredient is crystalline suberoylanilide hydroxamic acid and characterized by an X-ray diffraction pattern including characteristic peaks at 9.0, 9.4, 17.5, 19.4, 20.0, 24.0, 24.4, 24.8, 25.0, 28.0 degrees 2θ, and lacking a peak at 13.4-14.0 and 22.7-23.0 degrees 2θ.

In a further embodiment, the invention provides a single capsule comprising about 100 mg suberoylanilide hydroxamic acid or a pharmaceutically acceptable salt or hydrate thereof as an active ingredient, wherein the entire active ingredient has an in vitro dissolution profile characterized by 43-63% dissolved at 10 minutes, 66-86% dissolved at 30 minutes, and 77-97% dissolved at 60 minutes, wherein the active ingredient is crystalline suberoylanilide hydroxamic acid and characterized by an X-ray diffraction pattern including characteristic peaks at 9.0, 9.4, 17.5, 19.4, 20.0, 24.0, 24.4, 24.8, 25.0, 28.0 degrees 2θ, and lacking a peak at 13.4-14.0 and 22.7-23.0 degrees 2θ.

The invention also provides a single oral dosage unit form comprising about 120 mg to about 600 mg of suberoylanilide hydroxamic acid or a pharmaceutically acceptable salt or hydrate thereof as an active ingredient, wherein a portion of said dosage unit form comprising about 100 mg of the active ingredient has an in vitro dissolution profile with a similarity factor (f2) of at least 50 to 100 compared to the reference dissolution profile shown in FIG. 1. In one embodiment, the in vitro dissolution profile has a similarity factor (f2) of at least 70 to 100 compared to the reference dissolution profile shown in FIG. 1. In one embodiment, the active ingredient is crystalline suberoylanilide hydroxamic acid and characterized by an X-ray diffraction pattern including characteristic peaks at 9.0, 9.4, 17.5, 19.4, 20.0, 24.0, 24.4, 24.8, 25.0, 28.0 degrees 2θ, and lacking a peak at 13.4-14.0 and 22.7-23.0 degrees 2θ.

Figure 2:
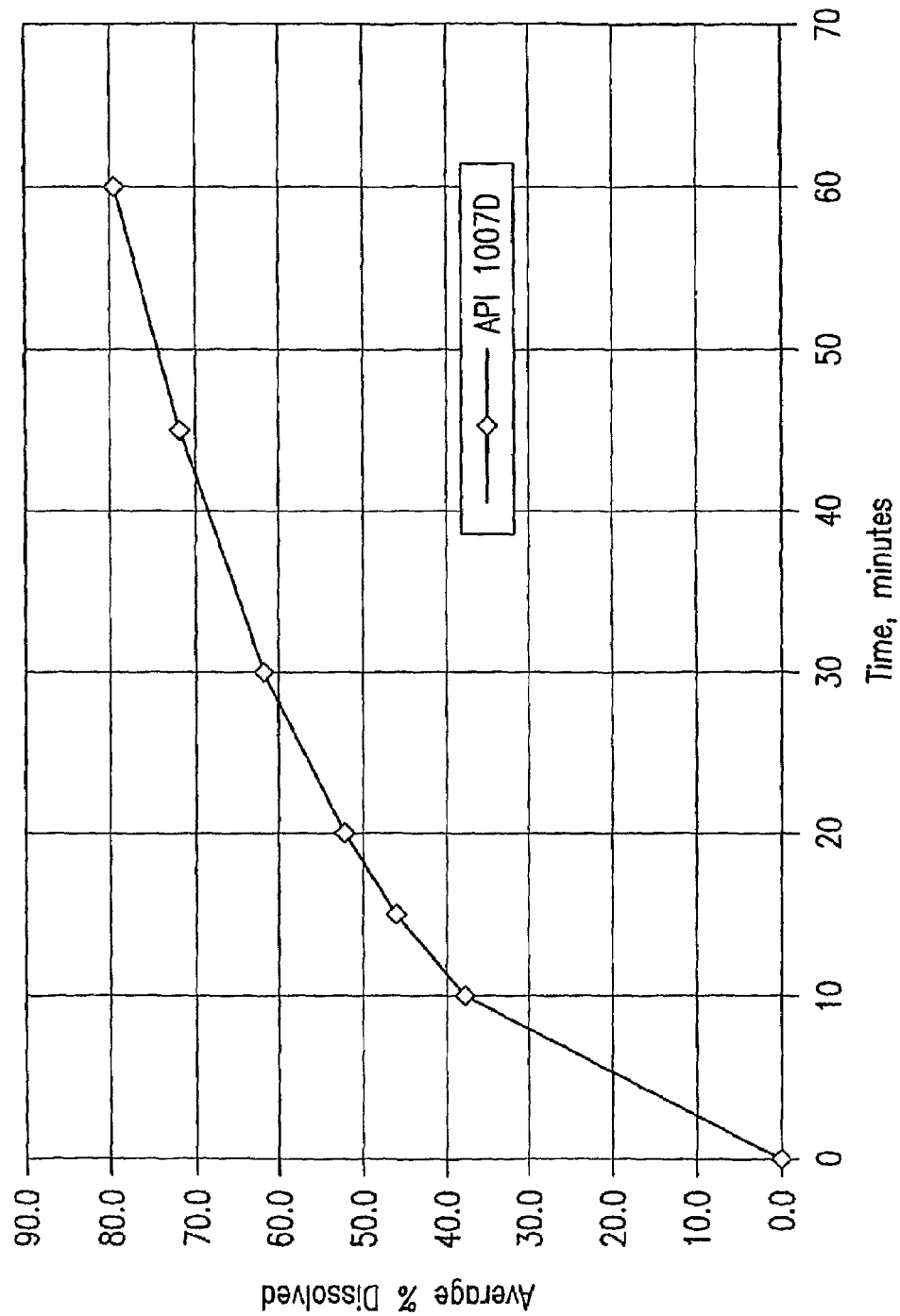
FIG. 2 shows the dissolution profile of the reference SAHA API batch 1007D (blended SAHA crystals) prior to encapsulation. The dissolution profile was measured based on about 100 mg of SAHA.

The present invention also provides a crystalline composition comprising suberoylanilide hydroxamic acid or a pharmaceutically acceptable salt or hydrate thereof as an active ingredient, wherein about 100 mg of the active ingredient has an in vitro dissolution profile with a similarity factor (f2) of at least 50 to 100 compared to the reference dissolution profile shown in FIG. 2. This crystalline composition is a precursor to the pharmaceutical composition. In the instance where the pharmaceutical composition is in the form of a capsule, the crystalline composition is the active ingredient with or without excipients before encapsulation. In one embodiment, the active ingredient is crystalline suberoylanilide hydroxamic acid and characterized by an X-ray diffraction pattern including characteristic peaks at 9.0, 9.4, 17.5, 19.4, 20.0, 24.0, 24.4, 24.8, 25.0, 28.0 degrees 2θ, and lacking a peak at 13.4-14.0 and 22.7-23.0 degrees 2θ.

The active ingredient can be in any crystalline form provided that the active ingredient particles exhibit the specified dissolution rate. The active ingredient can also be in amorphous form. The active ingredient particles may be micronized, or may be agglomerated, particulate granules, powders, oils, oily suspensions or any other form of solid.

In a particular embodiment of the above compositions, the active ingredient is suberoylanilide hydroxamic acid.

The invention also encompasses pharmaceutical compositions comprising pharmaceutically acceptable salts of the SAHA with inorganic bases, for example, sodium, potassium, ammonium, calcium, or ferric hydroxides, and such organic bases as isopropylamine, trimethylamine, 2-ethylamino ethanol, histidine, procaine, and the like.

The invention also encompasses pharmaceutical compositions comprising hydrates of SAHA. The term "hydrate" includes but is not limited to hemihydrate, monohydrate, dihydrate, trihydrate and the like.

Compositions with Specific Particle Size Distribution

The invention also provides a pharmaceutical composition comprising suberoylanilide hydroxamic acid or a pharmaceutically acceptable salt or hydrate thereof as an active ingredient, wherein the % volume for particle sizes from about 90 to 110 microns to about 120 to 250 microns increases, peaks at about 120 to 250 microns, and decreases after the peak. In one embodiment, the peak is the highest % volume compared to % volume of other particle sizes.

In one embodiment, the % volume of active ingredient with particle size at about 90 to 110 microns is in the range of about 2.0% to about 10%, and the % volume of active ingredient with particle size at about 120 to 250 microns is in the range of about 4.0% to about 12%. In one embodiment, the % volume of active ingredient with particle size at about 90 to 110 microns is in the range of about 3.0% to about 9%, and the % volume of active ingredient with particle size at about 120 to 250 microns is in the range of about 5.0% to about 11.5%.

In another embodiment, the % volume of particles with particle size at about 90 to 110 microns is in the range of about 5.5% to about 8.0%, and the % volume of particles with particle size at about 120 to 250 microns is in the range of about 6.5% to about 9.0%. In one embodiment, the % volume of particles with particle size at about 90 to 110 microns is in the range of about 6.0% to about 7.5%, and the % volume of particles with particle size at about 120 to 250 microns is in the range of about 7.0% to about 8.5%.

In one embodiment, the % volume of active ingredient with particle size less than about 105 microns is about 45-85% and the % volume of active ingredient with particle size more than about 105 microns is about 55-15%.

In one embodiment, the % volume of active ingredient for particle sizes from about 20 to 25 microns to about 35 to 40 microns increases, peaks at about 35 to 40 microns, and decreases after the peak. In one embodiment, the % volume of active ingredient with particle size at about 20 to 25 microns is in the range of about 1.0% to about 4%, and the % volume of active ingredient with particle size at about 35 to 40 microns is in the range of about 3.0% to about 7%.

Figure 7A:
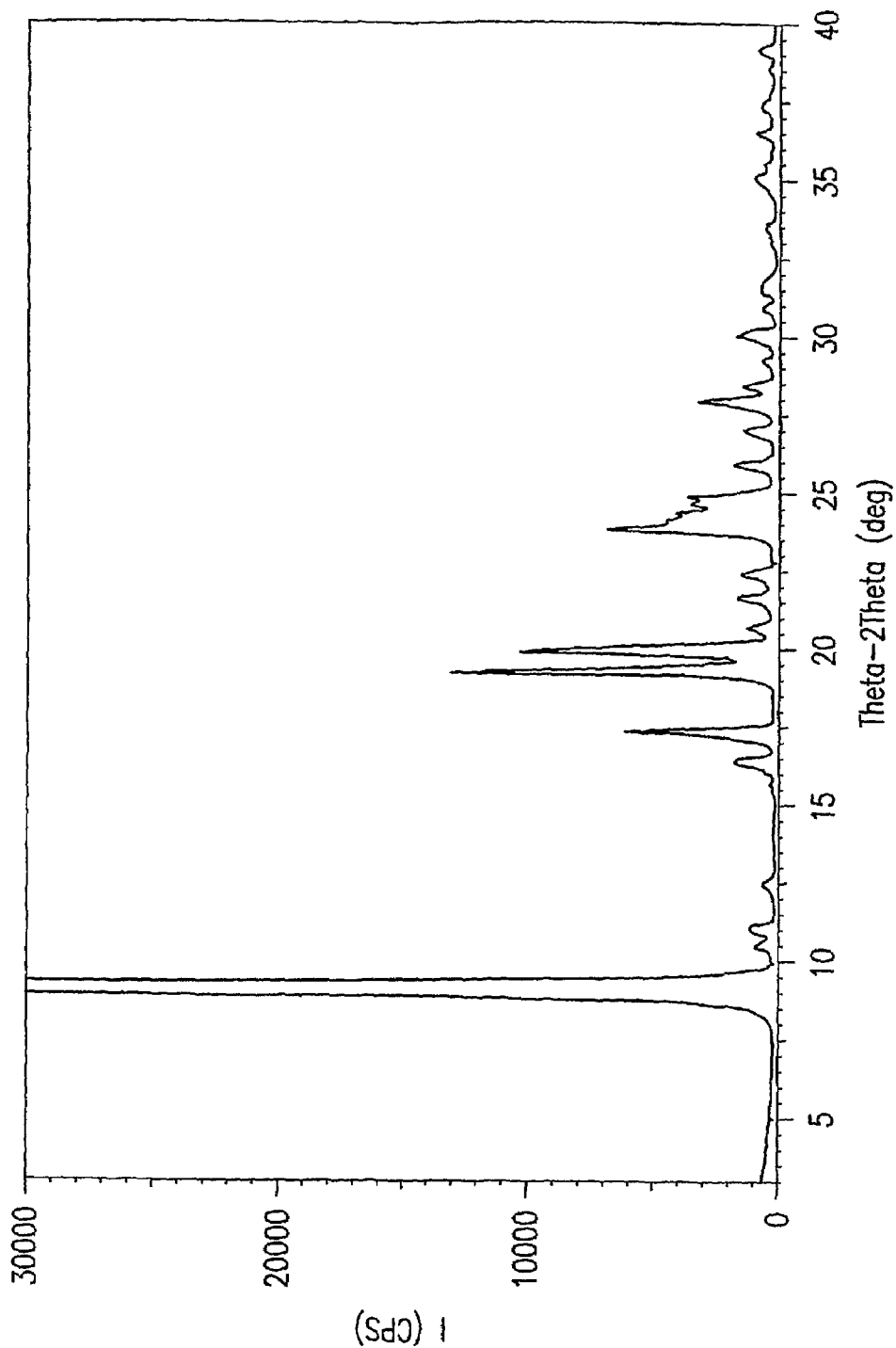
FIG. 7A-E: SAHA Form I-V.
Figure 7B:
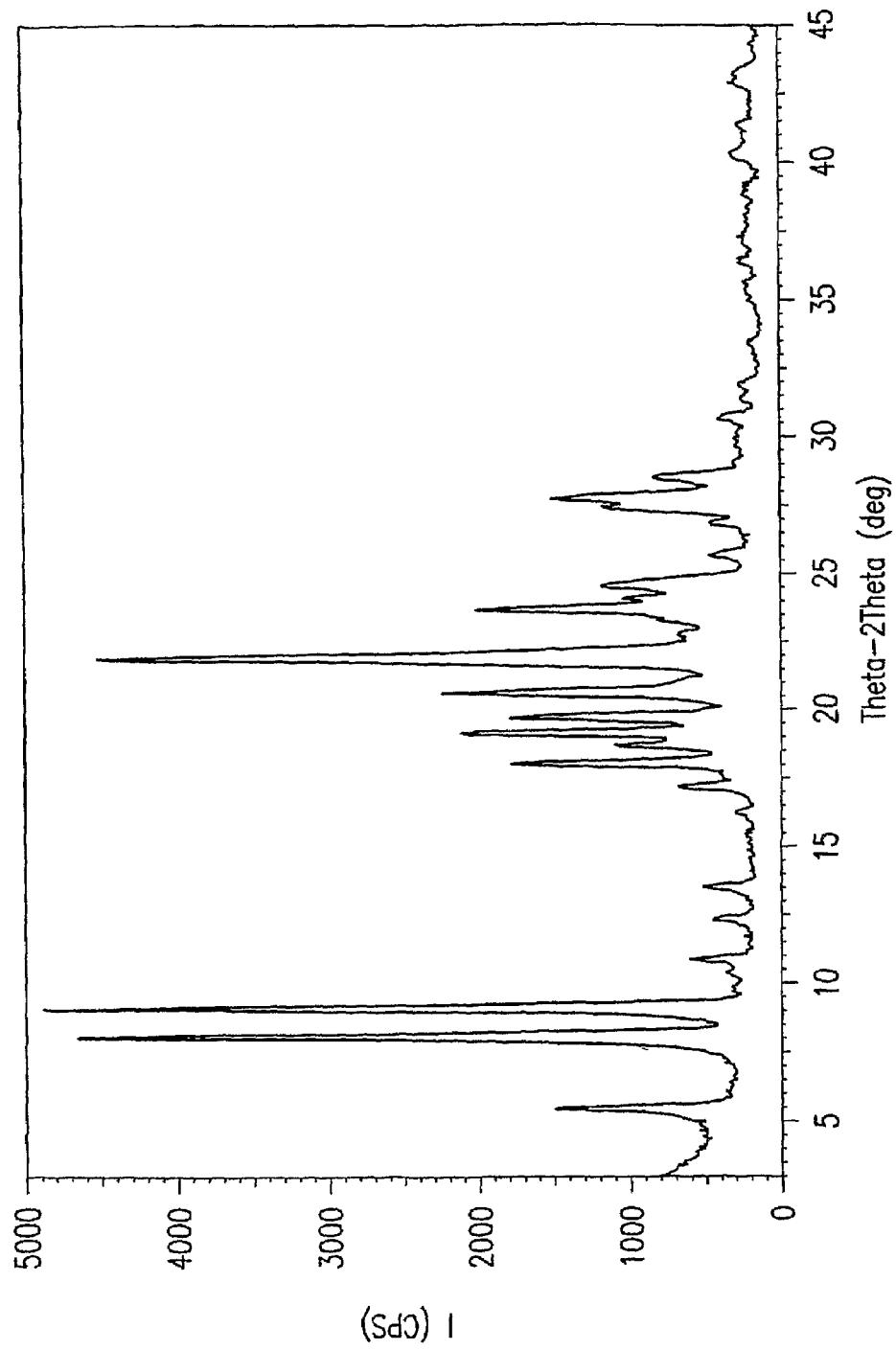
Figure 7C:
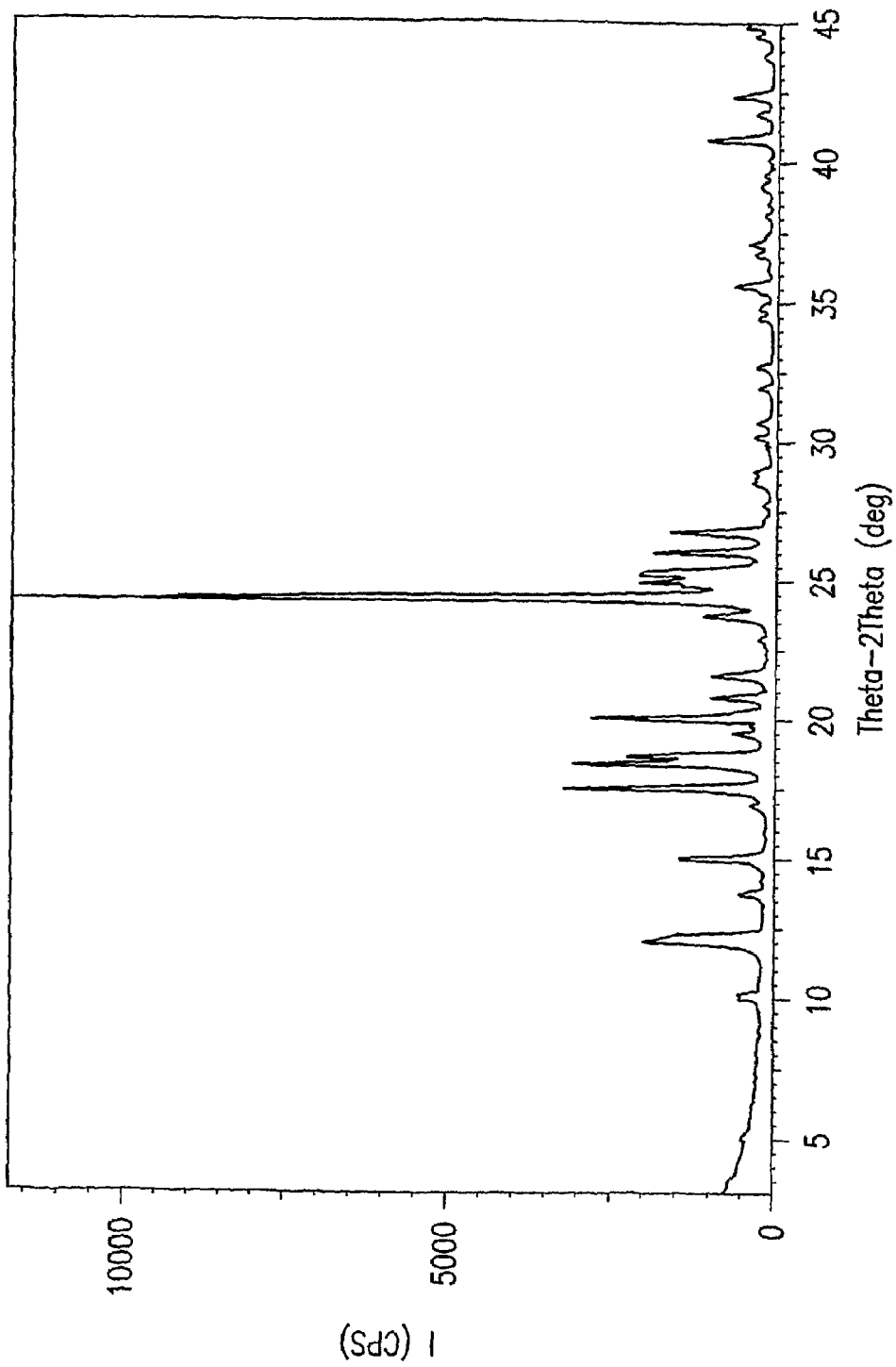
Figure 7D:
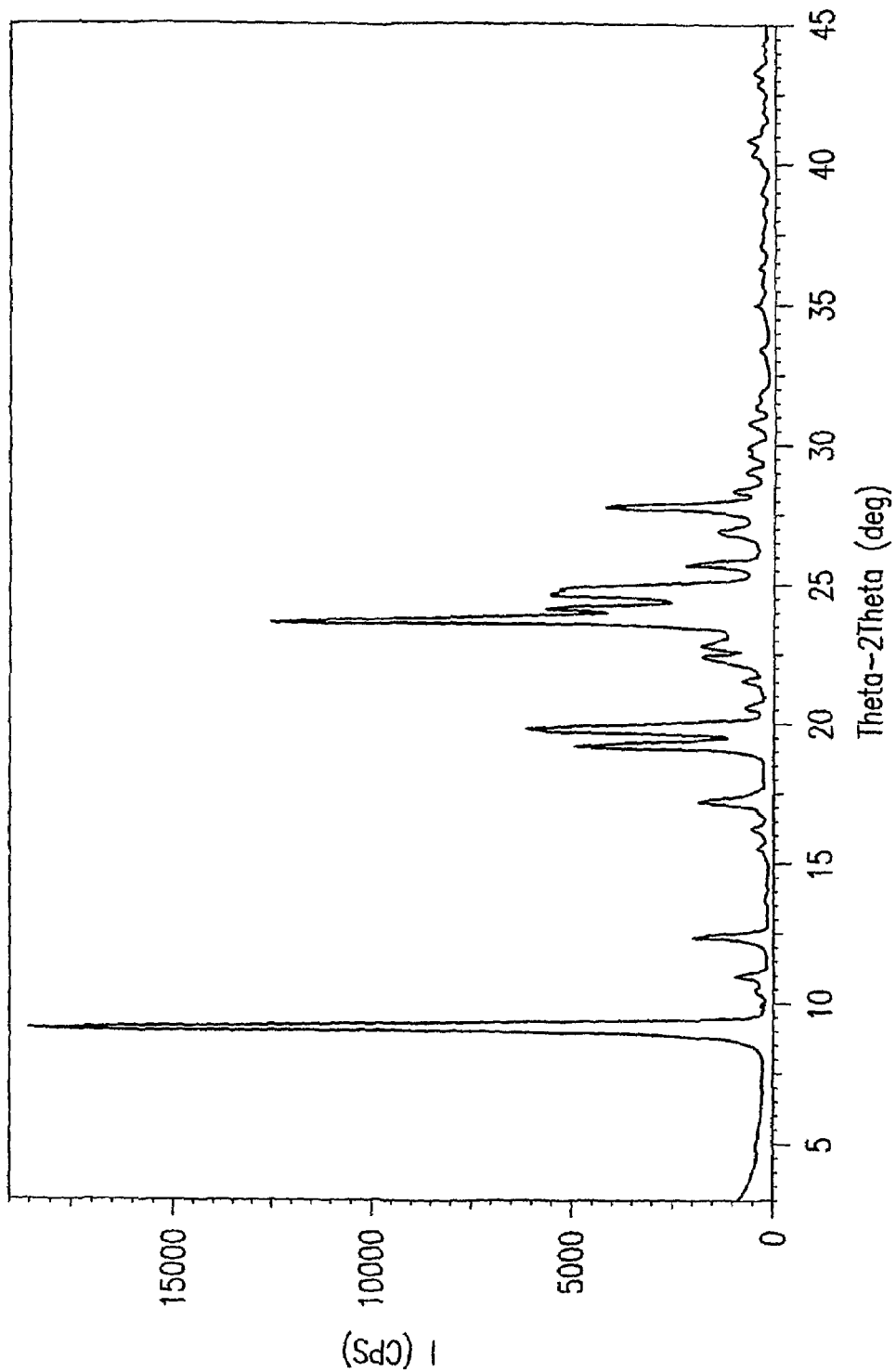
Figure 7E:
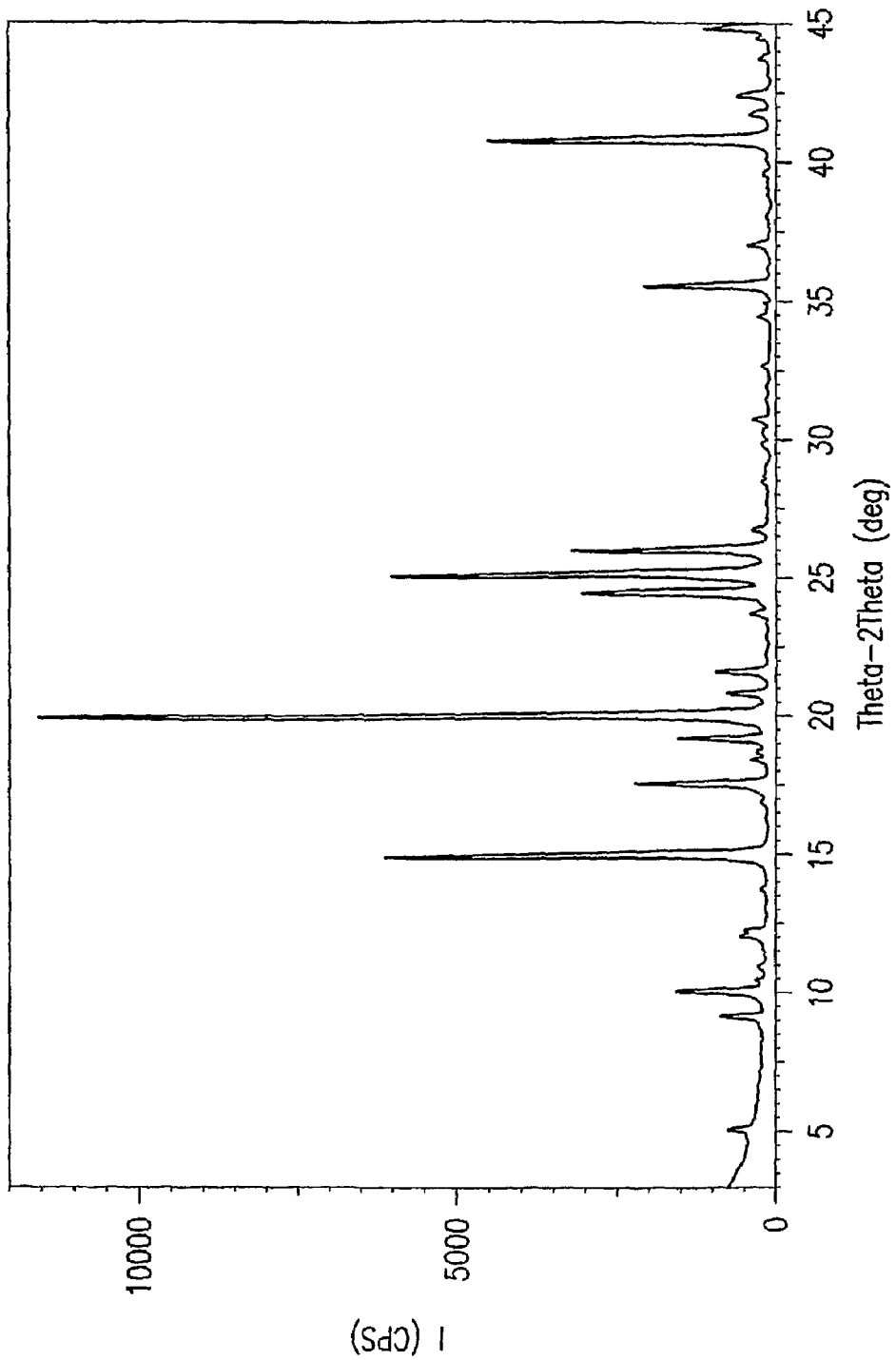

In one embodiment, the active ingredient is crystalline. In another embodiment, the active ingredient is crystalline suberoylanilide hydroxamic acid. In a particular embodiment, the crystalline suberoylanilide hydroxamic acid is SAHA Form I and characterized by an X-ray diffraction pattern substantially similar to that set forth in FIG. 7A. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0 degrees 2θ.

In one embodiment, SAHA Form I is characterized by an X-ray diffraction pattern including characteristic peaks at about 9.0, 9.4, 17.5, 19.4, 20.0, 24.0, 24.4, 24.8, 25.0, 28.0, and 43.3 degrees 2θ. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0, 43.3 degrees 2θ and lacking a peak at 13.4-14.0 and 22.7-23.0 degrees 2θ. In one embodiment, crystalline suberoylanilide hydroxamic acid is characterized by an X-ray diffraction pattern including characteristic peaks at 9.0, 9.4, 17.5, 19.4, 20.0, 24.0, 24.4, 24.8, 25.0, 28.0 degrees 2θ and lacking a peak at 13.4-14.0 and 22.7-23.0 degrees 2θ. In one embodiment, SAHA Form I is additionally characterized by the lack of at least one peak at about <8.7, 10.0-10.2, 13.4-14.0, 15.0-15.2, 17.5-19.0, 20.1-20.3, 21.1-21.3, 22.0.-22.22, 22.7-23.0, 25.0-25.5, 26.0-26.2, and 27.4-27.6 degrees 2θ. In another embodiment, SAHA Form I is further characterized by a Differential Scanning Calorimetry (DSC) thermogram having a single maximum value at about 164.4±2.0, as measured by a Perkins Elmer DSC 6 Instrument. 5. In one embodiment, the crystalline suberoylanilide hydroxamic acid has unit cell parameters of a=10.9 Å, b=7.9 Å, c=16.4 Å, α=90°, β=97.8°, γ=90°, space group $P2_1/n$.

In a particular embodiment, the crystalline suberoylanilide hydroxamic acid is SAHA Form IV and is characterized by an X-ray diffraction pattern including characteristic peaks at about 8.8, 9.3, 11.0, 12.4, 17.4, 19.4, 19.9, 22.4, 22.9, 23.83, 24.2, 24.8, 25.8, 27.0, 27.8, 28.4 degrees 2θ.

Pharmaceutical Compositions

The active ingredient can be incorporated into pharmaceutical compositions suitable for oral administration. The active ingredient may optionally be incorporated with a pharmaceutically acceptable carrier or excipient. In one embodiment, the pharmaceutically acceptable carrier is in solid particle form. Any inert excipient that is commonly used as a carrier or diluent may be used in the formulations of the present invention, such as for example, a gum, a starch, a sugar, a cellulosic material, an acrylate, or mixtures thereof. In one embodiment, the diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical composition described herein may further be comprised of microcrystalline cellulose, croscarmellose sodium and magnesium stearate. The percentage of the active ingredient and various excipients in the formulations may vary. For example, the composition may comprise between about 20 and 90%, between about 50-80% or between about 60-70% by weight of the active ingredient. Furthermore, the composition may comprise between about 10 and 70%, between about 20-40%, between about 25-35% by weight microcrystalline cellulose as a carrier or diluent. Furthermore, the composition may comprise between about 1 and 30%, between about 1-10%, between about 2-5% by weight croscarmellose sodium as a disintegrant. Furthermore, the composition may comprise between about 0.1-5% or about 0.5-1.5% by weight magnesium stearate as a lubricant.

In one embodiment, the pharmaceutical composition of the invention is about 50-80% by weight of active ingredient; about 20-40% by weight microcrystalline cellulose; about 1-10% by weight croscarmellose sodium; and about 0.1-5% by weight magnesium stearate. In another embodiment, the pharmaceutical composition of the invention is about 60-70% by weight of active ingredient; about 25-35% by weight microcrystalline cellulose; about 2-5% by weight croscarmellose sodium; and about 0.5-1.5% by weight magnesium stearate. In one embodiment, the pharmaceutical composition described comprises about 50-200 mg or 50-600 mg of SAHA Form I.

A current embodiment of the invention is a solid formulation of SAHA with microcrystalline cellulose, NF (Avicel Ph 101), sodium croscarmellose, NF (AC-Di-Sol) and magnesium stearate, NF, contained in a gelatin capsule. A further embodiment is a pharmaceutical composition comprising about 100 mg active ingredient, about 44.3 mg of microcrystalline cellulose, about 4.5 mg of croscarmellose sodium, about 1.2 mg of magnesium stearate.

In one embodiment, the pharmaceutical compositions are administered orally, and are thus formulated in a form suitable for oral administration, i.e., as a solid or liquid form. Suitable solid oral formulations include for example, tablets, capsules, pills, granules, pellets and the like. Suitable liquid oral formulations include for example, emulsions, oils and the like. In one embodiment of the present invention, the composition is formulated in a capsule. In accordance with this embodiment, the compositions of the present invention comprise a hard gelatin capsule in addition to the active ingredient and the inert carrier or diluent.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be non-aqueous solutions, suspensions, emulsions or oils. Examples of non-aqueous solvents are propylene glycol, polyethylene glycol, and injectable organic esters such as ethyl oleate. Examples of oils are those of petroleum, animal, vegetable, or synthetic origin, for example, peanut oil, soybean oil, mineral oil, olive oil, sunflower oil, and fish-liver oil. Suspensions can also include the following components: fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA).

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active ingredient is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

In one embodiment, the oral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms of the invention are dictated by and directly dependent on the unique characteristics of the active ingredient and the particular therapeutic effect to be achieved, and the limitations inherent in the art of compounding such an active compound for the treatment of individuals. In certain embodiments, the dosage unit contains about 600 mg, 550 mg, 500 mg, 450 mg, 400 mg, 350 mg, 300 mg, 250 mg, 200 mg, 150 mg, 110 mg, 105 mg, 100 mg, 95 mg, 90 mg, 85 mg, 80 mg, 75 mg, 70 mg, 65 mg, 60 mg, 55 mg, 50 mg, 45 mg, or 40 mg of active ingredient. In one embodiment, the amount of the active ingredient is about 100 mg.

The pharmaceutical compositions can be included in a container, pack, or dispenser together with instructions for administration. In one embodiment, the pharmaceutical composition is a single capsule, wherein the amount of the active ingredient is about 100 mg. In one embodiment, the pharmaceutical composition is two capsules, wherein each capsule contains active ingredient of about 50 mg.

Process of Producing Compositions with Specified Dissolution Rates

The present invention provides a process of producing a crystalline composition comprising suberoylanilide hydroxamic acid or a pharmaceutically acceptable salt or hydrate thereof as an active ingredient, wherein about 100 mg of the active ingredient has an in vitro dissolution profile with a similarity factor (f2) of at least 50 to 100 compared to the reference dissolution profile shown in FIG. 2, comprising the steps of:
  (a) crystallizing at least two batches of said active ingredient; and
  (b) blending at least two batches of the crystalline active ingredient to produce said crystalline composition.

In an alternative process, the crystalline composition is produced by the following steps:
  (a) milling or wet-milling crystalline active ingredient to produce at least one first batch of crystalline active ingredient;
  (b) crystallizing the active ingredient to produce at least one second batch of crystalline active ingredient that is larger in size than the milled or wet-milled crystalline active ingredient;
  (c) blending at least the first batch with at least the second batch of crystalline active ingredient to produce said crystalline composition.

The crystalline composition can then be further processed to produce a pharmaceutical composition, wherein the entire active ingredient has an in vitro dissolution profile with a similarity factor (f2) of at least 50 to 100 compared to the reference dissolution profile shown in FIG. 1. This can be accomplished, by applying pressure to the crystalline composition, for example by encapsulation of the crystalline compositions with or without excipients. Due to the pressure incurred during the capsule packing process, breakage occurs on the particles of the active ingredient, which affects the particle size distribution, thereby affecting the dissolution rate. The amount of particle breakage can be affected by capsule density, which is impacted by the tamping pin type and capsule fill weight.

Therefore, in yet another embodiment, the present invention provides a process of producing a pharmaceutical composition comprising suberoylanilide hydroxamic acid or a pharmaceutically acceptable salt or hydrate thereof as an active ingredient, wherein the entire active ingredient of the pharmaceutical composition has an in vitro dissolution profile with a similarity factor (f2) of at least 50 to 100 compared to the reference dissolution profile shown in FIG. 1, comprising the steps of:
  (a) crystallizing at least two batches of said active ingredient;
  (b) blending at least two batches of the crystalline active ingredient; and
  (c) producing said pharmaceutical composition from the blended batches.

In one embodiment, the crystalline active ingredient is prepared from crystallization of active ingredient or crude active ingredient from an organic solvent or a mixture of an organic solvent and water. In one embodiment, the organic solvent is one or more of methanol, ethanol, acetonitrile, isopropanol and acetic acid. In one embodiment, the organic solvent is ethanol. In one embodiment, the mixture comprises about 40-99% ethanol. In one embodiment, the mixture comprises about 40-99% ethanol and 60-1% water. In one embodiment, step (c) is performed by encapsulating a portion of the blended crystalline active ingredient.

In an alternative process the pharmaceutical composition is produced by the following steps:
  (a) milling or wet-milling crystalline active ingredient to produce at least a first batch of crystalline active ingredient;
  (b) crystallizing the active ingredient to produce at least a second batch of crystalline active ingredient that is larger in size than the milled or wet-milled crystalline active ingredient;
  (c) blending at least the first batch with at least the second batch of crystalline active ingredient; and
  (d) producing said pharmaceutical composition from said blended first and second batch.

In one embodiment, the first batch of crystalline active ingredient has a mean particle size of less than about 50 μm and the second batch of crystalline active ingredient has a mean particle size more than about 130 μm. In another embodiment, the first batch of crystalline active ingredient has a mean particle size of less than about 50 μm and the second batch of crystalline active ingredient has a mean particle size in the range of about 120 to 160 μm. In a particular embodiment, 95% of the first batch of crystalline active ingredient is less than about 100 μm. In one embodiment, 95% of the second batch crystals are less than about 300 μm. In one embodiment, step (d) is performed by encapsulating a portion of the blended crystalline active ingredient.

In one embodiment, the first batch of crystalline ingredient has a mean particle size of less than about 60 μm and the second batch of crystalline active ingredient has a mean particle size of about 100-250 μm. In another embodiment, the first batch of crystalline ingredient has a mean particle size in the range of about 25 to 45 μm and the second batch of crystalline active ingredient has a mean particle size in the range of about 130 to 180 μm.

In one embodiment, the crystalline active ingredient is prepared from crystallization of active ingredient or crude active ingredient from an organic solvent or a mixture of an organic solvent and water. In one embodiment, the organic solvent is one or more of methanol, ethanol, acetonitrile, isopropanol and acetic acid. In one embodiment, the organic solvent is ethanol. In one embodiment, the mixture comprises about 40-99% ethanol. In one embodiment, the mixture comprises about 40-99% ethanol and 60-1% water.

In another embodiment, in step (c), about 40-95% of the second batch crystalline active ingredient is blended with about 60-5% of the first batch milled crystalline active ingredient.

In one embodiment of the above processes the crystallization step involves seeding. In another embodiment of the above processes, the blending ratio is determined by a computer simulation program that uses an encapsulation breakage model and a dissolution model. In one embodiment, the blending ratio is optimized to obtain a composition with a SAHA dissolution rate profile similar to a reference with a dissolution rate profile in FIG. 1.

The invention also provides a process of producing recrystallized active ingredient of suberoylanilide hydroxamic acid or a pharmaceutically acceptable salt or hydrate thereof, comprising the steps of:
(a) providing crystalline active ingredient to an organic solvent, water or a mixture thereof to form a slurry;
(b) heating the slurry to establish 2-30% undissolved crystalline active ingredient; and
(c) cooling the slurry to obtain the recrystallized active ingredient.

In one embodiment, the crystalline active ingredient in step (a) has a mean particle size less than about 60 μm.

In another embodiment, the crystalline active ingredient is prepared by the steps of:
(i) adding crystalline active ingredient to an organic solvent, water or mixture thereof to form a seed slurry; and
(ii) wet-milling the slurry to achieve wet-milled crystalline active ingredient.

In another embodiment, the crystalline active ingredient is prepared by the step of dry-milling crystalline active ingredient. In a further embodiment, the crystalline active ingredient is obtained in the presence of hydroxylamine.

In one embodiment, in step (a), a mixture of 40-99% ethanol and 60-1% water is used. In another embodiment, in step (b), the slurry is heated to 60-75° C. for about 1-3 hours. In a further embodiment, step (c) is performed by cooling from between 60 to 75° C. to between 25 to −5° C. in about 15 to 72 hours.

In another embodiment, the processes above further comprises blending about 40-95% of recrystallized active ingredient with about 60-5% crystalline active ingredient having mean particle size less than about 60 μm.

The invention also provides a process of producing crystalline active ingredient of suberoylanilide hydroxamic acid, comprising the steps of:
(a) providing crystalline active ingredient to a mixture of 40-99% ethanol and 60-1% water to form a slurry;
(b) heating the slurry to establish 2-30% undissolved crystalline active ingredient;
(c) cooling the slurry to obtain the recrystallized active ingredient; and
(d) blending about 40-95% of recrystallized active ingredient with about 60-5% crystalline active ingredient having mean particle size less than about 60 μm.

The present invention also provides a process of producing recrystallized active ingredient of suberoylanilide hydroxamic acid or a pharmaceutically acceptable salt or hydrate thereof, comprising the steps of:

(a) adding crystalline active ingredient to an organic solvent or a mixture of organic solvent and water to form a slurry;
(b) wet-milling the slurry to achieve crystalline active ingredient with mean particle size less than about 50 μm;
(c) heating the wet-milled slurry to establish about a 5-30% seed bed; and
(d) cooling the slurry to below 25° C. to obtain the recrystallized active ingredient.

In one embodiment, in step (a), the mixture contains ethanol and water, in particular, about 40-95% ethanol. In a particular embodiment, a mixture of about 1:1 ethanol and water is used. In another particular embodiment, a mixture of about 9:1 ethanol and water is used. In one embodiment, after the wet-milling step, at least 80-95%, or in another embodiment, 95% of the crystalline active ingredient has a particle size less than about 100 μm.

In one embodiment, step c) establishes about a 10-20% seed bed. In a particular embodiment, step c) establishes about a 15% seed bed. In one embodiment, step c) is achieved by heating the wet-milled slurry at 60-70° C. for 1-3 hours. In another embodiment, step c) is achieved by heating the wet-milled slurry at 63-66° C. for about 1-3 hours. In a particular embodiment, step c) is achieved by heating the wet-milled slurry at 64-65° C. for about 1-3 hours.

In one embodiment, step (d) is performed by cooling from 60-70° C. to 25-5° C. in about 15 to 30 hours. In another embodiment, step (d) is performed by cooling from 64-65° C. to 20-5° C. in about 15 to 30 hours. The cooling process may involve combinations of decreasing the temperature within a specified period of time, and maintaining the temperature for a specified period of time.

The above processes may further comprise the step of blending recrystallized active ingredient with wet-milled crystalline active ingredient that is produced by steps identical to steps (a) and (b). The wet-milled crystalline active ingredient can be taken from a portion of the wet-milled material of step b). Alternatively, the wet-milled crystalline active ingredient can be separately prepared according to steps a) and b). Therefore, the wet-milled crystalline active ingredient may be produced in the same or different solvent or mixture as compared to the crystallization conditions of the recrystallized active ingredient. The blending ratio may be determined by computer simulation software. In one embodiment, the blending ratio is 60-80% of recrystallized active ingredient and 40-20% wet-milled crystalline active ingredient. In a particular embodiment, the blending ratio is about 70% of recrystallized active ingredient and about 30% wet-milled crystalline active ingredient. In another particular embodiment, in step (a), a mixture of 9:1 or 1:1 ethanol water is used, and the blending ratio is 70% of recrystallized active ingredient and 30% wet-milled crystalline active ingredient.

The invention also provides a process of producing recrystallized active ingredient of suberoylanilide hydroxamic acid or a pharmaceutically acceptable salt or hydrate thereof, comprising the steps of:
(a) providing crystalline active ingredient to an organic solvent, water or a mixture thereof to a first vessel to form a slurry;
(b) heating the slurry in the first vessel to dissolve substantially all of the crystalline active ingredient;
(c) cooling the contents in step (b) in the first vessel to a temperature that supersaturates the solution.
(d) adding seeds of the crystalline active ingredient to the contents of step (c);
(e) aging the contents of step (d) at the same temperature as step (c);

(f) cooling the contents in step (e) to obtain the recrystallized active ingredient.

In one embodiment, step (d) comprises the steps of:
(i) providing crystalline active ingredient in an organic solvent, water or mixture thereof to form a seed slurry;
(ii) heating and aging the seed slurry to dissolve a portion of the seeds;
(iii) cooling the contents in step (ii) to the same temperature as in step (c);
(iv) transferring the seed slurry in step (iii) to the first vessel.

In one embodiment, the crystalline active ingredient of step (i) has a mean particle size less than about 60 μm. In another embodiment, step (i) is prepared by the steps of:
(v) adding crystalline active ingredient to an organic solvent, water or mixture thereof to form a seed slurry;
(vi) wet-milling the slurry to achieve wet-milled crystalline active ingredient.

In another embodiment, step (i) is prepared by the steps of:
(v) dry-milling crystalline active ingredient;
(vi) adding the dry-milled crystalline active ingredient to an organic solvent, water or mixture thereof to form a seed slurry.

In a further embodiment, after step (vi), further comprises the step of isolating, washing and drying the wet-milled crystalline active ingredient prior to step (d).

In one embodiment, the crystalline active ingredient of step (a) is obtained in the presence of hydroxylamine. In another embodiment, a mixture of 40-99% ethanol and 60-1% water is used in step (a) and (i). In a further embodiment, a mixture of ethanol to water ratio of 49:51 to 51:49 is used in step (a) and (i)

In one embodiment, in step (b), the slurry is heated to 60-75° C. under minimum of 15 psig pressure. In another embodiment, in step (b), the slurry is heated to 67-70° C. under minimum of 15 psig pressure.

In one embodiment, in step (c), the contents are cooled to 60-65° C. In another embodiment, in step (c), the contents are cooled to 61-63° C.

In one embodiment, in step (ii), the seed slurry is heated to 62-66° C. In another embodiment, in step (ii), the seed slurry is heated to 64-65° C.

In one embodiment, step (f) is performed by cooling from between 60 to 70° C., to between 25 to −5° C. in about 15 to 72 hours. In another embodiment, step (f) is performed by cooling from between 60 to 64° C., to between 0 to 10° C. in about 15 to 72 hours.

The present invention also provides a process of producing recrystallized active ingredient of suberoylanilide hydroxamic acid or a pharmaceutically acceptable salt or hydrate thereof, comprising the steps of:
(a) adding crystalline active ingredient to an organic solvent or mixture of organic solvent and water to form a slurry;
(b) wet-milling the slurry to achieve crystalline active ingredient with mean particle size less than about 50 μm;
(c) heating the wet-milled slurry to 60-70° C. to produce a seed slurry;
(d) providing crystalline active ingredient in an organic solvent or mixture of organic solvent and water;
(e) heating the material in step (d) to dissolve the crystalline active ingredient;
(f) cooling the material in step (e) to obtain a supersaturated solution with no nucleation;
(g) transferring the seed slurry in step (c) to the supersaturated solution; and
(h) cooling the material in step (g) to below 25° C.

In one embodiment, in step (a) and (d), a mixture is used which contains ethanol and water, in particular, about 40-95% ethanol. In a particular embodiment, a mixture of about 1:1 ethanol and water is used. In another particular embodiment, a mixture of about 9:1 ethanol and water is used. The percentage of organic solvent used in step (a) or (d) may be the same or different. For example, in step (a), about 40-100% ethanol may be used, while in step d) a mixture of about 1:1 or 9:1 ethanol may be used. In one embodiment, after the wet-milling step, at least 80-95%, or 95% of the crystalline active ingredient has a particle size less than about 100 μm.

In one embodiment, step c) establishes about a 10-20% seed bed. In a particular embodiment, step c) establishes about a 15% seed bed. In another embodiment, the wet-milled slurry is heated to 63-67° C. In another embodiment, the wet-milled slurry is heated to 62-66° C. at 20-25 psig, and cooled to 61-63° C. In another embodiment, the wet-milled slurry is heated to dissolve 50% of the seed solid.

In one embodiment, in step (e), heating is at 65-75° C. In a particular embodiment, in step (e), heating is at 67-70° C. In one embodiment, in step (e), the heating is performed under 20-25 psig pressure. In another embodiment, in step (f), cooling is at 60-65° C. In yet another embodiment, in step (f), cooling is at 61 to 63° C.

In another embodiment, after step (g) and before step (h), the mixture is aged for 2 hours at 61 to 63° C. In one embodiment, in step (h), the cooling is achieved through three linear steps in 26 hours.

The invention also provides a process of producing recrystallized active ingredient of suberoylanilide hydroxamic acid, comprising the steps of:
(a) providing crystalline active ingredient to a mixture of 40-99% ethanol and 60-1% water to a first vessel to form a slurry;
(b) heating the slurry in the first vessel to dissolve substantially all of the crystalline active ingredient;
(c) cooling the contents in step (b) in the first vessel to supersaturate the solution.
(d) adding crystalline active ingredient to the contents of step (c);
(e) aging the contents of step (d) at the same temperature as step (c);
(f) cooling the contents in step (e) to obtain the recrystallized active ingredient.

In a particular embodiment of the above processes, the active ingredient is suberoylanilide hydroxamic acid. In one embodiment, the crystalline active ingredient is SAHA Form I.

Crystallization with Organic Solvents

In one particular embodiment, the crystalline active ingredient or recrystallized active ingredient is crystallized from an organic solvent or a mixture of water and an organic solvent. The organic solvent may be an alcohol such as methanol, ethanol or isopropanol. In one embodiment, the organic solvent is one or more of methanol, ethanol, acetonitrile, isopropanol and acetic acid. In one embodiment, the organic solvent is ethanol.

In another embodiment, the mixture of organic solvent and water comprises about 1-99% organic solvent and about 99-1% of water. In another embodiment, the mixture comprises 40-99% ethanol and 60%-1% of water. In one embodiment, the mixture comprises about 15-85% organic solvent and about 1-15% water. In a particular embodiment, the mixture comprises about 85% organic solvent and about 15% water. In another particular embodiment, the mixture comprises 1:1 ethanol and water. In yet another particular embodiment, the mixture comprises 9:1 ethanol and water. The ratios or percentages of organic solvent to water described here are by volume.

In one particular embodiment, the mixture of an organic solvent and water is an alcohol and water (e.g. methanol/water, ethanol/water, isopropanol/water and the like). However, it should be apparent to a person skilled in the art that the crystallizations of the methods described herein can be carried out in any suitable solvents or solvent mixtures which may be readily selected by one of skill in the art of organic synthesis. Such suitable organic solvents, as used herein may include, by way of example and without limitation, chlorinated solvents, hydrocarbon solvents, ether solvents, polar protic solvents and polar aprotic solvents. Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 1,2-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane. Suitable hydrocarbon solvents include, but are not limited to benzene, cyclohexane, pentane, hexane, toluene, cycloheptane, methylcyclohexane, heptane, ethylbenzene, m-, o-, or p-xylene, octane, indane, nonane. Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable polar protic solvents include, but are not limited to methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol. Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, hexamethylphosphoramide.

Methods of Administration

In all of the methods described herein, the pharmaceutical composition may be administered orally in a gelatin capsule. The composition may be administered in unit dosages according to the methods described herein once-daily, twice-daily or three times-daily.

The daily administration is then repeated continuously for a period of several days to several years. Oral treatment may continue for between one week and the life of the patient. In one embodiment, the administration takes place for five consecutive days after which time the patient can be evaluated to determine if further administration is required. The administration can be continuous or intermittent, i.e., treatment for a number of consecutive days followed by a rest period.

The pharmaceutical compositions of the present invention may be administered at orally at a total daily dose of between 25 to 4000 mg/m$^2$, for example, about 25 to 1000 mg, 50-1000 mg, 100 mg, 200 mg, 300 mg, 400 mg, 600 mg, 800 mg, 1000 mg and the like. Typically the compound is administered as a single dose when administering up to 400 mg to the patient. For higher total dosages (i.e., greater than 400 mg), the total is split into multiple dosages, for example, twice daily, three times daily or the like, or spread out over equal periods of time during the day. For example, two doses, e.g., 500 mg each, can be administered 12 hours apart to achieve a total dosage of 1000 mg in a day.

In one embodiment, SAHA is administered to the patient at a total daily dosage of 200 mg. In another embodiment, SAHA is administered to the patient at a total daily dosage of 400 mg. In another embodiment, SAHA is administered to the patient at a total daily dosage of 600 mg.

In one embodiment, the amount of the active ingredient administered to the patient is less than an amount that would cause toxicity in the patient. In certain embodiments, the amount of the active ingredient that is administered to the patient is less than the amount that causes a concentration of the compound in the patient's plasma to equal or exceed the toxic level of the compound. In one embodiment, the concentration of the active ingredient in the patient's plasma is maintained at between about 10 nM to about 5000 nM. The optimal amount of the active ingredient that should be administered to the patient in the practice of the present invention will depend on the particular compound used and the type of cancer being treated.

Combination Therapy

The methods of the present invention may also comprise initially administering to the subject an antitumor agent so as to render the neoplastic cells in the subject resistant to an antitumor agent and subsequently administering an effective amount of any of the compositions of the present invention, effective to selectively induce terminal differentiation, cell growth arrest and/or apoptosis of such cells.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those agents that promote depolarization of tubulin. In one embodiment, the antitumor agent is colchicine or a vinca alkaloid; vinblastine or vincristine. In embodiments where the antitumor agent is vincristine, the cells preferably are treated so that they are resistant to vincristine at a concentration of about 5 mg/ml. The treating of the cells to render them resistant to an antitumor agent may be effected by contacting the cells with the agent for a period of at least 3 to 5 days. The contacting of the resulting cells with any of the compounds above is performed as described previously. In addition to the above chemotherapy agents, the compounds may also be administered together with radiation therapy.

Alkylating Agents

Alkylating agents react with nucleophilic residues, such as the chemical entities on the nucleotide precursors for DNA production. They affect the process of cell division by alkylating these nucleotides and preventing their assembly into DNA.

Examples of alkylating agents include, but are not limited to, bischloroethylamines (nitrogen mustards, e.g., chlorambucil, cyclophosphamide, ifosfamide, mechlorethamine, melphalan, uracil mustard), aziridines (e.g., thiotepa), alkyl alkone sulfonates (e.g., busulfan), nitrosoureas (e.g., carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfhydryl, carboxyl, and imidazole groups.

Under physiological conditions, these drugs ionize and produce positively charged ion that attach to susceptible nucleic acids and proteins, leading to cell cycle arrest and/or cell death. The alkylating agents are cell cycle phasenonspecific agents because they exert their activity independently of the specific phase of the cell cycle. The nitrogen mustards and alkyl alkone sulfonates are most effective against cells in the G1 or M phase. Nitrosoureas, nitrogen mustards, and aziridines impair progression from the G1 and S phases to the M phases. Chabner and Collins eds. (1990) "Cancer Chemotherapy: Principles and Practice", Philadelphia: J B Lippincott.

The alkylating agents are active against wide variety of neoplastic diseases, with significant activity in the treatment of leukemias and lymphomas as well as solid tumors. Clinically this group of drugs is routinely used in the treatment of acute and chronic leukemias; Hodgkin's disease; non-Hodgkin's lymphoma; multiple myeloma; primary brain tumors; carcinomas of the breast, ovaries, testes, lungs, bladder, cervix, head and neck, and malignant melanoma.

The major toxicity common to all of the alkylating agents is myelosuppression. Additionally, gastrointestinal adverse effects of variable severity occur commonly and various organ toxicities are associated with specific compounds. Black and Livingston (1990) Drugs 39: 489-501; and 39: 652-673.

Antibiotics

Antibiotics (e.g., cytotoxic antibiotics) act by directly inhibiting DNA or RNA synthesis and are effective throughout the cell cycle. Examples of antibiotic agents include anthracyclines (e.g., doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions.

Bleomycin is generally believed to chelate iron and forms an activated complex, which then binds to bases of DNA, causing strand scissions and cell death.

The antibiotic agents have been used as therapeutics across a range of neoplastic diseases, including carcinomas of the breast, lung, stomach and thyroids, lymphomas, myelogenous leukemias, myelomas, and sarcomas. The primary toxicity of the anthracyclines within this group is myelosuppression, especially granulocytopenia. Mucositis often accompanies the granulocytopenia and the severity correlates with the degree of myelosuppression. There is also significant cardiac toxicity associated with high dosage administration of the anthracyclines.

Antimetabolic Agents

Antimetabolic agents (i.e., antimetabolites) are a group of drugs that interfere with metabolic processes vital to the physiology and proliferation of cancer cells. Actively proliferating cancer cells require continuous synthesis of large quantities of nucleic acids, proteins, lipids, and other vital cellular constituents.

Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Antimetabolic agents have widely used to treat several common forms of cancer including carcinomas of colon, rectum, breast, liver, stomach and pancreas, malignant melanoma, acute and chronic leukemia and hair cell leukemia. Many of the adverse effects of antimetabolite treatment result from suppression of cellular proliferation in mitotically active tissues, such as the bone marrow or gastrointestinal mucosa. Patients treated with these agents commonly experience bone marrow suppression, stomatitis, diarrhea, and hair loss. Chen and Grem (1992) Curr. Opin. Oncol. 4: 1089-1098.

Hormonal Agents

The hormonal agents are a group of drug that regulate the growth and development of their target organs. Most of the hormonal agents are sex steroids and their derivatives and analogs thereof, such as estrogens, progestogens, anti-estrogens, androgens, anti-androgens and progestins. These hormonal agents may serve as antagonists of receptors for the sex steroids to down regulate receptor expression and transcription of vital genes. Examples of such hormonal agents are synthetic estrogens (e.g., diethylstibestrol), antiestrogens (e.g., tamoxifen, toremifene, fluoxymesterol and raloxifene), antiandrogens (bicalutamide, nilutamide, flutamide), aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

Hormonal agents are used to treat breast cancer, prostate cancer, melanoma and meningioma. Because the major action of hormones is mediated through steroid receptors, 60% receptor-positive breast cancer responded to first-line hormonal therapy; and less than 10% of receptor-negative tumors responded. The main side effect associated with hormonal agents is flare. The frequent manifestations are an abrupt increase of bony pain, erythema around skin lesions, and induced hypercalcemia.

Specifically, progestogens are used to treat endometrial cancers, since these cancers occur in women that are exposed to high levels of oestrogen unopposed by progestogen.

Antiandrogens are used primarily for the treatment of prostate cancer, which is hormone dependent. They are used to decrease levels of testosterone, and thereby inhibit growth of the tumor.

Hormonal treatment of breast cancer involves reducing the level of oestrogen-dependent activation of oestrogen receptors in neoplastic breast cells. Anti-oestrogens act by binding to oestrogen receptors and prevent the recruitment of coactivators, thus inhibiting the oestrogen signal.

LHRH analogues are used in the treatment of prostate cancer to decrease levels of testosterone and so decrease the growth of the tumor.

Aromatase inhibitors act by inhibiting the enzyme required for hormone synthesis. In post-menopausal women, the main source of oestrogen is through the conversion of androstenedione by aromatase.

Plant-Derived Agents

Plant-derived agents are a group of drugs that are derived from plants or modified based on the molecular structure of the agents. They inhibit cell replication by preventing the assembly of the cell's components that are essential to cell division.

Examples of plant derived agents include vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission.

Plant-derived agents are used to treat many forms of cancer. For example, vincristine is used in the treatment of the leukemias, Hodgkin's and non-Hodgkin's lymphoma, and the childhood tumors neuroblastoma, rhabdomyosarcoma, and Wilms' tumor. Vinblastine is used against the lymphomas, testicular cancer, renal cell carcinoma, mycosis fungoides, and Kaposi's sarcoma. Doxetaxel has shown promising activity against advanced breast cancer, non-small cell lung cancer (NSCLC), and ovarian cancer.

Etoposide is active against a wide range of neoplasms, of which small cell lung cancer, testicular cancer, and NSCLC are most responsive.

The plant-derived agents cause significant side effects on patients being treated. The vinca alkaloids display different spectrum of clinical toxicity. Side effects of vinca alkaloids include neurotoxicity, altered platelet function, myelosuppression, and leukopenia. Paclitaxel causes dose-limiting neutropenia with relative sparing of the other hematopoietic cell lines. The major toxicity of the epiphyllotoxins is hematologic (neutropenia and thrombocytopenia).

Other side effects include transient hepatic enzyme abnormalities, alopecia, allergic reactions, and peripheral neuropathy.

Biologic Agents

Biologic agents are a group of biomolecules that elicit cancer/tumor regression when used alone or in combination with chemotherapy and/or radiotherapy. Examples of biologic agents include immuno-modulating proteins such as cytokines, monoclonal antibodies against tumor antigens, tumor suppressor genes, and cancer vaccines.

Cytokines possess profound immunomodulatory activity. Some cytokines such as interleukin-2 (IL-2, aldesleukin) and interferon-$\alpha$ (IFN-$\alpha$) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of 1-2 on some patients are believed to be the result of a cell-mediated immune response that discriminate between self and nonself.

Interferon-$\alpha$ includes more than 23 related subtypes with overlapping activities. IFN-$\alpha$ has demonstrated activity against many solid and hematologic malignancies, the later appearing to be particularly sensitive.

Examples of interferons include, interferon-$\alpha$, interferon-$\beta$ (fibroblast interferon) and interferon-$\gamma$ (fibroblast interferon). Examples of other cytokines include erythropoietin (epoietin-$\alpha$), granulocyte-CSF (filgrastin), and granulocyte, macrophage-CSF (sargramostim). Other immuno-modulating agents other than cytokines include bacillus Calmette-Guerin, levamisole, and octreotide, a long-acting octapeptide that mimics the effects of the naturally occurring hormone somatostatin.

Furthermore, the anti-cancer treatment can comprise treatment by immunotherapy with antibodies and reagents used in tumor vaccination approaches. The primary drugs in this therapy class are antibodies, alone or carrying e.g. toxins or chemostherapeutics/cytotoxics to cancer cells. Monoclonal antibodies against tumor antigens are antibodies elicited against antigens expressed by tumors, preferably tumor-specific antigens. For example, monoclonal antibody HERCEPTIN® (trastuzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Another example of monoclonal antibodies against tumor antigens is RITUXAN® (rituximab) that is raised against CD20 on lymphoma cells and selectively deplete normal and malignant CD20+ pre-B and mature B cells.

RITUXAN is used as single agent for the treatment of patients with relapsed or refractory low-grade or follicular, CD20+, B cell non-Hodgkin's lymphoma. MYELOTARG® (gemtuzumab ozogamicin) and CAMPATH® (alemtuzumab) are further examples of monoclonal antibodies against tumor antigens that may be used.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle checkpoints and resulting in a higher rate of controlled cell growth-cancer. Examples of the tumor suppressor genes include Duc-4, NF-1, NF-2, RB, p53, WT1, BRCA1 and BRCA2.

DPC4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WTI is involved in Wilms' tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAAs are structures (i.e., proteins, enzymes or carbohydrates) that are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), $\alpha$-fetoprotein (AFP), carcinoembryonic antigen (CEA) (produced by colon cancers and other adenocarcinomas, e.g., breast, lung, gastric, and pancreatic cancers), melanoma-associated antigens (MART-1, gap100, MAGE 1,3 tyrosinase), papillomavirus E6 and E7 fragments, whole cells or portions/lysates of autologous tumor cells and allogeneic tumor cells.

Other Therapies

Recent developments have introduced, in addition to the traditional cytotoxic and hormonal therapies used to treat cancer, additional therapies for the treatment of cancer. For example, many forms of gene therapy are undergoing preclinical or clinical trials.

In addition, approaches are currently under development that are based on the inhibition of tumor vascularization (angiogenesis). The aim of this concept is to cut off the tumor from nutrition and oxygen supply provided by a newly built tumor vascular system.

In addition, cancer therapy is also being attempted by the induction of terminal differentiation of the neoplastic cells. Suitable differentiation agents include the compounds disclosed in any one or more of the following references.
a) Polar compounds (Marks et al (1987); Friend, C., Scher, W., Holland, J. W., and Sato, T. (1971) Proc. Natl. Acad. Sci. (USA) 68: 378-382; Tanaka, M., Levy, J., Terada, M., Breslow, R., Rifkind, R. A., and Marks, P. A. (1975) Proc. Natl. Acad. Sci. (USA) 72: 1003-1006; Reuben, R. C., Wife, R. L., Breslow, R., Rifkind, R. A., and Marks, P. A. (1976) Proc. Natl. Acad. Sci. (USA) 73: 862-866);
b) Derivatives of vitamin D and retinoic acid (Abe, E., Miyaura, C., Sakagami, H., Takeda, M., Konno, K., Yamazaki, T., Yoshika, S., and Suda, T. (1981) Proc. Natl. Acad. Sci. (USA) 78: 4990-4994; Schwartz, E. L., Snoddy, J. R., Kreutter, D., Rasmussen, H., and Sartorelli, A. C. (1983) Proc. Am. Assoc. Cancer Res. 24: 18; Tanenaga, K., Hozumi, M., and Sakagami, Y. (1980) Cancer Res. 40: 914-919);
c) Steroid hormones (Lotem, J. and Sachs, L. (1975) Int. J. Cancer 15: 731-740);
d) Growth factors (Sachs, L. (1978) Nature (Lond.) 274: 535, Metcalf, D. (1985) Science, 229: 16-22);
e) Proteases (Scher, W., Scher, B. M., and Waxman, S. (1983) Exp. Hematol. 11: 490-498; Scher, W., Scher, B. M., and Waxman, S. (1982) Biochem. & Biophys. Res. Comm. 109: 348-354);
f) Tumor promoters (Huberman, E. and Callaham, M. F. (1979) Proc. Natl. Acad. Sci. (USA) 76: 1293-1297; Lottem, J. and Sachs, L. (1979) Proc. Natl. Acad. Sci. (USA) 76: 5158-5162); and
g) inhibitors of DNA or RNA synthesis (Schwartz, E. L. and Sartorelli, A. C. (1982) Cancer Res. 42: 2651-2655, Terada, M., Epner, E., Nudel, U., Salmon, J., Fibach, E., Rifkind, R. A., and Marks, P. A. (1978) Proc. Natl. Acad. Sci. (USA) 75: 2795-2799; Morin, M. J. and Sartorelli, A. C. (1984) Cancer Res. 44: 2807-2812; Schwartz, E. L., Brown, B. J., Nierenberg, M., Marsh, J. C., and Sartorelli, A. C. (1983) Cancer Res. 43: 2725-2730; Sugano, H., Furusawa, M., Kawaguchi, T., and Ikawa, Y. (1973) Bibl. Hematol. 39: 943-954; Ebert, P. S., Wars, I., and Buell, D. N. (1976) Cancer Res. 36: 1809-1813; Hayashi, M., Okabe, J., and Hozumi, M. (1979) Gann 70: 235-238), The combination of the pharmaceutical compositions of this invention and any of the anti-cancer agents described above and their use thereof, are within the scope of the present invention.

Methods of Treatment

The present invention also provides a method of treating a patient having a tumor characterized by proliferation of neoplastic cells which comprises administering to the patient an effective amount of any of the compositions of the present invention above, effective to selectively induce terminal differentiation of such neoplastic cells and thereby inhibit their proliferation.

The method of the present invention is intended for the treatment of human patients with cancer. However, it is also likely that the method would be effective in the treatment of cancer in other mammals. Cancer includes but is not limited to any cancer caused by the proliferation of neoplastic cells, such as lung cancer, acute lymphoid myeloma, Hodgkins lymphoma, non-Hodgkins lymphoma, bladder melanoma, renal carcinoma, breast carcinoma, prostate carcinoma, ovarian carcinoma or colorectal carcinoma.

The invention is illustrated in the examples in the Experimental Details Section which follows. This section is set forth to aid in an understanding of the invention but is not intended to, and should not be construed to limit in any way the invention as set forth in the claims which follow thereafter.

EXPERIMENTAL DETAILS SECTION

Example 1

Synthesis of SAHA Form I

SAHA Form I can be synthesized according to the method outlined below, or by any modification and variants thereof.

Synthesis of SAHA

Step 1—Synthesis of Suberanilic Acid

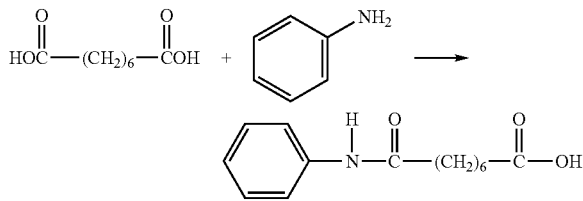

In a 22 L flask was placed 3,500 g (20.09 moles) of suberic acid, and the acid melted with heat. The temperature was raised to 175° C., and then 2,040 g (21.92 moles) of aniline was added. The temperature was raised to 190° C. and held at that temperature for 20 minutes. The melt was poured into a Nalgene tank that contained 4,017 g of potassium hydroxide dissolved in 50 L of water. The mixture was stirred for 20 minutes following the addition of the melt. The reaction was repeated at the same scale, and the second melt was poured into the same solution of potassium hydroxide. After the mixture was thoroughly stirred, the stirrer was turned off, and the mixture was allowed to settle. The mixture was then filtered through a pad of Celite (4,200 g) (the product was filtered to remove the neutral by-product (from attack by aniline on both ends of suberic acid). The filtrate contained the salt of the product, and also the salt of unreacted suberic acid. The mixture was allowed to settle because the filtration was very slow, taking several days.). The filtrate was acidified using 5 L of concentrated hydrochloric acid; the mixture was stirred for one hour, and then allowed to settle overnight. The product was collected by filtration, and washed on the funnel with deionized water (4×5 L). The wet filter cake was placed in a 72 L flask with 44 L of deionized water, the mixture heated to 50° C., and the solid isolated by a hot filtration (the desired product was contaminated with suberic acid which has a much greater solubility in hot water. Several hot triturations were done to remove suberic acid. The product was checked by NMR [$D_6$DMSO] to monitor the removal of suberic acid). The hot trituration was repeated with 44 L of water at 50° C. The product was again isolated by filtration, and rinsed with 4 L of hot water. It was dried over the weekend in a vacuum oven at 65° C. using a Nash pump as the vacuum source (the Nash pump is a liquid ring pump (water) and pulls a vacuum of about 29 inch of mercury. An intermittent argon purge was used to help carry off water); 4,182.8 g of suberanilic acid was obtained.

The product still contained a small amount of suberic acid; therefore the hot trituration was done portionwise at 65° C., using about 300 g of product at a time. Each portion was filtered, and rinsed thoroughly with additional hot water (a total of about 6 L). This was repeated to purify the entire batch. This completely removed suberic acid from the product. The solid product was combined in a flask and stirred with 6 L of methanol/water (1:2), and then isolated by filtration and air dried on the filter over the week end. It was placed in trays and dried in a vacuum oven at 65° C. for 45 hours using the Nash pump and an argon bleed. The final product has a weight of 3,278.4 g (32.7% yield).

Step 2 Synthesis of Methyl Suberanilate

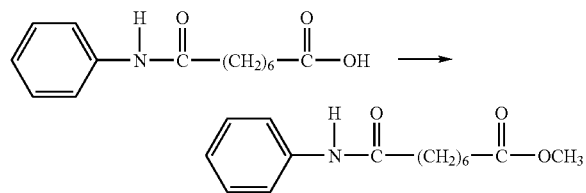

To a 50 L flask fitted with a mechanical stirrer, and condenser was placed 3,229 g of suberanilic acid from the previous step, 20 L of methanol, and 398.7 g of Dowex 50WX2-400 resin. The mixture was heated to reflux and held at reflux for 18 hours. The mixture was filtered to remove the resin beads, and the filtrate was taken to a residue on a rotary evaporator.

The residue from the rotary evaporator was transferred into a 50 L flask fitted with a condenser and mechanical stirrer. To the flask was added 6 L of methanol, and the mixture heated to give a solution. Then 2 L of deionized water was added, and the heat turned off. The stirred mixture was allowed to cool, and then the flask was placed in an ice bath, and the mixture cooled. The solid product was isolated by filtration, and the filter cake was rinsed with 4 L of cold methanol/water (1:1). The product was dried at 45° C. in a vacuum oven using a Nash pump for a total of 64 hours to give 2,850.2 g (84% yield) of methyl suberanilate, CSL Lot #98-794-92-3 1.

To a 50 L flask with a mechanical stirrer, thermocouple, and inlet for inert atmosphere was added 1,451.9 g of hydroxylamine hydrochloride, 19 L of anhydrous methanol, and a 3.93 L of a Step 3—Synthesis of Crude SAHA

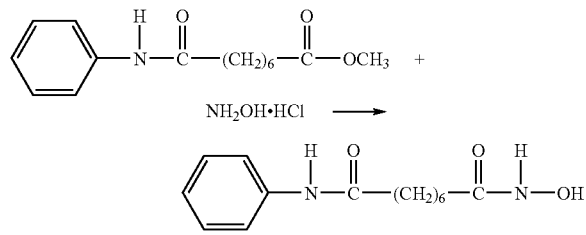

30% sodium methoxide solution in methanol. The flask was then charged with 2,748.0 g of methyl suberanilate, followed by 1.9 L of a 30% sodium methoxide solution in methanol. The mixture was allowed to stir for 16 hr and 10 minutes. Approximately one half of the reaction mixture was transferred from the reaction flask (flask 1) to a 50 L flask (flask 2) fitted with a mechanical stirrer. Then 27 L of deionized water was added to flask 1 and the mixture was stirred for 10 minutes. The pH was taken using a pH meter; the pH was 11.56. The pH of the mixture was adjusted to 12.02 by the addition of 100 ml of the 30% sodium methoxide solution in methanol; this gave a clear solution (the reaction mixture at this time contained a small amount of solid. The pH was adjusted to give a clear solution from which the precipitation the product would be precipitated). The reaction mixture in flask 2 was diluted in the same manner; 27 L of deionized water was added, and the pH adjusted by the addition of 100 ml of a 30% sodium methoxide solution to the mixture, to give a pH of 12.01 (clear solution).

The reaction mixture in each flask was acidified by the addition of glacial acetic acid to precipitate the product. Flask 1 had a final pH of 8.98, and Flask 2 had a final pH of 8.70. The product from both flasks was isolated by filtration using a Buchner funnel and filter cloth. The filter cake was washed with 15 L of deionized water, and the funnel was covered and the product was partially dried on the funnel under vacuum for 15.5 hr. The product was removed and placed into five glass trays. The trays were placed in a vacuum oven and the product was dried to constant weight. The first drying period was for 22 hours at 60° C. using a Nash pump as the vacuum source with an argon bleed. The trays were removed from the vacuum oven and weighed. The trays were returned to the oven and the product dried for an additional 4 hr and 10 minutes using an oil pump as the vacuum source and with no argon bleed. The material was packaged in double 4-mill polyethylene bags, and placed in a plastic outer container. The final weight after sampling was 2633.4 g (95.6%).

Step 4—Preparation of SAHA Form I by Recrystallization of Crude SAHA

The crude SAHA was recrystallized from methanol/water. A 50 L flask with a mechanical stirrer, thermocouple, condenser, and inlet for inert atmosphere was charged with the crude SAHA to be crystallized (2,525.7 g), followed by 2,625 ml of deionized water and 15,755 ml of methanol. The material was heated to reflux to give a solution. Then 5,250 ml of deionized water was added to the reaction mixture. The heat was turned off, and the mixture was allowed to cool. When the mixture had cooled sufficiently so that the flask could be safely handled (28° C.), the flask was removed from the heating mantle, and placed in a tub for use as a cooling bath. Ice/water was added to the tub to cool the mixture to −5° C. The mixture was held below that temperature for 2 hours. The product was isolated by filtration, and the filter cake washed with 1.5 L of cold methanol/water (2:1). The funnel was covered, and the product was partially dried under vacuum for 1.75 hr. The product was removed from the funnel and placed in 6 glass trays. The trays were placed in a vacuum oven, and the product was dried for 64.75 hr at 60° C. using a Nash pump as the vacuum source, and using an argon bleed. The trays were removed for weighing, and then returned to the oven and dried for an additional 4 hours at 60° C. to give a constant weight. The vacuum source for the second drying period was a oil pump, and no argon bleed was used. The material was packaged in double 4-mill polyethylene bags, and placed in a plastic outer container. The final weight after sampling was 2,540.9 g (92.5%).

In other experiments, crude SAHA was crystallized using the following conditions:

TABLE 1

SAHA Crystallization Conditions

| Solvent | Water | Agitation | Time (hr) |
|---|---|---|---|
| Methanol | — | Off | 2 |
| Methanol | — | On | 72 |
| Ethanol | — | On | 72 |
| Isopropanol | — | Off | 72 |
| Ethanol | 15% | On | 2 |
| Methanol | 15% | Off | 72 |
| Ethanol | 15% | Off | 72 |
| Ethanol | 15% | On | 72 |
| Methanol | 15% | On | 72 |

All these reaction conditions produced SAHA Polymorph I.

Example 1A

Production of SAHA Form I

Step 1 8-anilino-8-oxooctanoic acid; suberanilic acid (Compound 3)

Suberic acid (Compound 1, 174.2 g, 1.0 mole), aniline (Compound 2, 85.8-94.9 g), and toluene (0.1-0.2 L) are combined, heated to reflux and refluxed for a minimum of 60 hours. The reaction is quenched at reflux by adjusting the pH to $\geq$11 with 10% sodium hydroxide solution. The aqueous phase is separated. The organic layer is combined with toluene (0.11-0.13 L) and water (0.3-0.4 L), and the aqueous layer is separated. The aqueous layers from the extractions and toluene (0.11-0.13 L) are combined, settled, and then separated. The aqueous layer is extracted twice with toluene (0.2-0.3 L) at 60-70° C. The aqueous layer is adjusted at 20-30° C. to a pH of 5.8-6.2, using hydrochloric acid and 10% sodium hydroxide solution as needed. The batch is filtered, washed with chilled water (0.2-0.3 L) and then washed with chilled isopropanol. The wet cake is dried at a maximum of 65° C. under vacuum to yield suberanilic acid.

Step 2 methyl 8-anilino-8-oxooctanoate; methyl suberanilate (Compound 4)

Suberanilic acid (Compound 3, 249.3 g, 1.0 mole) and methanol (0.4-0.5 L) are combined and heated to 45-55° C. The pH is adjusted to $\leq$2 using hydrochloric acid, and the batch temperature is maintained at 45-55° C. until the reaction is complete. The reaction is quenched with deionized water (0.1-0.2 L). The batch is cooled to 25-30° C. and seeded to induce crystallization, and then cooled to 0-10° C. The batch is filtered, and the cake washed with a 50:50 (v/v) methanol/water solution (0.28-0.34 L) at 0-10° C. The wet cake is dried at a maximum of 46° C. under vacuum to yield methyl suberanilate.

Step 3 N-hydroxy-N'-phenyloctanediamide; vorinostat (Compound 5)

Methyl suberanilate (Compound 4, 263.3 g, 1.0 mole) and 2M hydroxylamine freebase solution (0.8-1.0 L) are combined. While maintaining the batch at a maximum of 20° C., the apparent pH is adjusted to $\geq$10.5 with sodium methoxide in methanol as needed. While maintaining the batch at maximum 20° C. and apparent pH $\geq$10.5 using sodium methoxide in methanol, the batch is aged. During the age, hydroxylamine freebase solution (0.5-0.6 L) is added, and the batch is maintained at maximum 20° C. and apparent pH $\geq$10.5 until the reaction is complete. The reaction is quenched by adding the batch to water (0.9-1.1 L) while maintaining the batch temperature between 20-35° C., and the water content of the batch is adjusted to 35-45%. The pH is adjusted to 8.8-9.2 using glacial acetic acid and sodium carbonate as needed. The batch is cooled to 0-10° C. over 5-10 hours. The batch is filtered and the cake washed with 55:45 (v/v) methanol/water (0.45-0.6 L) at 0-10° C. The wet cake is vacuum conditioned until the water content is $\leq$35%.

The vorinostat crude (264.32 g, 1.0 mole) wet cake is combined with denatured ethanol (1308-1599 g) and water (167-204 g). Hydroxylamine hydrochloride (>9 mEquiv) and sodium methoxide in methanol (>9 mEquiv) are added to the slurry, and the batch is heated to 70-80° C. The solution is filtered and then crystallized by slowly cooling to 0-10° C. The batch is filtered and the cake washed with cold 4:1 (v/v) denatured ethanol/water. The wet cake is dried at a maximum of 45° C. under vacuum.

Step 4 N-hydroxy-N'-phenyloctanediamide-vorinostat-fine (Compound 6)

Vorinostat (Compound 5, 264.3 g, 1.0 mole) is slurried in a 50:50 (v/v) ethanol/water solution (minimum 2.8 L). The vorinostat slurry is wet-milled to a mean size of 25-45 μm while maintaining the batch temperature at 7-30° C. The final slurry is filtered and the wet cake is washed with 0-40° C. water (minimum 0.8 L). The wet cake is dried at a maximum of 55° C. under vacuum to a maximum water content of 0.2% (w/w) to yield vorinostat-fine drug substance.

Step 5 N-hydroxy-N'-phenyloctanediamide-vorinostat-coarse (Compound 7)

Vorinostat (Compound 5, 264.3 g, 1.0 mole) is slurried in a 50:50 (v/v) ethanol/water solution (4.9-5.5 L). Under a minimum of 15 psig pressure, the slurry is heated to 65-70° C. to dissolve and then cooled to 60-64° C. A seed slurry is transferred into the batch while maintaining the batch temperature. The batch is aged for a minimum of 2 hours at 61-63° C. The batch is cooled in three steps by controlling the jacket temperature: (1) to 55° C. at 0.35-0.78° C./hour, (2) to 45° C. at 0.83-2.00° C./hour, and (3) to −5 to 25° C. at 2.00-4.44° C./hour. The final slurry is aged at −5 to 25° C. for about 1 hour and then filtered. The wet cake is washed with water (minimum 0.8 L). The wet cake is dried at a maximum of 55° C. under vacuum to yield vorinostat-fine drug substance.

The seed slurry is prepared by combining vorinostat-fine dry cake (97.8-116.3 g, 0.37-0.44 mol) and 50:50 (v/v) ethanol/water solution (1.0-1.2 L). Under a minimum of 15 psig pressure, the seed slurry is heated to 62-66° C., aged for about 0.5 hours and then cooled to 60-64° C.

Example 2

Generation of Wet-Milled Small Particles in 1:1 Ethanol/Water

The SAHA Polymorph I crystals were suspended in 1:1 (by volume) EtOH/water solvent mixture at a slurry concentration ranging from 50 mg/gram to 150 mg/gram (crystal/solvent mixture). The slurry was wet milled with IKA-Works Rotor-Stator high shear homogenizer model T50 with superfine blades at 20-30 m/s, until the mean particle size of SAHA was less than 50 μm and 95% less than 100 μm, while maintaining the temperature at room temperature. The wet-milled slurry was filtered and washed with the 1:1 EtOH/water solvent mixture at room temperature. The wet cake was then dried at 40° C. The final mean particle size of the wet-milled material was less than 50 μm as measured by the Microtrac method below.

Particle size was analyzed using an SRA-150 laser diffraction particle size analyzer, manufactured by Microtrac Inc. The analyzer was equipped with an ASVR (Automatic Small Volume Recirculator). 0.25 wt % lecithin in ISOPAR G was used as the dispersing fluid. Three runs were recorded for each sample and an average distribution was calculated. Particle size distribution (PSD) was analyzed as a volume distribution. The mean particle size and 95%<values based on volume were reported.

Example 2A

Large Scale Generation of Wet-Milled Small Particles in 1:1 Ethanol/Water 56.4 kg SAHA Polymorph I crystals were charged to 610 kg (10.8 kg solvent per kg SAHA) of a 50% vol/vol solution of 200 proof punctilious ethanol and water ("50/50 EtOH/Water") at 20-25° C. The slurry (~700 L) was recirculated through an IKA Works wet-mill set with super-fine generators until reaching a steady-state particle size distribution. The conditions were: DR3-6, 23 m/s rotor tip speed, 30-35 Lpm, 3 gen, ~70 turnovers (a turnover is one batch volume passed through one gen).

Approx. Mill Time (hr) =
$$\frac{70 \times \text{Batch Volume}(L)}{\text{Natural Draft of Mill}(Lpm) \times \# \text{ of Generators} \times 60}$$

The wet cake was filtered, washed with water (total 3 kg/kg, ~170 kg) and vacuum dried at 40-45° C. The dry cake was then sieved (595 μm screen) and packed as the "Fine API".

Example 3

Growth of Large Crystals of Mean Particle Size 150 μm in 1:1 Ethanol/Water 25 grams of SAHA Polymorph I crystals and 388 grams of 1:1 Ethanol/water solvent mixture were charged into a 500 ml jacketed resin kettle with a glass agitator. The slurry was wet milled to a particle size less than 50 μm at room temperature following the steps of Example 2. The wet-milled slurry was heated to 65° C. to dissolve ~85% of the solid. The heated slurry was aged at 65° C. for 1-3 hours to establish a ~15% seed bed. The slurry was mixed in the resin kettle under 20 psig pressure, and at an agitator speed range of 400-700 rpm.

The batch was then cooled slowly to 5° C.: 65 to 55° C. in 10 hours, 55 to 45° C. in 10 hours, 45 to 5° C. in 8 hours. The cooled batch was aged at 5° C. for one hour to reach a target supernatant concentration of less than 5 mg/g, in particular, 3 mg/g. The batch slurry was filtered and washed with 1:1 EtOH/water solvent mixture at 5° C. The wet cake was dried at 40° C. under vacuum. The dry cake had a final particle size of ~150 μm with 95% particle size <300 μm according to the Microtrac method.

Example 3A

Growth of Large Crystals in 1:1 Ethanol/Water 13.4 kg vorinostat and 134 kg of a 1:1 (v/v) solution of ethanol and water are combined. The resulting slurry is wet-milled to a mean size of 95%<100 μm. An additional 20 kg of the 1:1 solution is added and the batch is heated under 20 psig nitrogen pressure to 69-71° C. and aged for 3 hours to establish a seed bed. While maintaining 20 psig pressure, the batch is cooled to 64-66° C. over 8 hours; to 59-61° C. over 4 hours; to 49-51° C. over 4 hours; then to 14-16° C. over 6 hours. The batch is filtered and the cake is washed with a total of approximately 80 kg water. The batch is vacuum dried at maximum of 55° C.

Example 4

Growth of Large Crystals with Mean Particle Size of 140 μm in 1:1 Ethanol/Water 7.5 grams of SAHA Polymorph I crystals and 70.7 grams of 1:1 EtOH/water solvent mixture were charged into a seed preparation vessel (500-ml jacketed resin kettle). The seed slurry was wet milled to a particle size less than 50 μm at room temperature following the steps of Example 2 above. The seed slurry was heated to 63-67° C. and aged over 30 minutes to 2 hours.

In a separate crystallizer (1-liter jacketed resin kettle), 17.5 grams of SAHA Polymorph I crystals and 317.3 grams of 1:1 EtOH/water solvent mixture were charged. The crystallizer was heated to 67-70° C. to dissolve all solid SAHA crystals first, and then was cooled to 60-65° C. to keep a slightly supersaturated solution.

The seed slurry from the seed preparation vessel was transferred to the crystallizer. The slurry was mixed in the resin kettle under 20 psig pressure, and at an agitator speed range similar to that in Example 3. The batch slurry was cooled slowly to 5° C. according to the cooling profile in Example 3. The batch slurry was filtered and washed with 1:1 EtOH/water solvent mixture at 5° C. The wet cake was dried at 40° C. under vacuum. The dry cake had a final particle size of about 140 μm with 95% particle size <280 μm.

Example 4A

Large Scale Growth of Large Crystals in 1:1 Ethanol/Water 21.7 kg of the "Fine API" dry cake from Example 2A (28.6% of total, 0.40 Equiv. w.r.t basis) and 213 kg of 50/50 EtOH/Water solution (3.93 kg solvent/kg SAHA basis) was charged to Vessel #1—the Seed Preparation Tank. 54.2 kg of SAHA Polymorph I crystals (71.4% of total, 1.00 Equiv, Basis) and 990 kg 50/50 EtOH/Water (18.24 kg solvent/kg SAHA basis) was charged to Vessel #2—the Crystallizer. The Crystallizer was pressurized to 20-25 psig and the contents heated to 67-70° C. while maintaining the pressure to fully dissolve the crystalline SAHA. The contents were then cooled to 61-63° C. to supersaturate the solution. During the aging process in the Crystallizer, the Seed Prep Tank was pressurized to 20-25 psig, the seed slurry was heated to 64°

C., aged for 30 minutes while maintaining the pressure to dissolve ~½ of the seed solids, and then cooled to 61-63° C.

The hot seed slurry was rapidly transferred from the Seed Prep Tank to the Crystallizer (no flush) while maintaining both vessel temperatures. The nitrogen pressure in the Crystallizer was re-established to 20-25 psig and the batch was aged for 2 hours at 61-63° C. The batch was cooled to 5° C. in three linear steps over 26 hours: (1) from 62° C. to 55° C. over 10 hours; (2) from 55° C. to 45° C. over 6 hours; and (3) from 45° C. to 5° C. over 10 hours. The batch was aged for 1 hr and then the wet cake was filtered and washed with water (total 3 kg/kg SAHA, ~163 kg), and vacuum dried at 40-45° C. The dry cake from this recrystallization process is packed-out as the "Coarse API". Coarse API and Fine API were blended at a 70/30 ratio.

SAHA Polymorph I crystals in the Crystallizer can be prepared by adding 8.7 kg SAHA to 72 kg of a 9:1 (v/v) solution of ethanol and water. 25 g of hydroxylamine hydrochloride is charged followed by 350 g of a 1N aqueous solution of sodium hydroxide. The resulting slurry is heated to 69.5-71.5° C. and aged for 45 minutes to dissolve the batch and reduce the levels of the O-suberanilic SAHA impurity. The batch is cooled to 4° C. over 2 hours and aged at 0-10° C. for 2 hrs. The batch is filtered and the cake is washed with a total of approximately 60 kg water. The batch is vacuum dried at maximum of 55° C. to produce 8.0 kg of vorinostat.

Example 5

Generation of Wet-Milled Small Particles Batch 288

SAHA Polymorph I crystals were suspended in ethanolic aqueous solution (100% ethanol to 50% ethanol in water by volume) at a slurry concentration ranging from 50 mg/gram to 150 mg/gram (crystal/solvent mixture). The slurry was wet milled with IKA-Works Rotor-Stator high shear homogenizer model T50 with superfine blades at 20-35 m/s, until the mean particle size of SAHA was less than 50 µm and 95% less than 100 µm, while maintaining the temperature at room temperature. The wet-milled slurry was filtered and washed with EtOH/water solvent mixture at room temperature. The wet cake was then dried at 40° C. The final mean particle size of the wet-milled material was less than 50 µm as measured by the Microtrac method as described before.

Example 6

Growth of Large Crystals Batch 283

24 grams of SAHA Polymorph I crystals and 205 ml of 9:1 Ethanol/water solvent mixture were charged into a 500 ml jacketed resin kettle with a glass agitator. The slurry was wet milled to a particle size less than 50 µm at room temperature following the steps of Example 1. The wet-milled slurry was heated to 65° C. to dissolve ~85% of the solid. The heated slurry was aged at 64-65° C. for 1-3 hours to establish a ~15% seed bed. The slurry was mixed at an agitator speed range of 100-300 rpm.

The batch was then cooled to 20° C. with one heat-cool cycle: 65° C. to 55° C. in 2 hours, 55° C. for 1 hour, 55° C. to 65° C. over ~30 minutes, age at 65° C. for 1 hour, 65° C. to 40° C. in 5 hours, 40° C. to 30° C. in 4 hours, 30° C. to 20° C. over 6 hours. The cooled batch was aged at 20° C. for one hour. The batch slurry was filtered and washed with 9:1 EtOH/water solvent mixture at 20° C. The wet cake was dried at 40° C. under vacuum. The dry cake had a final particle size of ~150 µm with 95% particle size <300 µm per Microtrac method.

Example 7

X-Ray Powder Diffraction Analysis

X-ray Powder Diffraction analysis was performed on SAHA Form I obtained in accordance with Examples 1-6, and on SAHA Form II-V prepared by methods detailed in Table 2 below.

TABLE 2

SAHA Samples analyzed by X-ray Powder Diffraction

| SAHA Sample | Reference | Method |
| --- | --- | --- |
| SAHA Form I | — | Examples 1-6 |
| SAHA Form II | U.S. Pat. No. 5,369,108 Columns 25-26 Procedures A, C, D | SAHA was dissolved in EtOAc/THF (3/1). The solutions were passed through a plug of silica gel using EtOAc/THF (3/1). Fractions were collected and concentrated. The solid appeared pink. |
| SAHA Form III | U.S. Pat. No. 5,369,108 Columns 25-26 Procedure B | SAHA was dissolved in methanol, filtered via celite, and concentrated on the rotovap to dryness. The residues were slurried with hexanes and filtered. The solids appeared pink. |
| SAHA Form IV | Mai et al OPPI Briefs (2001)Vol 33(4), 391-394 | SAHA was recrystallized from acetonitrile. |
| SAHA Form V | Stowell et al J. Med. Chem. (1995), 38(8), 1411-1413 | To a mixture of SAHA (4.0 g) in anhydrous methanol (15 mL) was added NaOMe (10.7 mL, 4.37 M, 47 mmol). The solution became homogeneous, but solid formed after about 5 minutes. The mixture was stirred for 15 min, and then 100 ml of water was added followed by slow addition of glacial acetic acid (3.77 mL, 4.0 g). The crystalline solid was collected and washed with water (2 × 75 mL). The solid was dried under high vaccum overnght yielding 3.85 g (96% recovery) of an off-white solid. |

X-Ray Diffraction Analysis:

The samples were analyzed on a Siemens D500 Automated Powder Diffractometer (Instrument ID No. LD-301-4), which is operated according to Standard Operating Procedure EQ-27, Rev. 12, in accordance with the manufacturer's instructions. The Diffractometer is equipped with a graphite monochromator and a Cu ($\lambda$=1.54 Å) X-ray source operated at 50 kV, 40 mA. Two-theta calibration is performed using an NBS mica standard (SRM675). The samples were analyzed using the following instrument parameters:

Measuring Range: 4-40 2 theta
Step Width: 0.05 Å
Measuring Time per Step: 1.2 seconds Sample preparation was performed according to Standard Operating Procedure MIC-7, Rev. 2 (Section 3.1.2), in accordance with the manufacturer's instructions, using a zero background sample plate (#1). The samples were processed following a light mortar and pestle grind to ensure homogeneity.

FIG. 7A-E depicts the X-ray diffractograms for SAHA Forms I-V. The corresponding data for the X-ray diffractograms is presented in Tables 3-7 below:

TABLE 3

SAHA Form I

| Peak | 2Theta (deg) | D (Å) |
|---|---|---|
| 1 | 8.97 | 9.86159 |
| 2 | 9.37 | 9.43 |
| 3 | 17.46 | 5.07 |
| 4 | 19.41 | 4.57 |
| 5 | 20.04 | 4.43 |
| 6 | 23.96 | 3.71 |
| 7 | 24.44 | 3.64 |
| 8 | 24.76 | 3.59 |
| 9 | 24.96 | 3.56 |
| 10 | 27.96 | 3.19 |
| 11 | 43.29 | 2.08 |

TABLE 4

SAHA Form II

| Peak | 2Theta (deg) | D (Å) |
|---|---|---|
| 1 | 5.12 | 17.24 |
| 2 | 5.46 | 16.15 |
| 3 | 7.48 | 11.8 |
| 4 | 7.72 | 11.44 |
| 5 | 8.15 | 18.84 |
| 6 | 8.72 | 10.13 |
| 7 | 9.21 | 9.59 |
| 8 | 10.91 | 8.09 |
| 9 | 12.38 | 7.14 |
| 10 | 13.55 | 6.52 |
| 11 | 17.31 | 5.12 |
| 12 | 18.22 | 4.86 |
| 13 | 18.86 | 4.70 |
| 14 | 19.32 | 4.59 |
| 15 | 19.88 | 4.46 |
| 16 | 20.76 | 4.27 |
| 17 | 21.20 | 4.19 |
| 18 | 21.72 | 4.09 |
| 19 | 22.07 | 4.02 |
| 20 | 22.88 | 3.88 |
| 21 | 23.36 | 3.80 |
| 22 | 23.79 | 3.73 |
| 23 | 24.16 | 3.68 |
| 24 | 24.66 | 3.61 |
| 25 | 25.75 | 3.46 |

TABLE 4-continued

SAHA Form II

| Peak | 2Theta (deg) | D (Å) |
|---|---|---|
| 26 | 26.92 | 3.31 |
| 27 | 27.56 | 3.23 |
| 28 | 27.88 | 3.20 |
| 29 | 28.53 | 3.12 |
| 30 | 30.68 | 2.91 |
| 31 | 40.21 | 2.24 |
| 32 | 42.80 | 2.11 |
| 33 | 43.16 | 2.09 |

TABLE 5

SAHA Form III

| Peak | 2Theta (deg) | D (Å) |
|---|---|---|
| 1 | 10.10 | 8.75 |
| 2 | 12.13 | 7.29 |
| 3 | 13.83 | 6.40 |
| 4 | 15.11 | 5.86 |
| 5 | 17.65 | 5.02 |
| 6 | 18.54 | 4.78 |
| 7 | 18.80 | 4.71 |
| 8 | 19.60 | 4.52 |
| 9 | 20.18 | 4.40 |
| 10 | 20.90 | 4.25 |
| 11 | 21.69 | 4.10 |
| 12 | 23.81 | 3.73 |
| 13 | 24.54 | 3.62 |
| 14 | 25.04 | 3.55 |
| 15 | 25.36 | 3.51 |
| 16 | 26.10 | 3.41 |
| 17 | 26.80 | 3.32 |
| 18 | 35.62 | 2.51 |
| 19 | 37.12 | 2.42 |
| 20 | 40.92 | 2.20 |
| 21 | 42.43 | 2.13 |
| 22 | 44.83 | 2.02 |

TABLE 6

SAHA Form IV

| Peak | 2Theta (deg) | D (Å) |
|---|---|---|
| 1 | 8.84 | 9.99 |
| 2 | 9.25 | 9.55 |
| 3 | 11.00 | 8.04 |
| 4 | 12.44 | 7.11 |
| 5 | 17.38 | 5.10 |
| 6 | 19.37 | 4.58 |
| 7 | 19.93 | 4.45 |
| 8 | 22.36 | 3.97 |
| 9 | 22.89 | 3.88 |
| 10 | 23.83 | 3.73 |
| 11 | 24.24 | 3.67 |
| 12 | 24.80 | 3.59 |
| 13 | 25.80 | 3.45 |
| 14 | 26.96 | 3.30 |
| 15 | 27.84 | 3.20 |
| 16 | 28.39 | 3.14 |

TABLE 7

SAHA Form V

| Peak | 2Theta (deg) | D (Å) |
|---|---|---|
| 1 | 5.08 | 17.39 |
| 2 | 9.20 | 9.60 |
| 3 | 10.07 | 8.77 |
| 4 | 12.13 | 7.29 |
| 5 | 15.09 | 5.86 |
| 6 | 17.65 | 5.02 |
| 7 | 19.32 | 4.59 |
| 8 | 19.80 | 4.48 |
| 9 | 20.16 | 4.41 |
| 10 | 20.87 | 4.25 |
| 11 | 21.67 | 4.10 |
| 12 | 24.56 | 3.62 |
| 13 | 25.25 | 3.52 |
| 14 | 26.10 | 3.41 |
| 15 | 35.62 | 2.51 |
| 16 | 37.12 | 2.42 |
| 17 | 40.90 | 2.20 |
| 18 | 41.78 | 2.16 |
| 19 | 42.42 | 2.13 |
| 20 | 44.82 | 2.02 |

The X-ray powder diffraction pattern of SAHA Form I was also collected using a X'PERT Pro Phillips X-ray diffractometer with a copper Kα radiation (wavelength 1.542 Å). The prominent 2θ positions along with the d-spacings are summarized in Table 3A.

TABLE 3A

SAHA Form I

| Position [° 2θ] | d-spacing [Å] |
|---|---|
| 9.1 | 9.7 |
| 10.8 | 8.2 |
| 12.3 | 7.2 |
| 17.2 | 5.2 |
| 19.2 | 4.6 |
| 19.8 | 4.5 |
| 23.7 | 3.7 |
| 24.1 | 3.7 |
| 25.7 | 3.5 |
| 26.8 | 3.3 |
| 27.7 | 3.2 |

Example 8

Melting Point Analysis

Melting point analysis was performed on SAHA Form I-V.

TABLE 8

Melting Points

| SAHA Sample | MP (° C.) |
|---|---|
| SAHA Form I | 159-160 |
| SAHA Form II | 152-155 |
| SAHA Form III | 138-144 |
| SAHA Form IV | 158-160.5 |
| SAHA Form V | 159.5-160.5 |

Example 9

Differential Scanning Calorimetric Analysis

Differential Scanning Calorimetric (DSC) analysis was performed on SAHA Form I-V.

Equipment:

Standard Aluminum DSC sample pans and covers used were Perkin Elmer (Part #0219-0041, or equivalent).

Sample Pan Crimper Accessory used was a Perkin Elmer Standard Aluminum Pan Crimper or equivalent.

Differential Scanning Calorimeter used was Perkin Elmer DSC 6 or equivalent.

Micro Balance used was Perkin Elmer AD-4 Autobalance or equivalent.

Software—Pyris or other suitable thermal analysis software.

Differential Scanning Calorimeter Conditions:

| | |
|---|---|
| Purge Gas | Nitrogen (about 20 mL/min) |
| Cooling Agent | Tap water |
| Oven Temp Program | Heat from 50° C. at 10.0° C./minute to at least 30° C. above the observed melting temperature. |

Data Interpretation:

The peak temperature and melting onset temperatures were determined. Peak shapes were observed for any indication that more than one melting temperature is occurring.

The results of multiple samples are summarized in Table 9:

TABLE 9

Differential Scanning Calorimetry

| SAHA Sample | Onset Temp (° C.) | Peak Temp (° C.) |
|---|---|---|
| SAHA Form I | 161.8 | 164.8 |
| | 162.1 | 164.5 |
| | 162.7 | 165.0 |
| | 161.4 | 164.7 |
| | 161.9 | 164.1 |
| | 161.6 | 164.3 |
| | 152.5 | 164.9 |
| | 160.9 | 163.7 |
| | 161.5 | 163.5 |
| | 161.58 | 163.93 |
| SAHA Form II | 156.6 | 160.2 |
| | 158.22, 161.58 (doublet) | 160.39, 162.4 (doublet) |
| SAHA Form III | 110.86, 145.68 (doublet) | 120.11, 147.58 (doublet) |
| | 114.69, 144.41 (doublet) | 122.40, 147.00 (doublet) |
| | 123.67, 148.89 (doublet) | 127.89, 152.22 (doublet) |
| SAHA Form IV | 156.26, 161.64 (doublet) | 160.55, 153.66 (doublet) |
| | 160.46, 164.77 (doublet) | 162.63, 166.55 (doublet) |
| SAHA Form V | 124.47, 162.55 (doublet) | 128.13, 165.14 (doublet) |

Depending upon the rate of heating, i.e. the scan rate, at which the DSC analysis is conducted, the calibration standard used, instrument calibration, the relative humidity and upon the chemical purity, the endotherms of the respective SAHA analyzed may vary. For any given sample, the observed endotherm may also differ from instrument to instrument; however it will generally be within the ranges defined herein provided the instruments are calibrated similarly.

Example 10

Development of Computer Simulation Model

Model Development Procedure

During encapsulation, the SAHA crystals undergo breakage from the pressure of the tamping pins. The first part of the SAHA dissolution and breakage modeling was the development of dissolution and breakage models. Both models were combined for the calculation of the breakage and subsequent dissolution of the broken crystals, and evaluation and optimization of the model parameters for different batches.

The development procedure can be summarized as follows. First, particle size distributions (PSD) and dissolution profiles of the SAHA Form I crystals before encapsulation were measured. The model for dissolution of poly-disperse powders was developed by combining the resistance of intrinsic dissolution [32, 33] and the film resistance [34] for poly-disperse powders and crystals. The dissolution model parameters include the intrinsic dissolution constant and the shape factors of non-spherical crystals. The parameters of the dissolution model were evaluated by fitting the model solutions to the experimental dissolution profile of the SAHA Form I crystals.

Encapsulation of the SAHA crystals with excipients was performed. The density of the capsule content was evaluated for each experimental condition. The dissolution profile of SAHA from capsules was measured. Acceleration of the dissolution was observed as compared to the dissolution of the SAHA crystals before encapsulation. The acceleration of dissolution confirms breakage of the crystals during encapsulation.

The breakage model of the SAHA crystals during encapsulation was developed [35, 36]. The breakage model parameters include the breakage rate constant and the breakage rate exponent. The breakage model was employed for calculation of the PSD after breakage during encapsulation assuming a combination of breakage rate constant and breakage rate exponent. The dissolution model was employed for calculation of the dissolution profile of the broken crystals with the calculated PSD. The computed SAHA dissolution profile was compared with the experimental SAHA dissolution profile for the capsule. The procedure in this paragraph was repeated for different combinations of the breakage rate constants and exponents until an optimum fit was found. The procedure was also repeated for different batches of the SAHA crystals having different PSDs and for different encapsulation conditions.

The optimum dissolution model parameters were found which could satisfactorily describe dissolution of all batches having different PSDs. The parameters were used for prediction of dissolution of both the SAHA crystals before and after encapsulation. The optimum breakage rate exponent was found and could be used in the breakage model for all batches.

Figure 11:
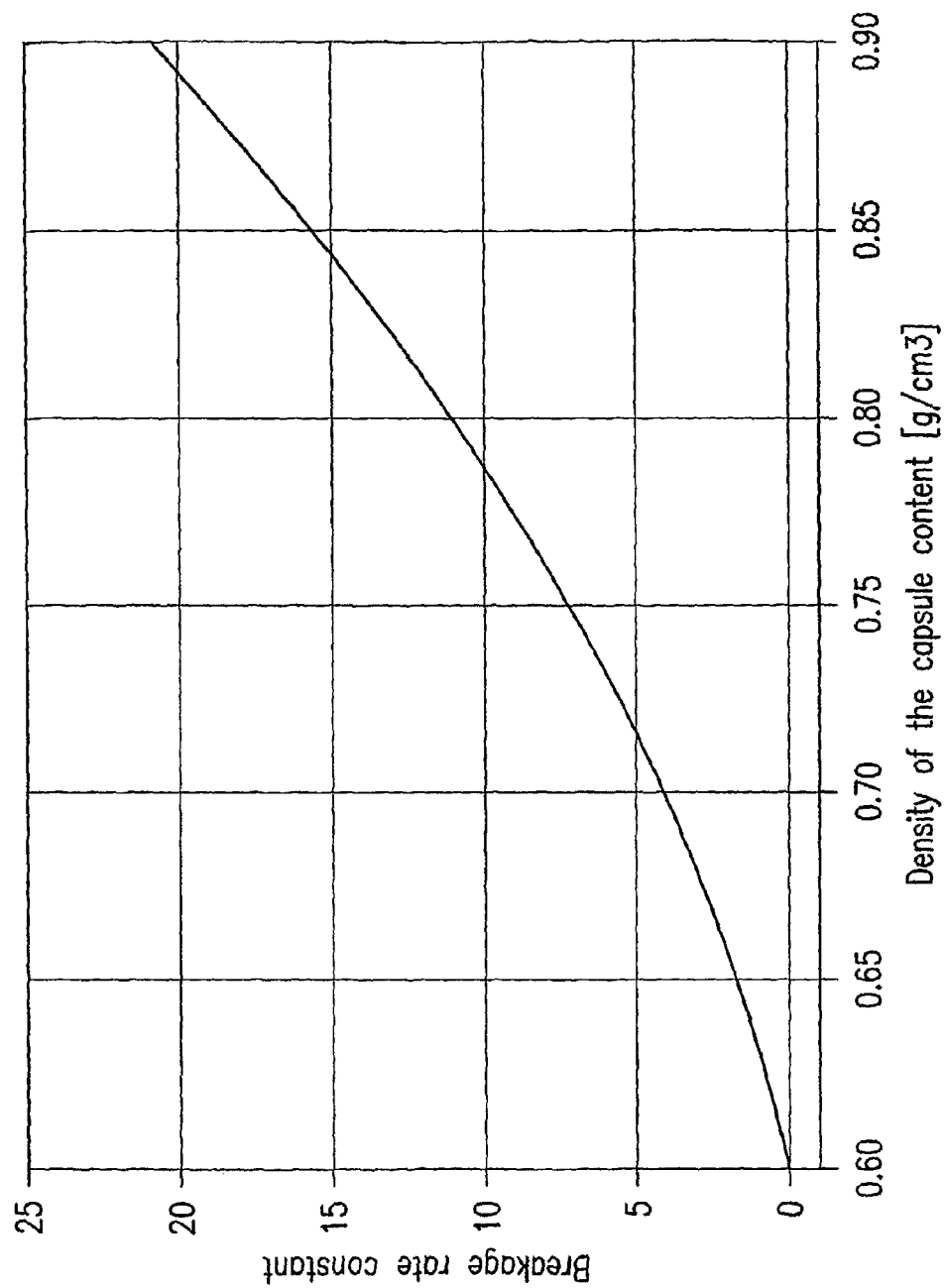
FIG. 11 shows the correlation between breakage rate constant and density of capsule content.

The optimum breakage rate constant for each batch and each encapsulation conditions was related to the capsule density at given encapsulation conditions. A near linear dependence was found between the increasing capsule density and the breakage rate constant for all relevant encapsulation conditions and batches as illustrated in FIG. 11.

Prediction Procedure

After the breakage and dissolution model development and the model parameter optimization, the combined breakage and dissolution model could be used for prediction of the dissolution profiles for new SAHA batches and for the optimization of the encapsulation conditions. The only information needed is the PSD of the new batch.

The prediction procedure can be summarized as follows. First, the PSD of a new batch before encapsulation was measured and capsule density was assumed. The correlation between capsule density and the breakage rate constant was used for calculation of a breakage rate constant.

The computed breakage rate constant together with the optimum breakage rate exponent were introduced into the breakage model to simulate the breakage during encapsulation and a new PSD of broken crystals after encapsulation was computed.

The new PSD was introduced into the dissolution model and the SAHA dissolution profile from a capsule was simulated. The simulated dissolution profile was compared with the target reference profile. The procedure was repeated for a new capsule density until the optimum fit between the simulated profiles and target was found. The optimum capsule density directly determines the optimum encapsulation conditions.

Example 11

Blending of SAHA Crystals

The above prediction procedure can be used for determining the blending ratio of different crystallization batches to obtain a dissolution profile similar to that of the reference.

Optimization of the Blending Ratio of a Large Crystal Batch 283 with a Wet-Milled Crystal Batch 288

Figure 8:
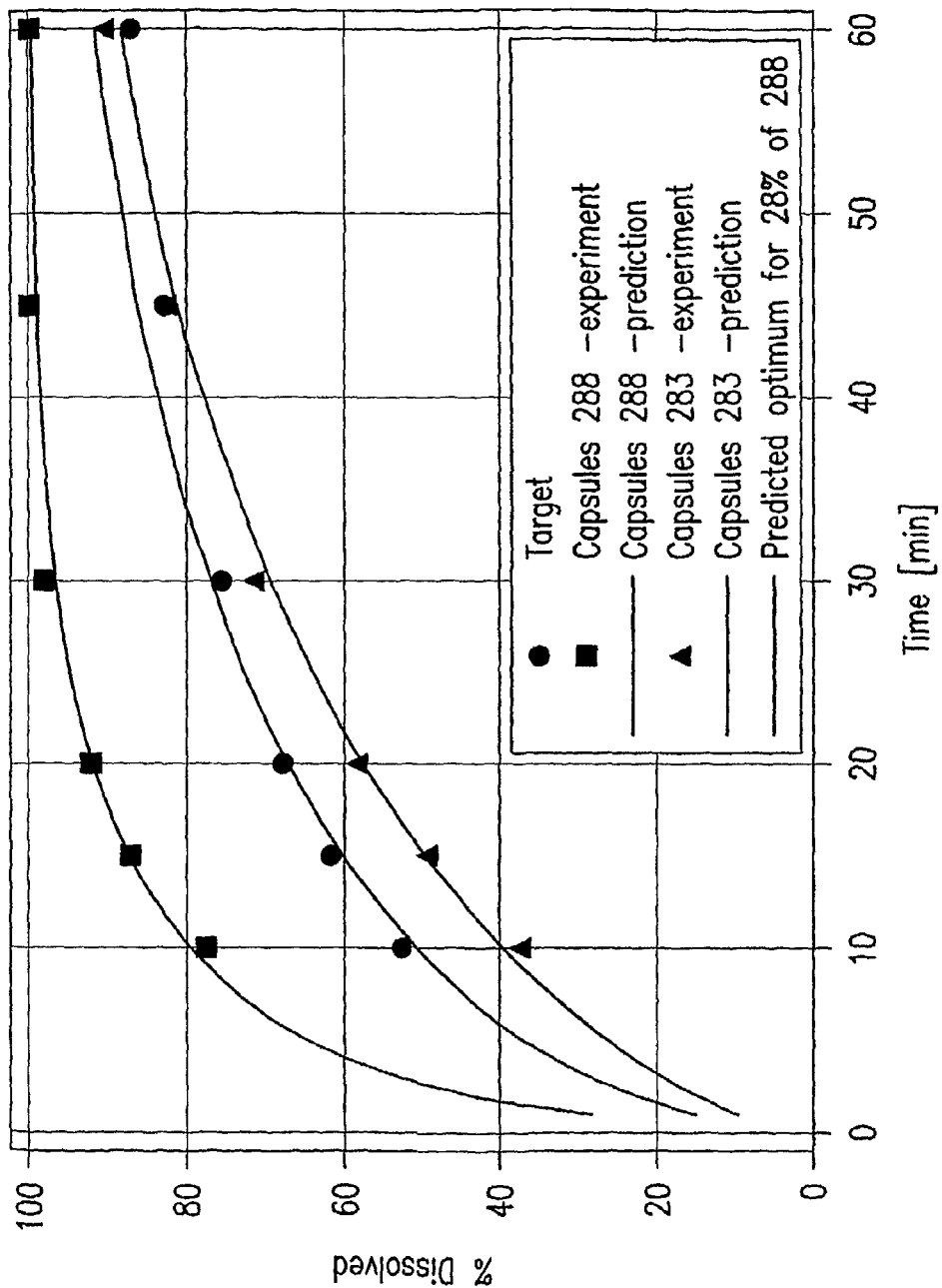
FIG. 8 shows the dissolution profiles predicted by the computer model (curve) and the experimental dissolution profiles (indicated by dots, triangles and squares) for the reference sample (target), capsules 288 and 283.
Figure 9:
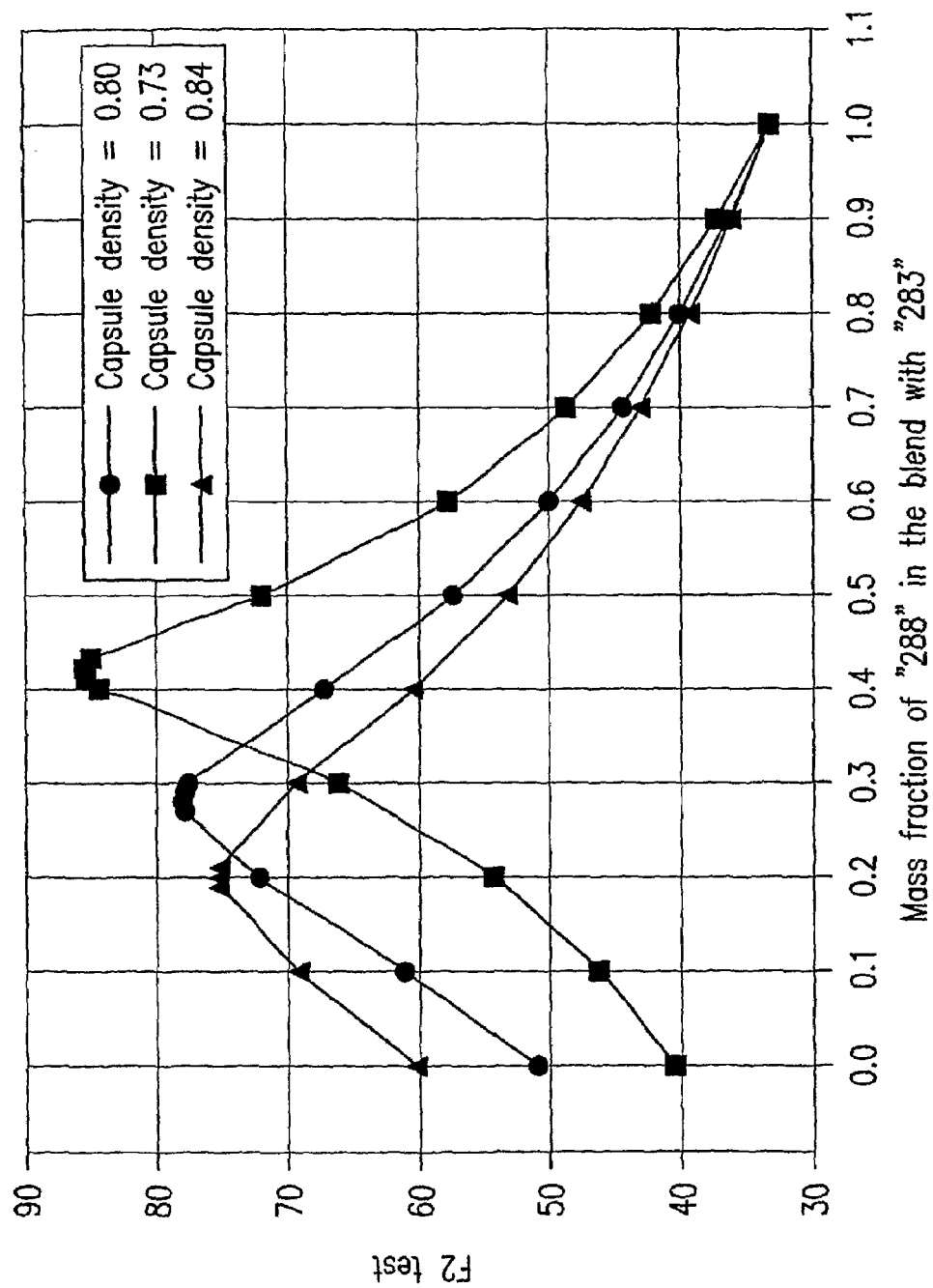
FIG. 9 shows the f2 values in relation to the fraction of API 288 in a blend with API 283 for different capsule densities.

Mathematical models were used for the prediction of the optimal blend of the larger crystal batch 283 with the wet-milled crystal batch 288. First, the goal was to find optimum blends for capsules prepared at given conditions (capsule density) and then to find the most robust blend for different encapsulation conditions. An example of the optimization is shown in FIG. 8 for the capsule density=0.8. The dependence of the predicted F2 values for different capsule densities are shown in FIG. 9. FIG. 9 shows that the predicted F2 test value increases with the decrease of the capsule density (The decrease in capsule density causes a decrease in the extent of breakage). The wet-milled crystals showed little breakage during the encapsulation process. It was concluded that the most robust blend composition (the lowest F2 variation between capsules prepared at different conditions) contained 30% of the batch 288 crystals and 70% of the batch 283 crystals.

Figure 10:
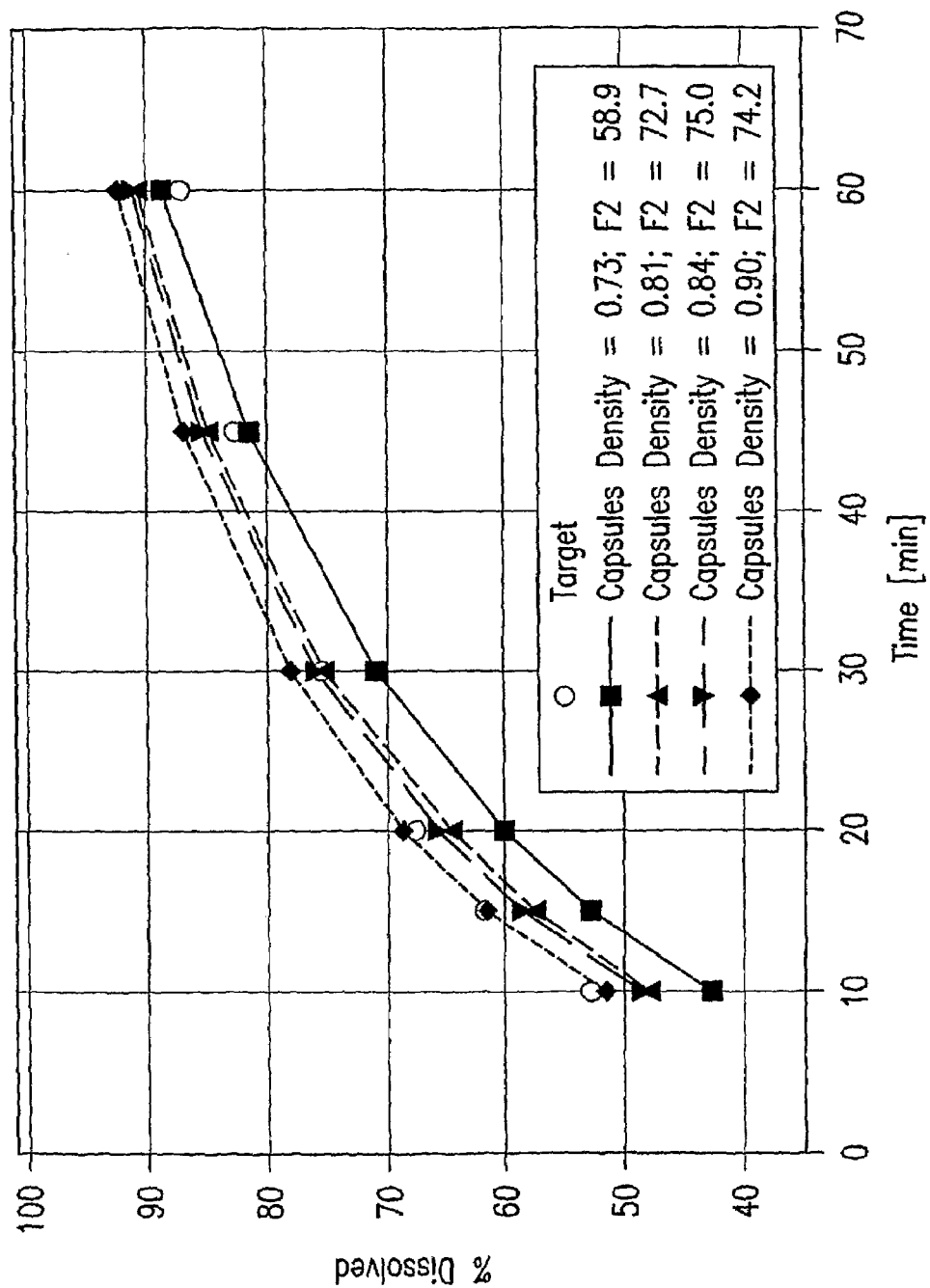
FIG. 10 shows the impact of encapsulation conditions on the SAHA dissolution in capsules made from the blending containing 30% wet-milled API 288 and 70% unmilled API 283.

Experimental dissolution curves for capsules manufactured from the blend containing 30% of the batch 288 crystals and 70% of the batch 283 crystals are presented in FIG. 10.

Blending of Crystallization Batches

A similar computer simulation process can be used for blending SAHA crystals from different crystallization batches. Depending on the particle sizes of the different batch crystals, one would take into account the breakage constant of each batch. Using the computer simulation process above, capsule lot 0683_007A001 was produced by blending 21.2% of batch 1002DRW, 18.0% of batch 1008D, 34.4% of batch 1002E, 10.0% of batch 1004E and 16.4% of batch 1006D.

Batch 1001E and batch 1003E SAHA Polymorph I crystals were blended without the aid of computer simulation, and were blended at a ratio of 2:1 to produce capsule lot 6001.004.

Example 12

Powder Blending of SAHA Crystals

Powder Blending 25.0 Kg of blended SARA Polymorph I crystals were first sieved through a 30 mesh screen (600 μm). The resulting SAHA, 11.1 Kg of Microcrystalline Cellulose (Avicel PH-101), and 1.13 Kg of Croscarmellose Sodium were then loaded into the 141.6 L V-blender, 113 L Tote blender or another comparable sized and type blender. For the V-blender, the resulting material was mixed to homogeneity for approximately 8 minutes at approximately 25 rpm. For the Tote blender, the resulting material was mixed to homogeneity for approximately 17 minutes at approximately 12 rpm.

Powder Blend Lubrication 293.0 g of Magnesium Stearate (vegetable grade) was sieved through a 30 mesh screen (600 μm) and loaded into the V-blender with the blended powder mixture. The resulting mixture was blended to homogeneity for approximately 8 minutes at approximately 25 rpm. 293.0 g of Magnesium Stearate (vegetable grade) was also sieved through a 60 mesh screen (250 μm) and loaded into a tote blender with the blended powder mixture. The resulting mixture was blended to homogeneity for approximately 17 minutes at approximately 12 rpm.

Table 10 summarizes the physical properties of the raw materials in the capsule.

TABLE 10

Physical and Chemical Properties of Raw Materials.

| Raw Material | Physical Property | Value |
| --- | --- | --- |
| Suberoylanilide hydroxamic acid (SAHA) - milled and large crystals | Melting Point (DSC) Solubility: | 161-163° C. |
| | In Water | <0.1 mg/ml |
| | In Methanol | 42 mg/ml |
| | In Ethanol | 0.1 mg/ml |
| | 2% CIP100 aqueous soln. | 11.3 mg/ml |
| | 2% SD-20 aqueous soln. | 0.085 mg/ml |
| Microcrystalline Cellulose (Avicel PH-101) NF, Ph. Eur., JP (FMC BioPolymer) | Nominal Mean Particle Size | 50 μm |
| | Moisture Content | ≤5% |
| | Bulk Density | 0.26-0.31 g/cc |
| Croscarmellose Sodium NF, Ph. Eur., JP (FMC BioPolymer) | Bulk Density | 0.48 g/cc |
| | Tapped Density | 0.67 g/cc |
| | Particle Size Distribution | ≤2% wt. retained on Mesh No. 200 (75 μm) ≤10% wt. retained on Mesh No. 325 (45 μm) |
| Magnesium Stearate (vegetable grade) NF, Ph. Eur., JP (Mallinckrodt Baker Inc.) | Bulk Density | 0.16 g/cc |
| | Particle Size Distribution | ≤2% wt. retained on Mesh No. 200 (75 μm) |
| | Specific Surface Area | 4.2 ± 0.04 m²/g |

Example 13

Encapsulation of SAHA Capsules

Encapsulation/Weight Sorting

The lubed powder mixture was encapsulated using an H&K encapsulator, polished tamping pins or chromium nitride coated tamping pins and size "3" capsules to the desired capsule weight. The filled capsules were polished using a capsule polisher and subsequently weight sorted using a weight sorter to the appropriate weight limit range. Table 11 summarizes the encapsulator settings.

TABLE 11

Summary of Encapsulator Operational Settings

| | |
| --- | --- |
| Dosing Disc | 10.0-12.7 mm |
| Tamping Pins/Station | 3 or 12 |
| Tamping Pin Type | Polished Uncoated or chromium nitride coated |
| Vacuum | ON |
| Encapsulator Speed | 150-270 caps/min or 750-1000 caps/min |

The final SAHA Capsule Composition is illustrated in Table 12. The capsules are weight-sorted using an acceptance limit for capsule weight variation of ±10% the target capsule weight. The capsule weight variation in a typical batch is ±4% of the target capsule weight.

TABLE 12

SAHA Capsule Composition

| Ingredient | Unit Weight (mg) | Weight (%) |
| --- | --- | --- |
| Suberoylanilide hydroxamic acid | X | Y |
| (SAHA) - Milled Suberoylanilide | 100.0 − x | 66.67 − y |

TABLE 12-continued

SAHA Capsule Composition

| Ingredient | Unit Weight (mg) | Weight (%) |
|---|---|---|
| hydroxamic acid (SAHA) - Large | 44.33 | 29.80 |
| Microcrystalline Cellulose (Avicel PH-101) NF, Ph. Eur., JP | | |
| Croscarmellose Sodium NF, Ph. Eur., JP | 4.500 | 3.00 |
| Magnesium Stearate (vegetable grade) NF, Ph. Eur., JP | 1.170 | 0.78 |
| Hard Gelatin Capsule, Size "3" Conisnap, White Opaque/White Opaque* | 49.00 | N/A |
| Total** | 150.0 | 100.00 |

*The market capsule ink formulation is Colorcon S-1-17762. TSE-free gelatin capsules.
**Total weights do not include the hard gelatin capsule shells.

Example 14

Measurement of Dissolution Rate of SAHA Capsules

The dissolution rate of SAHA from hard gelatin capsules was evaluated using a USP Dissolution Apparatus II (VK 7000, Varian Inc., Cary, N.C.). Each capsule was placed into a helical sinker (Quality Lab Accessories L.L.C., Manville, N.J.) and delivered to vessels containing 900 mL of 2.0% Tween (TCI America, Portland, Oreg.) at a temperature of 37±0.5° C. The paddles were rotated at 100 rpm and samples were pulled at specified time intervals via an autosampler (VK 8000, Varian Inc., Cary, N.C.) equipped with 35 μm full flow filters (Varian Inc., Cary, N.C.).

Subsequently, samples were assayed for SAHA by High Performance Liquid Chromatography (Agilent 1100 series, Agilent Technologies Inc., Wilmington, Del.). The chromatographic analysis was conducted using a Phenomenex Luna C8 (2) (100×4.6 mm) 5 μm particle size column, a mobile phase of 1:1 methanol/0.1% trifluoroacetic acid (Reagent Grade, Fisher), and a detection wavelength of 242 nm.

Excipients, capsule shell and moisture showed little effect on the dissolution rate of the SAHA capsule contents. However, the particle size distribution of SAHA influenced the dissolution rate.

Figure 5:
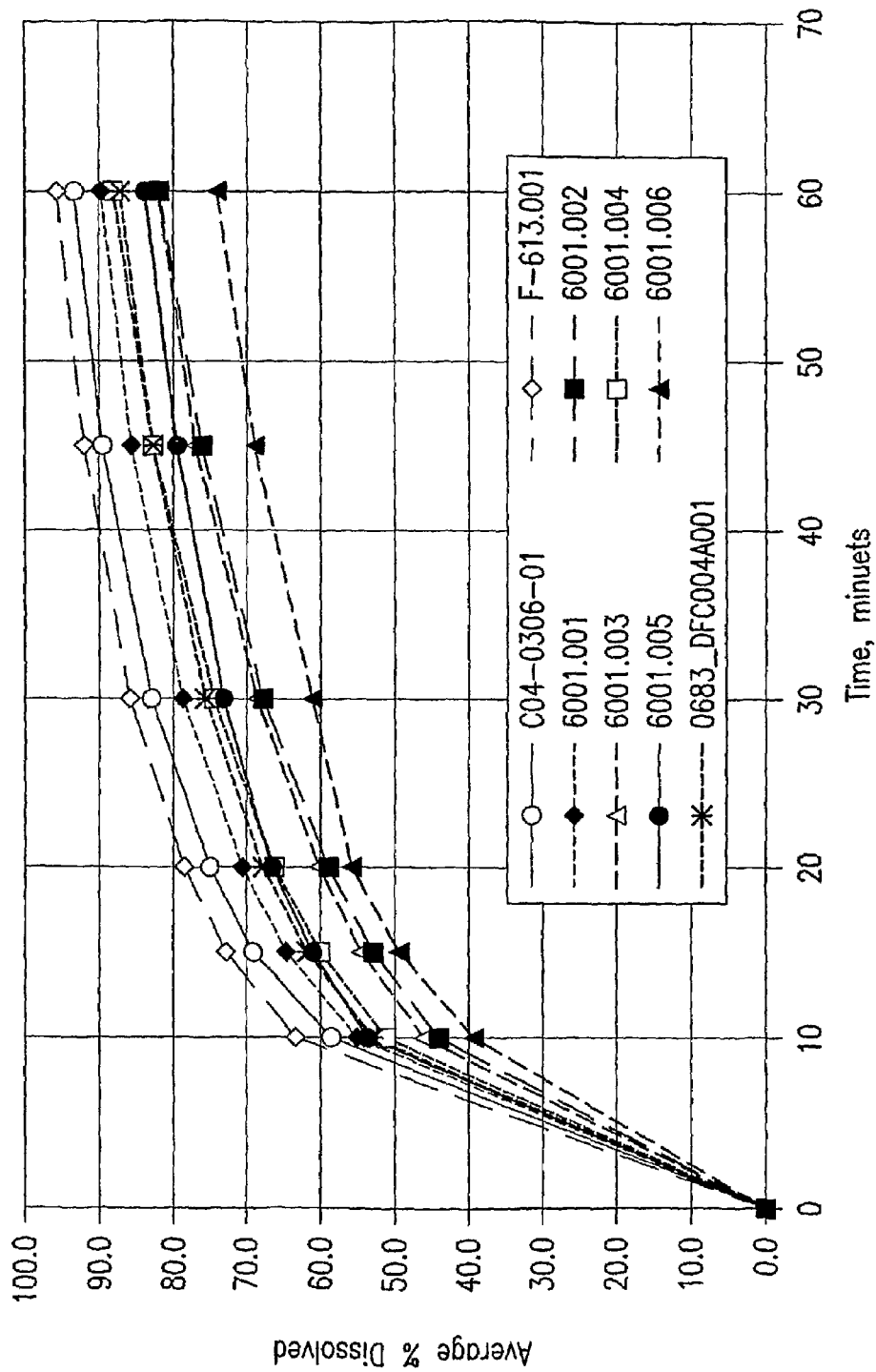
FIG. 5 shows the dissolution profiles of SAHA from pharmaceutical capsules of the invention. The capsules contain about 100 mg of active ingredient SAHA, and excipients.

The dissolution rate profiles of SAHA from the capsule contents are illustrated in Tables 13, 14 and FIG. 5. The dissolution rate profile of SAHA from the reference capsule Lot 0683_004A001 is illustrated in FIG. 1. The F2 factors of SAHA from various capsule batches were calculated using capsule Lot 0683_004A001 as the reference.

TABLE 13

Dissolution Rate of SAHA Capsules

| Capsule Lot # | Average SAHA % (with RMSD) Dissolved at Time (minutes) | | | | | | | F2 Factor |
| | 0 | 10 | 15 | 20 | 30 | 45 | 60 | |
|---|---|---|---|---|---|---|---|---|
| C04-0306-001 | 0.0 | 58.5 | 68.9 | 75.0 | 82.9 | 89.4 | 93.1 | 58.2 |
| | 0.0 | 6.5 | 5.2 | 4.4 | 3.0 | 1.8 | 1.1 | |
| F-613-001 | 0.0 | 63.3 | 72.7 | 78.5 | 85.7 | 91.9 | 95.4 | 49.7 |
| | 0.0 | 2.8 | 2.3 | 1.5 | 1.1 | 1.3 | 1.0 | |
| 6001.001 | 0.0 | 55.1 | 64.6 | 70.5 | 78.7 | 85.5 | 89.7 | 76.2 |
| | 0.0 | 3.2 | 3.0 | 2.6 | 2.3 | 2.8 | 2.8 | |
| 6001.002 | 0.0 | 43.9 | 52.9 | 59.0 | 67.7 | 76.1 | 81.7 | 55.3 |
| | 0.0 | 8.7 | 7.1 | 6.4 | 4.8 | 3.6 | 3.1 | |
| 6001.003 | 0.0 | 46.0 | 54.5 | 60.1 | 68.5 | 76.9 | 81.8 | 58.7 |
| | 0.0 | 3.1 | 2.7 | 2.8 | 3.0 | 3.0 | 3.4 | |
| 6001.004 | 0.0 | 51.2 | 60.0 | 66.1 | 74.5 | 82.5 | 87.9 | 89.7 |
| | 0.0 | 2.8 | 2.3 | 1.9 | 2.3 | 2.4 | 2.1 | |
| 6001.005 | 0.0 | 53.5 | 61.0 | 66.5 | 73.1 | 79.3 | 83.6 | 80.3 |
| | 0.0 | 2.5 | 1.5 | 1.8 | 2.5 | 3.0 | 2.7 | |
| 6001.006 | 0.0 | 39.2 | 49.4 | 55.8 | 61.0 | 68.8 | 73.9 | 43.9 |
| | 0.0 | 0.4 | 6.3 | 8.7 | 3.3 | 4.1 | 4.2 | |
| 0683_004A001 | 0.0 | 52.7 | 61.7 | 67.7 | 75.5 | 82.6 | 87.0 | Reference Lot |

TABLE 14

Dissolution Rate Profile of 0683_DFC007A001

| Capsule Density | Average SAHA % Dissolved at Time, minutes | | | | | | | F2 Factor |
| | 0 | 10 | 15 | 20 | 30 | 45 | 60 | |
|---|---|---|---|---|---|---|---|---|
| 0683_007A001 | 0.0 | 47 | 56 | 62 | 70 | 78 | 82 | 61.9 |
| | 0.0 | 2.6 | 2.8 | 2.8 | 3.0 | 3.6 | 3.3 | |
| 0683_004A001 | 0.0 | 52.7 | 61.7 | 67.7 | 75.5 | 82.6 | 87.0 | Reference Lot |
| | 0.0 | 5.7 | 5.2 | 5.0 | 4.7 | 4.5 | 4.3 | |

Example 15

Measurement of Dissolution Rate of SAHA API

The dissolution rate of 100 mg of SAHA API before encapsulation was evaluated using a USP Dissolution Apparatus II (VK 7000, Varian Inc., Cary, N.C.). About 100 mg of SAHA was delivered to vessels containing 900 mL of 2.0% Tween (TCI America, Portland, Oreg.) at a temperature of 37±0.5° C. The paddles were rotated at 100 rpm and samples were pulled at specified time intervals via an autosampler (VK 8000, Varian Inc., Cary, N.C.) equipped with 35 μm full flow filters (Varian Inc., Cary, N.C.).

Subsequently, samples were assayed for SAHA by High Performance Liquid Chromatography (Agilent 1100 series, Agilent Technologies Inc., Wilmington, Del.). The chromatographic analysis was conducted using a Phenomenex Luna C8 (2) (100×4.6 mm) 5 μm particle size column, a mobile phase of 1:1 methanol/0.1% trifluoroacetic acid (Reagent Grade, Fisher), and a detection wavelength of 242 nm.

Figure 6:
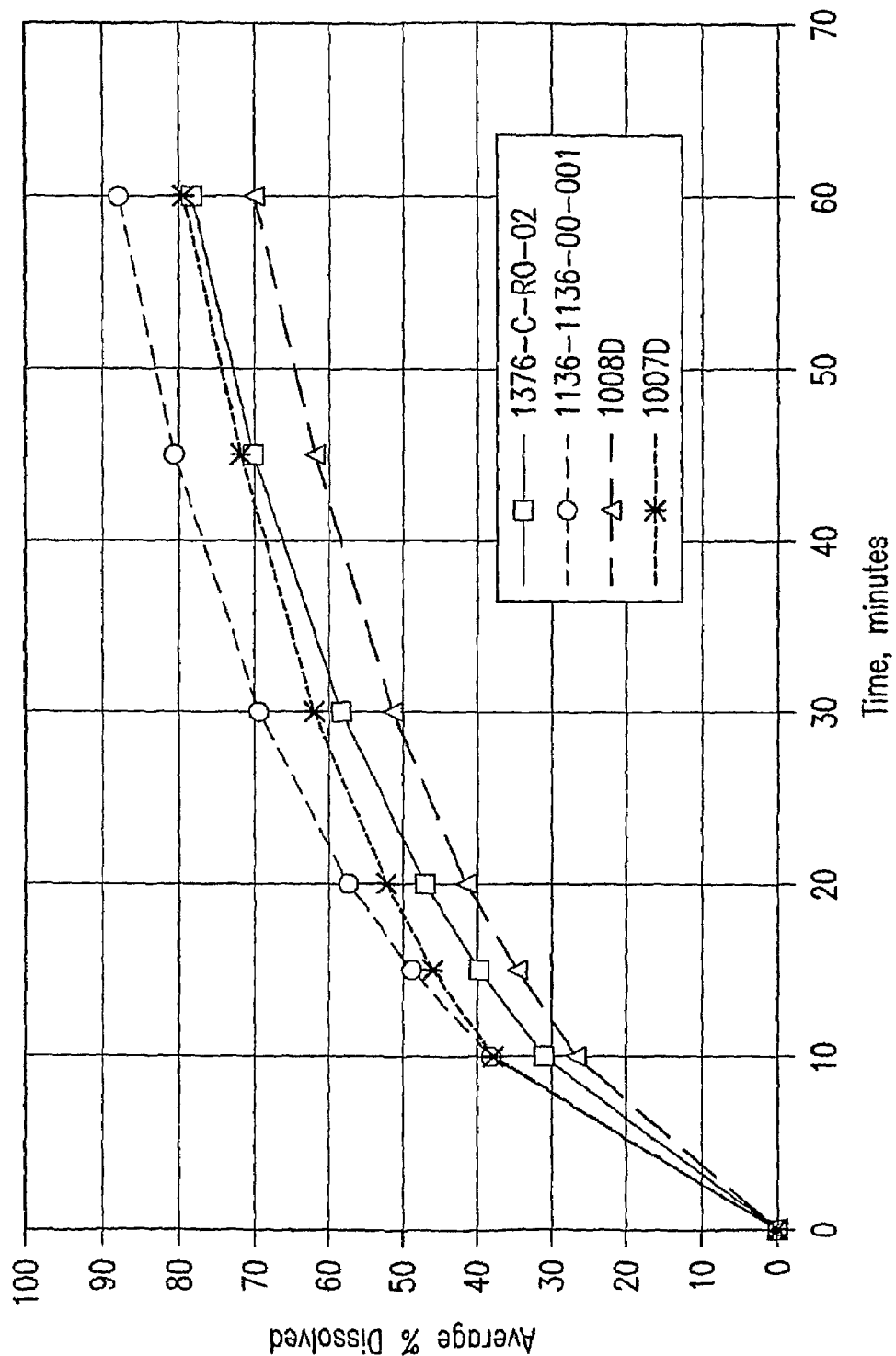
FIG. 6 shows the dissolution profiles of SAHA API batches (blended SAHA crystals) prior to encapsulation. The dissolution profiles were measured based on about 100 mg of SAHA.

The dissolution rate profiles of the SAHA API batches are illustrated in Table 15 and FIG. 6.

TABLE 15

Dissolution Rate Profiles of SAHA API batches

| API Lot # | Average SAHA % Dissolved at Time, minutes | | | | | | |
|---|---|---|---|---|---|---|---|
| | 0 | 10 | 15 | 20 | 30 | 45 | 60 |
| 1136-1136-00-001 | 0.0 | 38.2 | 48.9 | 57.3 | 69.3 | 80.6 | 87.7 |
| | 0.0 | 1.7 | 2.4 | 2.7 | 2.8 | 3.6 | 2.6 |
| 1376-C-RO-02 | 0.0 | 31.1 | 39.7 | 47.1 | 58.3 | 70.1 | 78.3 |
| | 0.0 | 5.2 | 4.5 | 3.1 | 3.1 | 2.7 | 2.9 |
| 1008D | 0.0 | 26.8 | 34.8 | 41.5 | 51.3 | 61.8 | 69.8 |
| | 0.0 | 2.6 | 3.1 | 2.6 | 2.2 | 2.4 | 2.1 |
| 1007D | 0.0 | 37.8 | 46.1 | 52.1 | 61.9 | 71.8 | 79.3 |
| | 0.0 | 3.3 | 3.2 | 2.6 | 2.4 | 2.4 | 2.0 |

Example 16

Measurement of Particle Size Distribution

Particle size measurements of the blended SAHA crystals (Active Pharmaceutical Ingredient: API), lubricated formulation blend, and capsule contents were determined via a Sympatec laser diffraction analyzer (HELOS H1006, Clausthal-Zellerfeld, Germany) equipped with a RODOS powder dispersion system.

Approximately 150 mg of sample was manually delivered to the system and atomized through a laser beam using 0.1 bar air pressure. Data was collected using a focal length lens of 850 or 1750-μm and the targeted obscuration range was 5-20%. The fraunhofer optical model was utilized to deconvolute the sample scattering patterns to yield the resultant particle size distributions.

Figure 3:
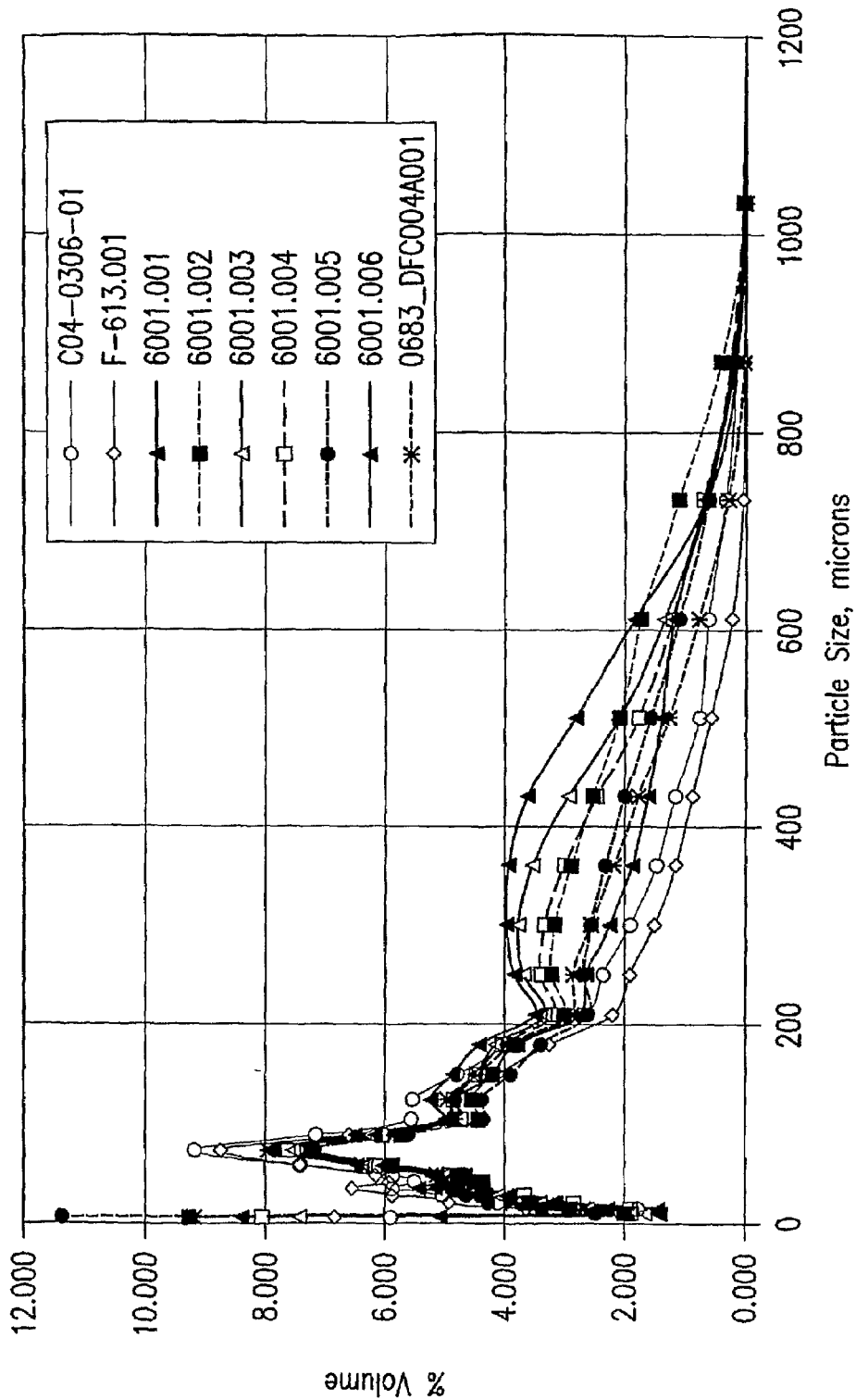
FIG. 3 shows the particle size distribution of the capsule content of pharmaceutical capsules of the invention. The capsules contain about 100 mg of active ingredient SAHA, and excipients.
Figure 4:
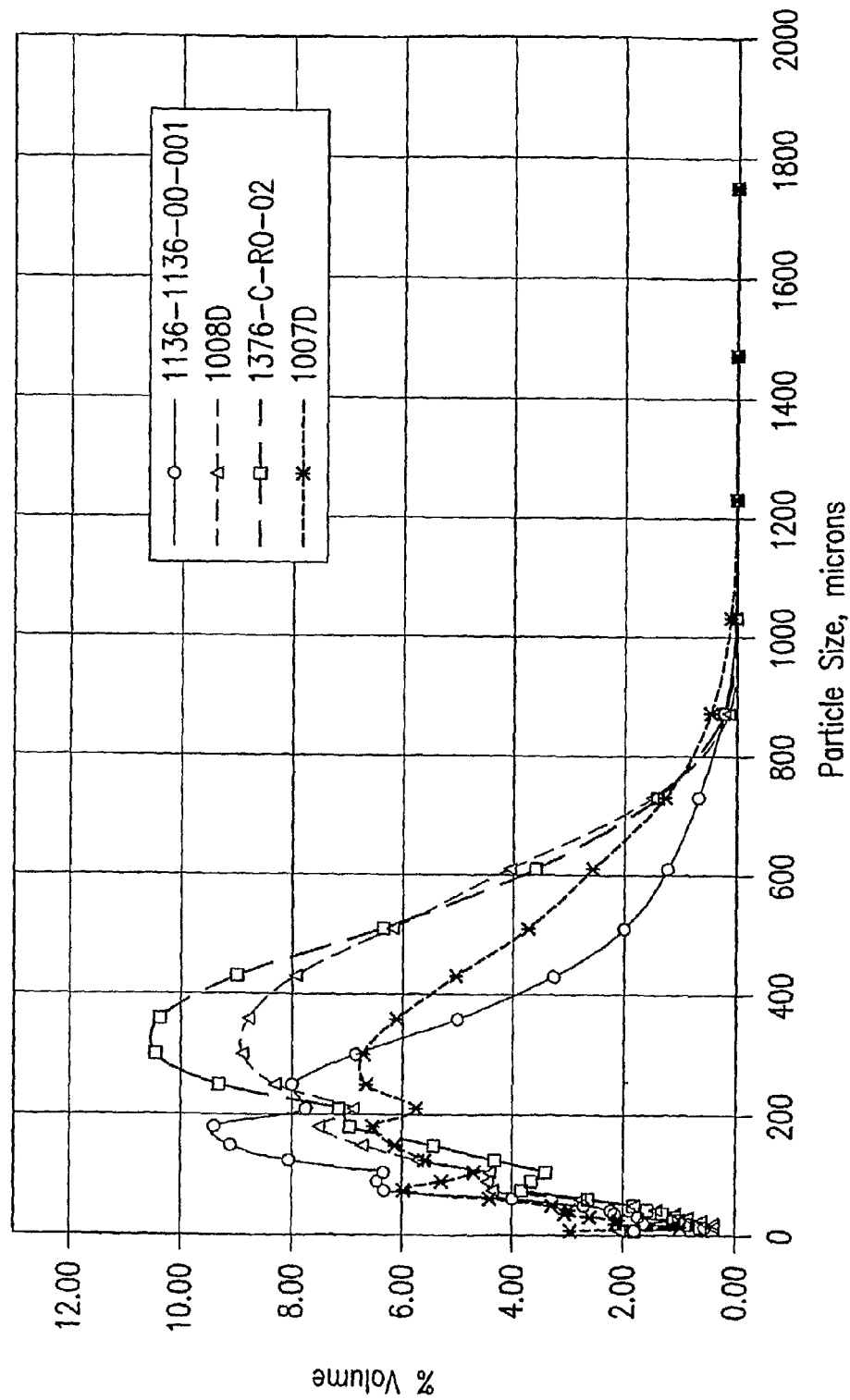
FIG. 4 shows the particle size distribution of the active ingredient SAHA from different batches prior to encapsulation (API).
Figure 12:
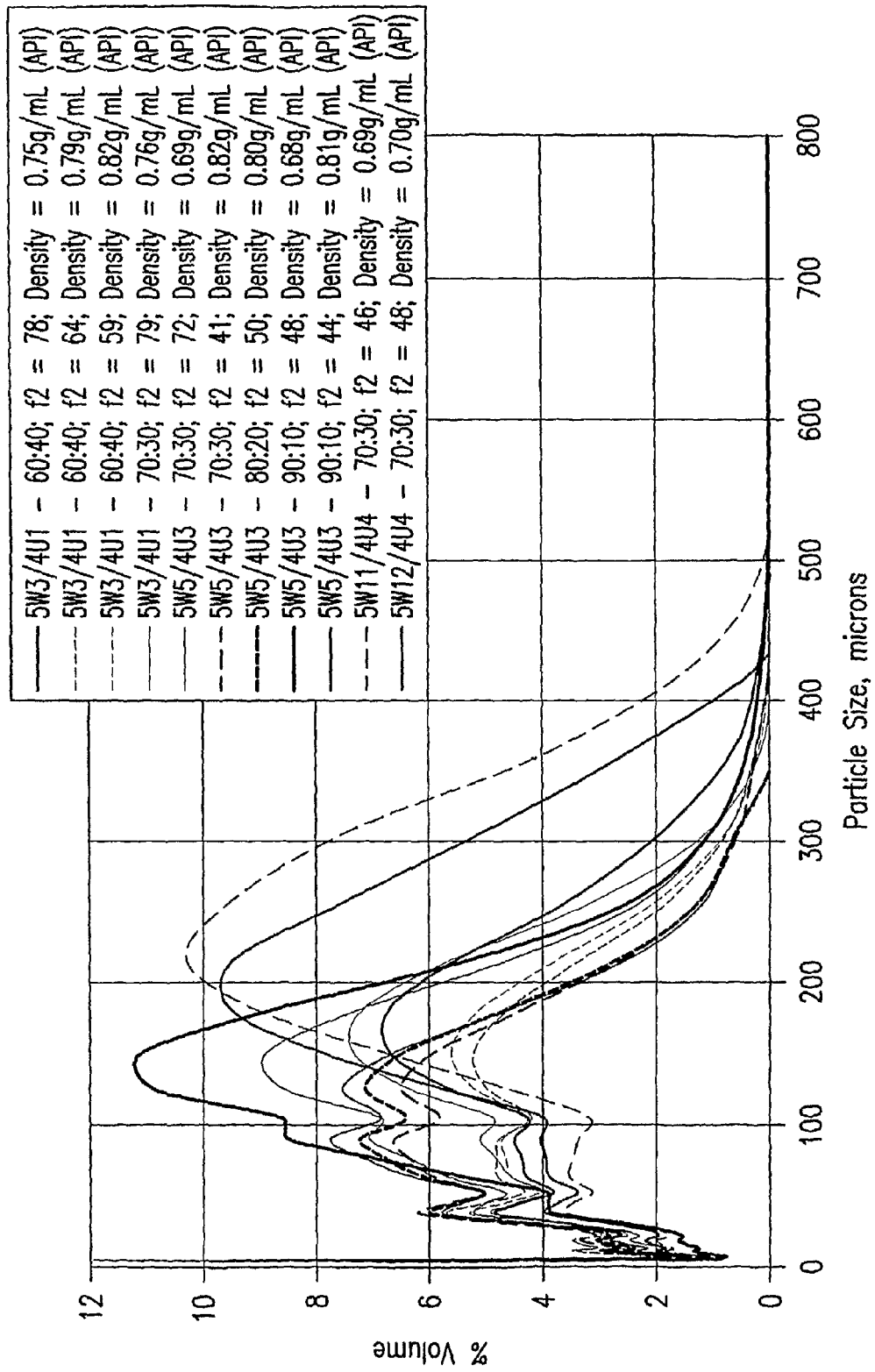
FIG. 12 shows the normalized particle size distribution of Active Ingredient (API) from different batches of SAHA capsules.
Figure 13:
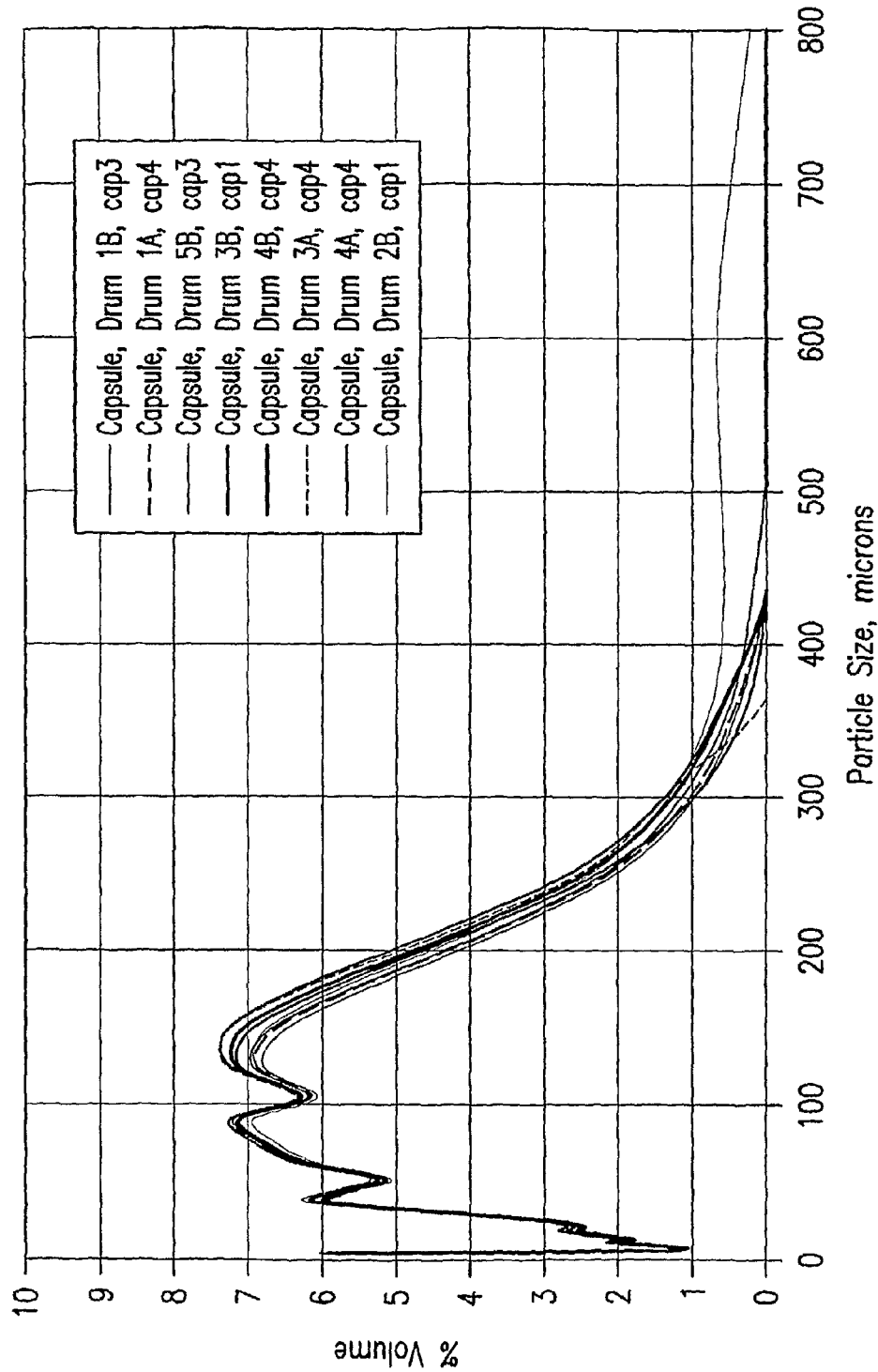
FIG. 13 shows the particle size distribution of capsule content from Lot C0666001.
Figure 14:
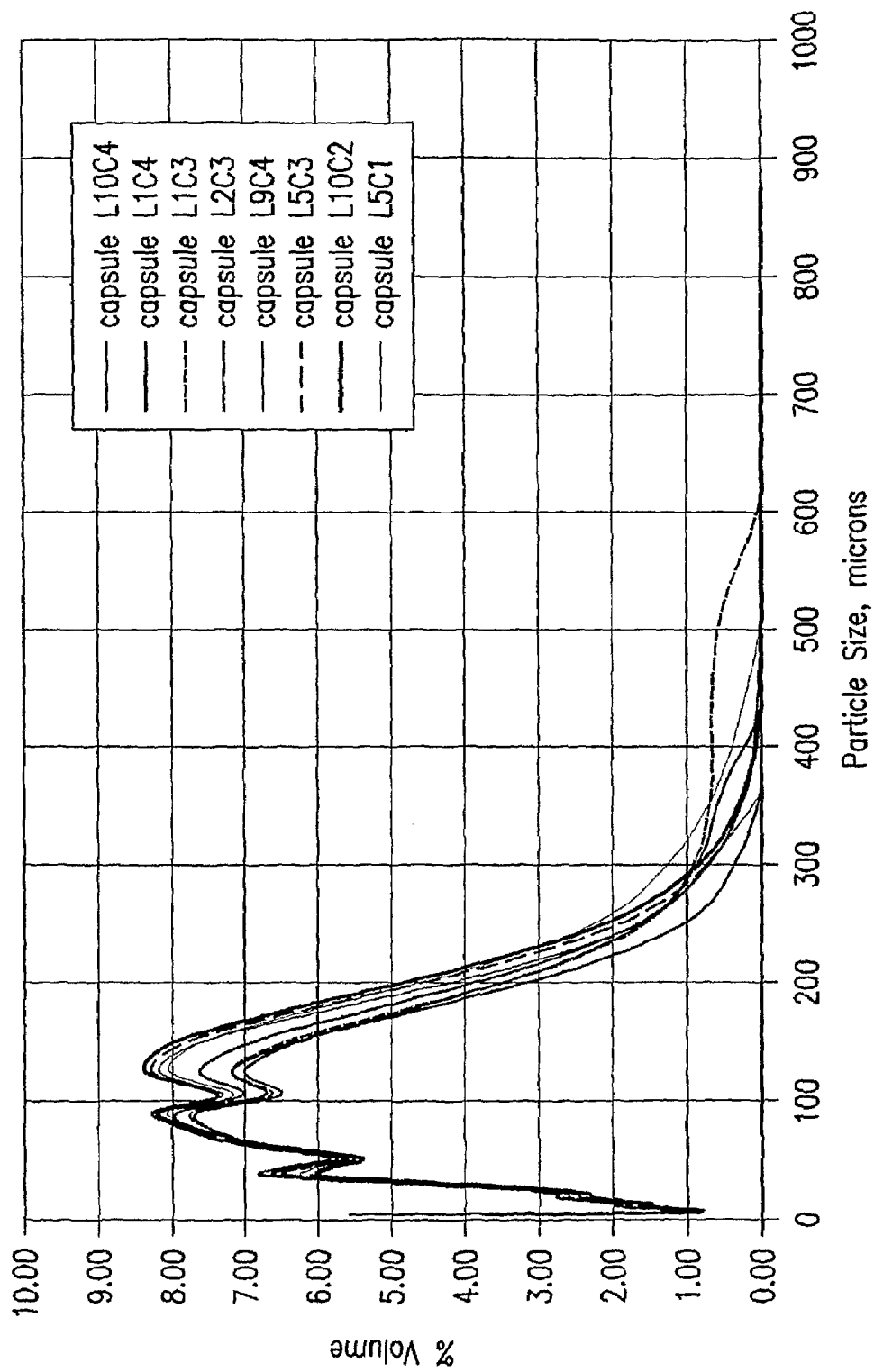
FIG. 14 shows the particle size distribution of capsule content from Lot C0667001.
Figure 15:
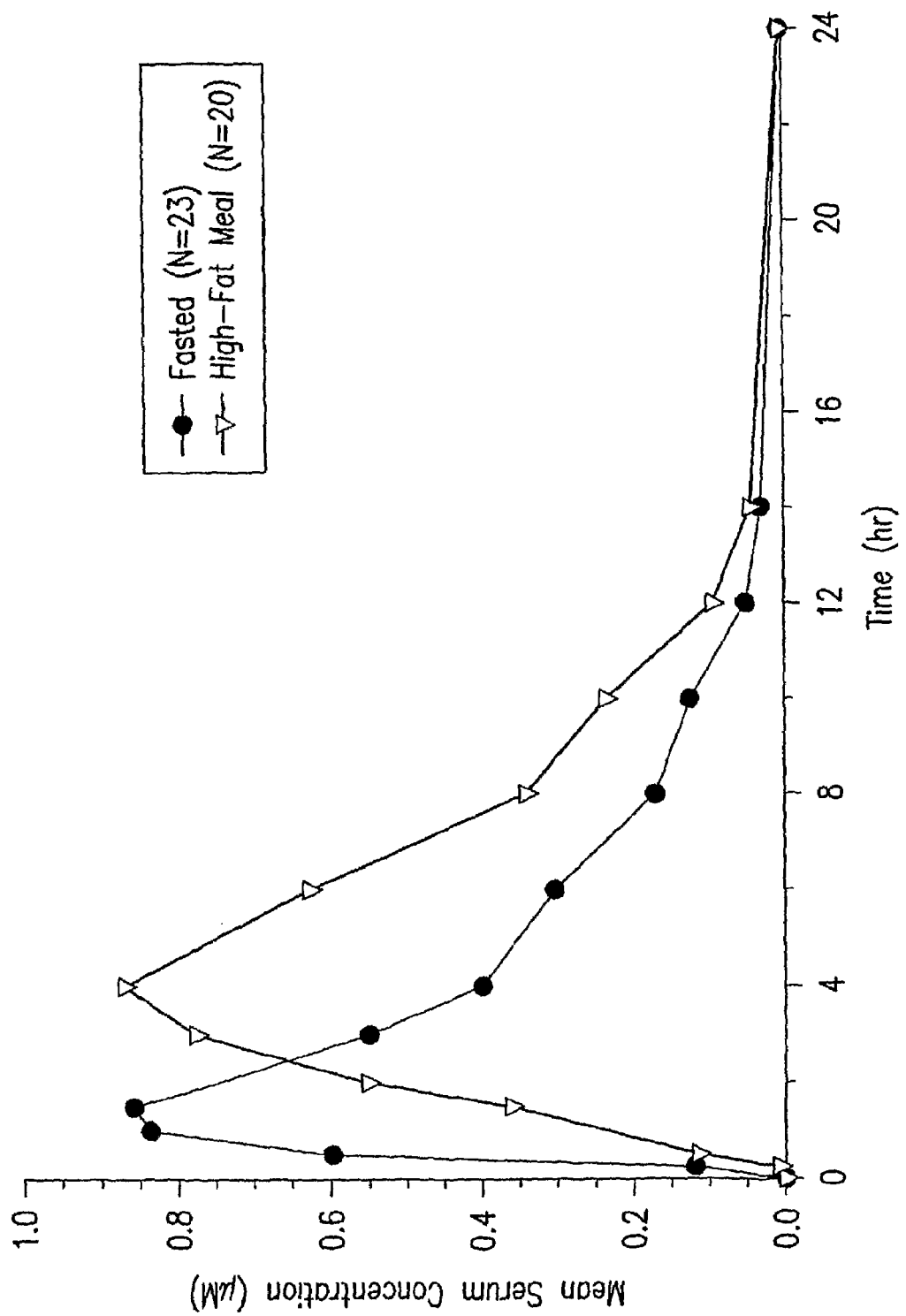
FIG. 15 shows mean serum concentrations of vorinostat following administration of a single oral dose in the fasted state and following a high-fat meal.
Figure 16:
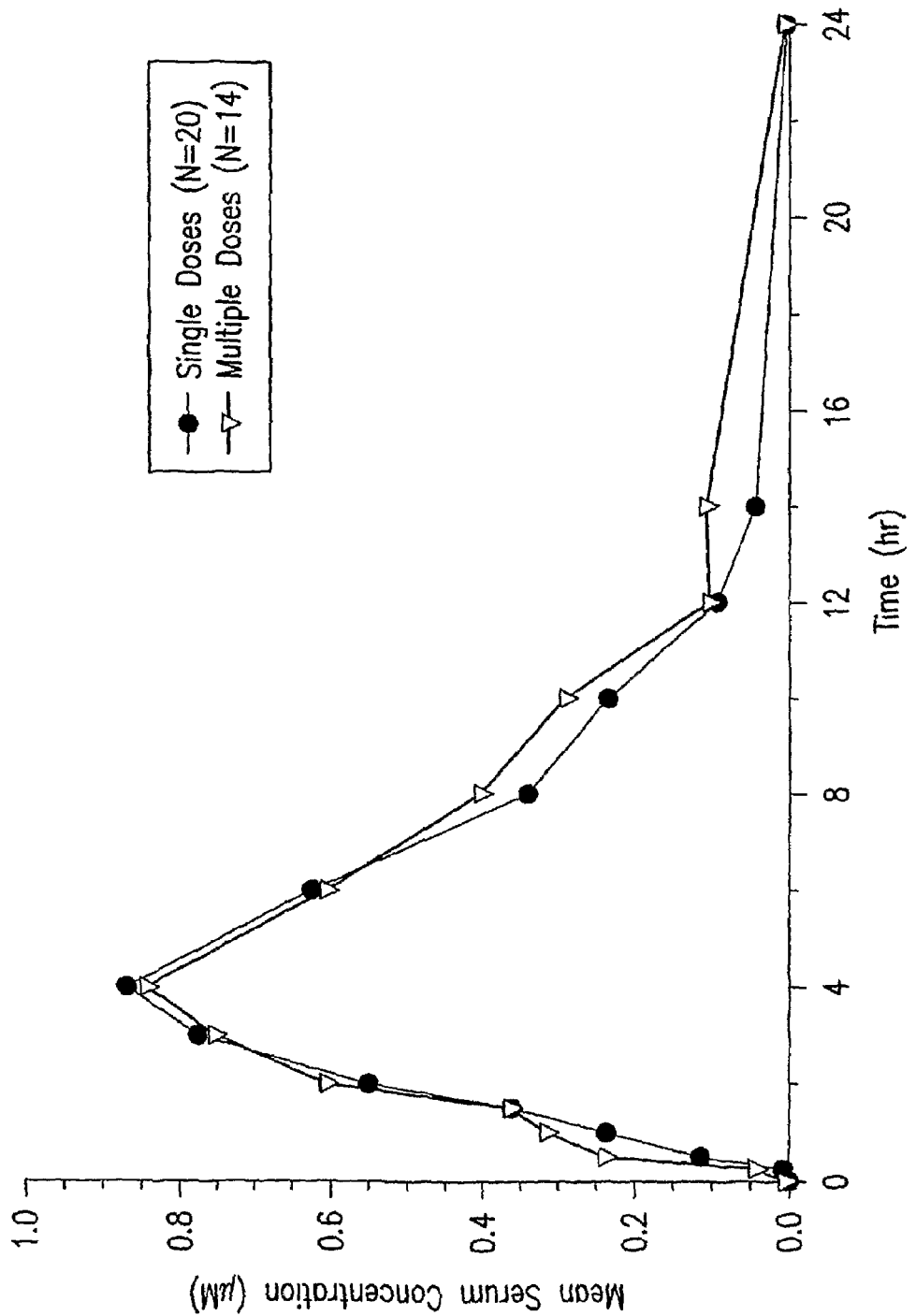
FIG. 16 shows mean serum concentrations of vorinostat following administration of 400 mg single or multiple oral doses following a high-fat meal.

The particle size distribution of the SAHA capsule contents are illustrated in Table 16 and FIG. 3. The particle size distribution of the SAHA API batches prior to encapsulation are illustrated in Table 17 and FIG. 4. The particle size distribution of SAHA capsules prepared using a Blend of API 288 (30% wet-milled) and 283 (70% Large crystals) are illustrated in Table 18. The normalized particle size distribution of SAHA from capsules prepared using different blends of wet-milled and large crystals are illustrated in Table 19 and FIG. 12. The particle size distribution of Lot C0666001 SAHA capsules prepared using 30% wet-milled and 70% large crystals are illustrated in Table 20 and FIG. 13. The particle size distribution of Lot C0667001 SAHA capsules prepared using 30% wet-milled and 70% large crystals are illustrated in Table 21 and FIG. 14.

TABLE 16

Particle Size Distribution of SAHA Capsule Content

| Particle Size (μm) | % Volume Capsule Lot # | | | | | | | | |
|---|---|---|---|---|---|---|---|---|---|
| | C04-0306-001 | F-613.001 | 6001.001 | 6001.002 | 6001.003 | 6001.004 | 6001.005 | 6001.006 | 0683 DFC004A001 |
| 9 | 5.892 | 6.860 | 8.426 | 9.278 | 7.468 | 8.043 | 11.36 | 5.039 | 9.193 |
| 11 | 1.742 | 2.068 | 2.075 | 2.096 | 1.776 | 1.933 | 2.516 | 1.421 | 2.140 |
| 13 | 1.844 | 2.214 | 2.104 | 2.060 | 1.783 | 1.933 | 2.440 | 1.479 | 2.130 |
| 15 | 1.926 | 2.332 | 2.123 | 2.021 | 1.785 | 1.926 | 2.361 | 1.526 | 2.113 |
| 18 | 3.004 | 3.636 | 3.180 | 2.955 | 2.669 | 2.866 | 3.399 | 2.351 | 3.125 |
| 22 | 4.110 | 4.934 | 4.180 | 3.793 | 3.518 | 3.748 | 4.282 | 3.193 | 4.060 |
| 26 | 4.126 | 4.884 | 4.061 | 3.623 | 3.443 | 3.636 | 4.009 | 3.204 | 3.918 |
| 31 | 5.082 | 5.892 | 4.853 | 4.288 | 4.166 | 4.362 | 4.647 | 3.957 | 4.670 |
| 37 | 5.858 | 6.582 | 5.428 | 4.786 | 4.751 | 4.928 | 5.082 | 4.600 | 5.245 |
| 43 | 5.496 | 5.952 | 4.969 | 4.404 | 4.442 | 4.573 | 4.587 | 4.370 | 4.833 |
| 50 | 5.892 | 6.144 | 5.229 | 4.671 | 4.772 | 4.880 | 4.792 | 4.753 | 5.130 |
| 60 | 7.444 | 7.434 | 6.501 | 5.863 | 6.056 | 6.157 | 5.935 | 6.121 | 6.430 |
| 75 | 9.194 | 8.754 | 7.950 | 7.220 | 7.540 | 7.623 | 7.228 | 7.777 | 7.903 |
| 90 | 7.188 | 6.594 | 6.220 | 5.678 | 5.977 | 6.014 | 5.623 | 6.290 | 6.198 |
| 105 | 5.582 | 4.994 | 4.876 | 4.474 | 4.736 | 4.747 | 4.376 | 5.057 | 4.873 |
| 125 | 5.524 | 4.836 | 4.920 | 4.560 | 4.846 | 4.839 | 4.372 | 5.233 | 4.943 |
| 150 | 4.774 | 4.092 | 4.426 | 4.205 | 4.494 | 4.451 | 3.904 | 4.860 | 4.488 |
| 180 | 3.872 | 3.260 | 3.804 | 3.810 | 4.116 | 4.022 | 3.404 | 4.400 | 3.910 |
| 210 | 2.658 | 2.196 | 2.776 | 3.025 | 3.338 | 3.189 | 2.605 | 3.510 | 2.913 |
| 250 | 2.386 | 1.930 | 2.649 | 3.238 | 3.692 | 3.418 | 2.691 | 3.840 | 2.873 |
| 300 | 1.922 | 1.520 | 2.266 | 3.176 | 3.778 | 3.350 | 2.570 | 3.963 | 2.583 |
| 360 | 1.484 | 1.162 | 1.891 | 2.910 | 3.548 | 3.025 | 2.326 | 3.930 | 2.198 |
| 430 | 1.172 | 0.876 | 1.623 | 2.536 | 2.951 | 2.471 | 1.988 | 3.623 | 1.778 |

TABLE 16-continued

Particle Size Distribution of SAHA Capsule Content

% Volume Capsule Lot #

| Particle Size (μm) | C04-0306-001 | F-613.001 | 6001.001 | 6001.002 | 6001.003 | 6001.004 | 6001.005 | 6001.006 | 0683 DFC004A001 |
|---|---|---|---|---|---|---|---|---|---|
| 510 | 0.762 | 0.576 | 1.391 | 2.100 | 2.088 | 1.777 | 1.572 | 2.839 | 1.273 |
| 610 | 0.614 | 0.232 | 1.194 | 1.729 | 1.351 | 1.210 | 1.086 | 1.843 | 0.768 |
| 730 | 0.326 | 0.048 | 0.691 | 1.093 | 0.644 | 0.701 | 0.602 | 0.634 | 0.285 |
| 870 | 0.126 | 0.000 | 0.191 | 0.409 | 0.234 | 0.174 | 0.245 | 0.127 | 0.030 |
| 1030 | 0.000 | 0.000 | 0.009 | 0.000 | 0.039 | 0.000 | 0.000 | 0.064 | 0.000 |
| 1230 | 0.000 | 0.000 | 0.000 | 0.000 | 0.000 | 0.000 | 0.000 | 0.000 | 0.000 |
| 1470 | 0.000 | 0.000 | 0.000 | 0.000 | 0.000 | 0.000 | 0.000 | 0.000 | 0.000 |
| 1750 | 0.000 | 0.000 | 0.000 | 0.000 | 0.000 | 0.000 | 0.000 | 0.000 | 0.000 |

TABLE 17

Particle Size Distribution of SAHA API Batches

% Volume API Lot #

| Particle Size (μm) | 1136-1136-00-001 | 1376-C-RO-02 | 1008D | 1007D |
|---|---|---|---|---|
| 9 | 1.77 | 1.76 | 2.02 | 2.92 |
| 11 | 0.52 | 0.45 | 0.45 | 0.87 |
| 13 | 0.55 | 0.46 | 0.44 | 0.91 |
| 15 | 0.58 | 0.47 | 0.44 | 0.95 |
| 18 | 0.91 | 0.72 | 0.66 | 1.48 |
| 22 | 1.27 | 0.99 | 0.88 | 2.03 |
| 26 | 1.33 | 1.00 | 0.89 | 2.06 |
| 31 | 1.72 | 1.27 | 1.14 | 2.58 |
| 37 | 2.14 | 1.55 | 1.42 | 3.05 |
| 43 | 2.22 | 1.56 | 1.49 | 2.95 |
| 50 | 2.68 | 1.83 | 1.83 | 3.28 |
| 60 | 4.00 | 2.60 | 2.76 | 4.39 |
| 75 | 6.30 | 3.81 | 4.35 | 5.96 |
| 90 | 6.44 | 3.63 | 4.44 | 5.29 |
| 105 | 6.36 | 3.42 | 4.42 | 4.72 |
| 125 | 8.05 | 4.35 | 5.71 | 5.58 |
| 150 | 9.07 | 5.47 | 6.72 | 6.13 |
| 180 | 9.36 | 6.92 | 7.48 | 6.52 |
| 210 | 7.73 | 7.14 | 6.88 | 5.78 |
| 250 | 7.96 | 9.27 | 8.24 | 6.63 |
| 300 | 6.82 | 10.42 | 8.86 | 6.70 |
| 360 | 4.99 | 10.36 | 8.75 | 6.09 |
| 430 | 3.24 | 8.97 | 7.90 | 5.03 |
| 510 | 1.95 | 6.34 | 6.16 | 3.71 |
| 610 | 1.21 | 3.60 | 4.07 | 2.54 |
| 730 | 0.66 | 1.40 | 1.48 | 1.26 |
| 870 | 0.24 | 0.23 | 0.11 | 0.45 |
| 1030 | 0.00 | 0.00 | 0.00 | 0.10 |
| 1230 | 0.00 | 0.00 | 0.00 | 0.00 |
| 1470 | 0.00 | 0.00 | 0.00 | 0.00 |
| 1750 | 0.00 | 0.00 | 0.00 | 0.00 |

TABLE 18

Particle Size Distribution of SAHA Capsules prepared using a Blend of API 288 (30% wet-milled) and 283 (70% Large)

| Particle Size, μm | % Volume Capsule Density | | | | |
|---|---|---|---|---|---|
| | 0.73 | 0.81 | 0.84 | 0.90 | Biobatch |
| 4.5 | 5.32 | 5.97 | 6.27 | 7.22 | 5.86 |
| 5.5 | 1.20 | 1.34 | 1.43 | 1.62 | 1.29 |
| 6.5 | 1.16 | 1.28 | 1.37 | 1.54 | 1.22 |
| 7.5 | 1.12 | 1.23 | 1.32 | 1.47 | 1.17 |
| 9 | 1.59 | 1.75 | 1.89 | 2.09 | 1.68 |
| 11 | 2.00 | 2.21 | 2.39 | 2.61 | 2.15 |
| 13 | 1.88 | 2.08 | 2.26 | 2.45 | 2.11 |
| 15.5 | 2.22 | 2.48 | 2.68 | 2.88 | 2.64 |
| 18.5 | 2.51 | 2.83 | 3.06 | 3.25 | 3.21 |
| 21.5 | 2.39 | 2.72 | 2.92 | 3.09 | 3.25 |
| 25 | 2.69 | 3.08 | 3.28 | 3.44 | 3.8 |
| 30 | 3.69 | 4.25 | 4.49 | 4.67 | 5.32 |
| 37.5 | 5.28 | 6.07 | 6.35 | 6.53 | 7.45 |
| 45 | 4.99 | 5.68 | 5.88 | 5.97 | 6.63 |
| 52.5 | 4.66 | 5.27 | 5.39 | 5.42 | 5.81 |
| 62.5 | 5.67 | 6.34 | 6.42 | 6.37 | 6.57 |
| 75 | 6.28 | 6.89 | 6.88 | 6.75 | 6.66 |
| 90 | 6.63 | 7.06 | 6.95 | 6.72 | 6.34 |
| 105 | 5.89 | 6.02 | 5.81 | 5.53 | 5.02 |
| 125 | 6.92 | 6.69 | 6.28 | 5.84 | 5.15 |
| 150 | 7.31 | 6.52 | 5.87 | 5.29 | 4.7 |
| 180 | 6.83 | 5.51 | 4.69 | 4.09 | 3.98 |
| 215 | 5.43 | 3.85 | 3.13 | 2.67 | 3.19 |
| 255 | 3.53 | 2.04 | 1.75 | 1.49 | 2.36 |
| 305 | 1.95 | 0.71 | 0.95 | 0.81 | 1.61 |
| 365 | 0.78 | 0.12 | 0.20 | 0.13 | 0.84 |
| 435 | 0.06 | 0.00 | 0.06 | 0.06 | 0 |
| 515 | 0.00 | 0.00 | 0.00 | 0.00 | 0 |
| 615 | 0.00 | 0.00 | 0.00 | 0.00 | 0 |
| 735 | 0.00 | 0.00 | 0.00 | 0.00 | 0 |
| 875 | 0.00 | 0.00 | 0.00 | 0.00 | 0 |

TABLE 19

Normalized Particle Size Distribution of SAHA from capsules prepared using different blends of wet-milled and large crystals % Volume SAHA 100 mg

| Particle Size (μm) | 5W3/4U1; 60:40; f2 = 78 ρ = 0.75 g/mL | 5W3/4U1; 60:40; f2 = 64 ρ = 0.79 g/mL | 5W3/4U1; 60:40; f2 = 59 ρ = 0.82 g/mL | 5W3/4U1; 70:30; f2 = 79 ρ = 0.76 g/mL | 5W5/4U3; 70:30; f2 = 72 ρ = 0.69 g/mL | 5W5/4U3; 70:30; f2 = 41 ρ = 0.82 g/mL | 5W5/4U3; 80:20; f2 = 50 ρ = 0.80 g/mL | 5W5/4U3; 90:10; f2 = 48 ρ = 0.68 g/mL | 5W5/4U3; 90:10; f2 = 44 ρ = 0.81 g/mL | 5W11/4U4; 70:30; f2 = 46 ρ = 0.69 g/mL | 5W12/4U4; 70:30; f2 = 48 ρ = 0.70 g/mL |
|---|---|---|---|---|---|---|---|---|---|---|---|
| 5 | 9.850 | 11.86 | 11.95 | 9.352 | 4.525 | 7.402 | 7.028 | 4.052 | 7.268 | 5.281 | 5.442 |
| 6 | 2.103 | 2.486 | 2.488 | 1.953 | 1.080 | 1.673 | 1.553 | 0.857 | 1.554 | 1.168 | 1.227 |
| 7 | 1.967 | 2.306 | 2.322 | 1.802 | 1.062 | 1.625 | 1.491 | 0.810 | 1.447 | 1.106 | 1.180 |
| 8 | 1.831 | 2.125 | 2.156 | 1.681 | 1.044 | 1.563 | 1.429 | 0.763 | 1.371 | 1.059 | 1.133 |
| 9 | 2.513 | 2.910 | 2.942 | 2.303 | 1.519 | 2.245 | 2.052 | 1.074 | 1.904 | 1.504 | 1.607 |
| 11 | 2.983 | 3.425 | 3.471 | 2.729 | 1.945 | 2.805 | 2.551 | 1.322 | 2.330 | 1.841 | 1.988 |
| 13 | 2.630 | 3.028 | 3.045 | 2.406 | 1.859 | 2.615 | 2.377 | 1.222 | 2.155 | 1.681 | 1.828 |
| 16 | 2.885 | 3.313 | 3.315 | 2.661 | 2.188 | 3.033 | 2.750 | 1.417 | 2.500 | 1.877 | 2.054 |
| 19 | 2.988 | 3.460 | 3.417 | 2.808 | 2.454 | 3.329 | 3.046 | 1.594 | 2.780 | 1.994 | 2.186 |
| 22 | 2.616 | 3.073 | 2.971 | 2.509 | 2.304 | 3.060 | 2.821 | 1.533 | 2.630 | 1.770 | 1.962 |
| 25 | 2.741 | 3.243 | 3.096 | 2.680 | 2.578 | 3.334 | 3.110 | 1.763 | 2.934 | 1.896 | 2.088 |
| 30 | 3.540 | 4.203 | 3.939 | 3.537 | 3.539 | 4.429 | 4.190 | 2.502 | 4.029 | 2.516 | 2.767 |
| 38 | 4.831 | 5.671 | 5.274 | 4.901 | 5.186 | 6.150 | 5.940 | 3.823 | 5.735 | 3.600 | 3.939 |
| 45 | 4.361 | 5.024 | 4.671 | 4.461 | 5.013 | 5.621 | 5.514 | 3.902 | 5.413 | 3.441 | 3.721 |
| 53 | 3.818 | 4.333 | 4.054 | 3.962 | 4.677 | 5.048 | 5.046 | 3.937 | 5.048 | 3.120 | 3.386 |
| 63 | 4.277 | 4.792 | 4.542 | 4.540 | 5.611 | 5.878 | 6.038 | 5.271 | 6.204 | 3.520 | 3.874 |
| 75 | 4.358 | 4.813 | 4.653 | 4.798 | 6.270 | 6.315 | 6.712 | 6.791 | 7.086 | 3.467 | 3.940 |
| 90 | 4.504 | 4.781 | 4.725 | 5.107 | 7.068 | 6.609 | 7.228 | 8.509 | 7.751 | 3.361 | 4.042 |
| 105 | 4.275 | 4.197 | 4.274 | 4.894 | 6.870 | 5.817 | 6.407 | 8.637 | 6.870 | 3.177 | 3.991 |
| 125 | 5.623 | 4.981 | 5.192 | 6.329 | 8.573 | 6.482 | 7.132 | 10.88 | 7.535 | 4.599 | 5.738 |
| 150 | 6.677 | 5.219 | 5.608 | 7.338 | 8.886 | 5.935 | 6.480 | 11.11 | 6.661 | 6.735 | 7.874 |
| 180 | 6.733 | 4.637 | 5.129 | 7.201 | 7.295 | 4.389 | 4.698 | 8.825 | 4.641 | 9.030 | 9.486 |
| 215 | 5.546 | 3.333 | 3.765 | 5.630 | 4.625 | 2.609 | 2.697 | 5.339 | 2.535 | 10.29 | 9.470 |
| 255 | 3.640 | 1.829 | 2.067 | 3.192 | 2.320 | 1.282 | 1.266 | 2.528 | 1.178 | 9.571 | 7.595 |
| 305 | 1.934 | 0.747 | 0.777 | 1.117 | 1.029 | 0.555 | 0.599 | 1.044 | 0.599 | 7.539 | 5.120 |
| 365 | 0.629 | 0.243 | 0.184 | 0.139 | 0.392 | 0.228 | −0.127 | 0.377 | −0.127 | 3.802 | 2.392 |
| 435 | 0.149 | −0.029 | −0.029 | −0.029 | 0.090 | −0.029 | −0.029 | 0.119 | −0.029 | 1.053 | −0.029 |
| 515 | 0.000 | 0.000 | 0.000 | 0.000 | 0.000 | 0.000 | 0.000 | 0.000 | 0.000 | 0.000 | 0.000 |
| 615 | 0.000 | 0.000 | 0.000 | 0.000 | 0.000 | 0.000 | 0.000 | 0.000 | 0.000 | 0.000 | 0.000 |
| 735 | 0.000 | 0.000 | 0.000 | 0.000 | 0.000 | 0.000 | 0.000 | 0.000 | 0.000 | 0.000 | 0.000 |
| 875 | 0.000 | 0.000 | 0.000 | 0.000 | 0.000 | 0.000 | 0.000 | 0.000 | 0.000 | 0.000 | 0.000 |
| Large $D_{mean}$ (μm) | 141 | 141 | 141 | 141 | 122 | 122 | 122 | 122 | 122 | 182 | 165 |
| Milled $D_{mean}$ (μm) | 29 | 29 | 29 | 29 | 34 | 34 | 34 | 34 | 34 | 36 | 36 |

TABLE 20

Particle Size Distribution of Lot C0666001 SAHA capsules prepared using 30% wet-milled and 70% large crystals % Volume SAHA 100 mg Lot # C0666001

| Particle Size (μm) | Capsule, Drum 1A, cap4 | Capsule, Drum 1B, cap3 | Capsule, Drum 2B, cap1 | Capsule, Drum 3A, cap4 | Capsule, Drum 3B, cap1 | Capsule, Drum 4A, cap4 | Capsule, Drum 4B, cap4 | Capsule, Drum 5B, cap3 |
|---|---|---|---|---|---|---|---|---|
| 5 | 5.91 | 6.03 | 5.57 | 5.48 | 5.56 | 5.49 | 5.81 | 5.99 |
| 6 | 1.31 | 1.33 | 1.22 | 1.20 | 1.23 | 1.18 | 1.25 | 1.30 |
| 7 | 1.25 | 1.26 | 1.16 | 1.14 | 1.17 | 1.12 | 1.18 | 1.23 |
| 8 | 1.20 | 1.21 | 1.10 | 1.09 | 1.13 | 1.06 | 1.12 | 1.17 |
| 9 | 1.71 | 1.72 | 1.56 | 1.55 | 1.61 | 1.50 | 1.57 | 1.66 |
| 11 | 2.15 | 2.16 | 1.95 | 1.95 | 2.03 | 1.88 | 1.95 | 2.08 |
| 13 | 2.03 | 2.04 | 1.84 | 1.84 | 1.93 | 1.78 | 1.83 | 1.96 |
| 16 | 2.42 | 2.43 | 2.20 | 2.20 | 2.30 | 2.13 | 2.19 | 2.33 |
| 19 | 2.78 | 2.80 | 2.54 | 2.54 | 2.66 | 2.48 | 2.54 | 2.69 |
| 22 | 2.69 | 2.71 | 2.49 | 2.48 | 2.59 | 2.44 | 2.50 | 2.61 |
| 25 | 3.06 | 3.09 | 2.86 | 2.85 | 2.97 | 2.82 | 2.89 | 2.99 |
| 30 | 4.25 | 4.31 | 4.03 | 4.03 | 4.17 | 4.01 | 4.08 | 4.19 |
| 38 | 6.13 | 6.22 | 5.85 | 5.92 | 6.08 | 5.88 | 5.95 | 6.07 |

TABLE 20-continued

Particle Size Distribution of Lot C0666001 SAHA capsules prepared using 30% wet-milled and 70% large crystals % Volume
SAHA 100 mg Lot # C0666001

| Particle Size (μm) | Capsule, Drum 1A, cap4 | Capsule, Drum 1B, cap3 | Capsule, Drum 2B, cap1 | Capsule, Drum 3A, cap4 | Capsule, Drum 3B, cap1 | Capsule, Drum 4A, cap4 | Capsule, Drum 4B, cap4 | Capsule, Drum 5B, cap3 |
|---|---|---|---|---|---|---|---|---|
| 45 | 5.75 | 5.83 | 5.51 | 5.61 | 5.72 | 5.56 | 5.60 | 5.70 |
| 53 | 5.29 | 5.36 | 5.08 | 5.20 | 5.29 | 5.14 | 5.17 | 5.25 |
| 63 | 6.31 | 6.39 | 6.08 | 6.24 | 6.34 | 6.17 | 6.20 | 6.28 |
| 75 | 6.84 | 6.92 | 6.62 | 6.83 | 6.92 | 6.75 | 6.77 | 6.84 |
| 90 | 7.10 | 7.13 | 6.92 | 7.19 | 7.23 | 7.11 | 7.11 | 7.13 |
| 105 | 6.16 | 6.14 | 6.07 | 6.36 | 6.32 | 6.30 | 6.28 | 6.20 |
| 125 | 6.89 | 6.80 | 6.88 | 7.30 | 7.13 | 7.26 | 7.17 | 6.95 |
| 150 | 6.59 | 6.44 | 6.71 | 7.22 | 6.90 | 7.23 | 7.03 | 6.65 |
| 180 | 5.32 | 5.15 | 5.52 | 6.02 | 5.66 | 6.10 | 5.81 | 5.36 |
| 215 | 3.56 | 3.42 | 3.79 | 4.13 | 3.85 | 4.28 | 3.98 | 3.60 |
| 255 | 1.97 | 1.87 | 2.21 | 2.34 | 2.10 | 2.48 | 2.27 | 2.03 |
| 305 | 0.96 | 0.89 | 1.25 | 1.28 | 0.89 | 1.28 | 1.19 | 1.07 |
| 365 | 0.38 | 0.34 | 0.72 | 0.00 | 0.23 | 0.57 | 0.55 | 0.46 |
| 435 | 0.00 | 0.00 | 0.58 | 0.00 | 0.00 | 0.00 | 0.00 | 0.19 |
| 515 | 0.00 | 0.00 | 0.63 | 0.00 | 0.00 | 0.00 | 0.00 | 0.00 |
| 615 | 0.00 | 0.00 | 0.66 | 0.00 | 0.00 | 0.00 | 0.00 | 0.00 |
| 735 | 0.00 | 0.00 | 0.39 | 0.00 | 0.00 | 0.00 | 0.00 | 0.00 |
| 875 | 0.00 | 0.00 | 0.00 | 0.00 | 0.00 | 0.00 | 0.00 | 0.00 |

TABLE 21

Particle Size Distribution of Lot C0667001 SAHA capsules prepared using 30% wet-milled and 70% large crystals % Volume
SAHA 100 mg Lot # C0667001

| Particle Size (μm) | capsule L10C4 | capsule L1C4 | capsule L1C3 | capsule L2C3 | capsule L9C4 | capsule L5C3 | capsule L10C2 | capsule L5C1 |
|---|---|---|---|---|---|---|---|---|
| 5 | 5.57 | 5.46 | 5.08 | 4.86 | 4.44 | 4.07 | 3.78 | 4.09 |
| 6 | 1.21 | 1.20 | 1.12 | 1.04 | 0.97 | 0.90 | 0.86 | 0.91 |
| 7 | 1.15 | 1.14 | 1.06 | 0.98 | 0.92 | 0.86 | 0.83 | 0.87 |
| 8 | 1.10 | 1.09 | 1.01 | 0.93 | 0.87 | 0.83 | 0.80 | 0.83 |
| 9 | 1.57 | 1.55 | 1.44 | 1.32 | 1.25 | 1.19 | 1.17 | 1.20 |
| 11 | 1.98 | 1.96 | 1.83 | 1.66 | 1.58 | 1.53 | 1.52 | 1.53 |
| 13 | 1.91 | 1.89 | 1.76 | 1.61 | 1.54 | 1.50 | 1.49 | 1.50 |
| 16 | 2.33 | 2.31 | 2.17 | 2.00 | 1.92 | 1.87 | 1.87 | 1.86 |
| 19 | 2.77 | 2.74 | 2.59 | 2.43 | 2.33 | 2.27 | 2.27 | 2.26 |
| 22 | 2.77 | 2.75 | 2.62 | 2.49 | 2.39 | 2.33 | 2.32 | 2.31 |
| 25 | 3.24 | 3.20 | 3.08 | 2.98 | 2.86 | 2.78 | 2.76 | 2.75 |
| 30 | 4.62 | 4.54 | 4.40 | 4.32 | 4.16 | 4.05 | 4.00 | 3.99 |
| 38 | 6.76 | 6.58 | 6.44 | 6.44 | 6.21 | 6.07 | 5.99 | 5.97 |
| 45 | 6.35 | 6.16 | 6.07 | 6.16 | 5.97 | 5.86 | 5.76 | 5.77 |
| 53 | 5.86 | 5.67 | 5.62 | 5.77 | 5.62 | 5.54 | 5.43 | 5.44 |
| 63 | 7.03 | 6.79 | 6.75 | 7.03 | 6.88 | 6.82 | 6.69 | 6.68 |
| 75 | 7.68 | 7.41 | 7.41 | 7.79 | 7.72 | 7.69 | 7.58 | 7.51 |
| 90 | 7.93 | 7.66 | 7.73 | 8.17 | 8.27 | 8.28 | 8.22 | 8.07 |
| 105 | 6.72 | 6.51 | 6.63 | 7.02 | 7.31 | 7.36 | 7.37 | 7.16 |
| 125 | 7.17 | 7.00 | 7.18 | 7.62 | 8.19 | 8.29 | 8.38 | 8.05 |
| 150 | 6.29 | 6.24 | 6.42 | 6.87 | 7.58 | 7.79 | 7.96 | 7.57 |
| 180 | 4.40 | 4.57 | 4.64 | 5.07 | 5.61 | 5.96 | 6.19 | 5.85 |
| 215 | 2.35 | 2.77 | 2.74 | 3.05 | 3.24 | 3.61 | 3.87 | 3.73 |
| 255 | 0.92 | 1.47 | 1.45 | 1.51 | 1.48 | 1.72 | 1.92 | 2.09 |
| 305 | 0.32 | 0.83 | 0.88 | 0.65 | 0.68 | 0.66 | 0.76 | 1.19 |
| 365 | 0.00 | 0.51 | 0.67 | 0.19 | 0.00 | 0.19 | 0.22 | 0.60 |
| 435 | 0.00 | 0.00 | 0.67 | 0.05 | 0.00 | 0.00 | 0.00 | 0.24 |
| 515 | 0.00 | 0.00 | 0.53 | 0.00 | 0.00 | 0.00 | 0.00 | 0.00 |
| 615 | 0.00 | 0.00 | 0.00 | 0.00 | 0.00 | 0.00 | 0.00 | 0.00 |
| 735 | 0.00 | 0.00 | 0.00 | 0.00 | 0.00 | 0.00 | 0.00 | 0.00 |
| 875 | 0.00 | 0.00 | 0.00 | 0.00 | 0.00 | 0.00 | 0.00 | 0.00 |

Example 17

Patient Studies

This Phase I study conducted in advanced stage cancer patients assessed safety and tolerability of oral vorinostat administered 400 mg q.d., single- and multiple-dose serum pharmacokinetics (PK) of vorinostat, and the effect of a standard high-fat meal on single-dose vorinostat PK. Patients received a single-dose of 400 mg vorinostat on Day 1 (fasted) and Day 5 (after a standard high-fat meal) with 48 hours of postdose PK sampling on both days. Patients then received 400 mg vorinostat once a day on Days 7 through 28 (22 days of dosing). On Day 28, vorinostat was administered after a standard high-fat meal with PK sampling for 24 hrs postdose. Of 23 patients enrolled, 23 were evaluable for Day 1 PK, 20 for Day 5 PK, and 14 for Day 28 PK. The apparent $t_{1/2}$ of vorinostat was short. A high-fat meal was associated with a small increase in the extent of absorption and a modest decrease in the rate of absorption of vorinostat. A lag time of at least 15 minutes was observed before detectable levels of vorinostat were observed in serum in the fed state in most subjects, and $T_{max}$ was delayed. Following multiple-dose administration of vorinostat, serum concentration time profiles were similar to those of single-dose administration. Trough concentrations following multiple-dose administration were generally below the limit of quantification, which is consistent with the short apparent terminal $t_{1/2}$. In conclusion, short-term administration of vorinostat to patients with advanced cancer was generally well tolerated. Vorinostat exhibited a short $t_{1/2}$, serum concentration time profiles that were similar between single-dose and multiple-dose administration, and a slightly decreased rate of absorption when administrated with a high-fat meal.

TABLE 22

PK Parameters of Vorinostat Following Single and Multiple Doses of Vorinostat 400 mg Daily

| Dose | Single Dose | Single Dose | Multiple Doses* | GMR[†] | p-Value |
|---|---|---|---|---|---|
| Diet | Fasted | Fed | Fed | — | — |
| N | 23 | 20 | 14 | — | — |
| $AUC_{0-\infty}$, μM · hr[‡] | 3.87 | 5.33 | — | 1.38[§] | <0.001[§] |
| (Range) | (2.33-9.86) | (3.41-9.34) | (4.00-10.36) | — | — |
| $AUC_{0-24\,hr}$, μM · hr[‡] | 3.82 | 5.33 | 6.46 | 1.21[∥]; 1.23[¶] | 0.019[∥]; 0.010[¶] |
| $C_{max}$, μM[‡] | 1.12 | 1.02 | 1.13 | 0.91[§] | 0.451[§] |
| $T_{max}$, hr[#] | 1.50 | 4.00 | 4.21 | — | <0.001[§]; 0.869** |
| $t_{1/2}$, hr[††] | 1.74 | 1.44 | 1.34 | — | 0.036[§] |
| $f_e$[‡‡] | 0.0021 | 0.0030 | 0.0037 | — | — | fe = Fraction of dose excreted unchanged in urine.
*Once daily for 22 days.
[†]Geometric mean ratio.
[‡]Geometric mean.
[§]Single dose fed/single dose fasted.
[∥]Accumulation ratio: $AUC_{0-24\,hr}$ multiple dose fed/$AUC_{0-24\,hr}$ single dose fed.
[¶]Linearity ratio: $AUC_{0-24\,hr}$ multiple dose fed/$AUC_{0-\infty}$ single dose fed.
[#]Median.
**Multiple dose fed/single dose fed.
[††]Harmonic mean.
[‡‡]Arithmetic mean (single dose fasted n = 22, single dose fed n = 21, multiple dose fed n = 12).

While this invention has been particularly shown and described with references to embodiments thereof, it will be understood by those skilled in the art that various changes in form and details may be made therein without departing from the meaning of the invention described. Rather, the scope of the invention is defined by the claims that follow:

REFERENCES

1. Sporn, M. B., Roberts, A. B., and Driscoll, J. S. (1985) in Cancer: Principles and Practice of Oncology, eds. Hellman, S., Rosenberg, S. A., and DeVita, V. T., Jr., Ed. 2, (J. B. Lippincott, Philadelphia), P. 49.
2. Breitman, T. R., Selonick, S. E., and Collins, S. J. (1980) Proc. Natl. Acad. Sci. USA 77: 2936-2940.
3. Olsson, I. L. and Breitman, T. R. (1982) Cancer Res. 42: 3924-3927.
4. Schwartz, E. L. and Sartorelli, A. C. (1982) Cancer Res. 42: 2651-2655.
5. Marks, P. A., Sheffery, M., and Rifkind, R. A. (1987) Cancer Res. 47: 659.
6. Sachs, L. (1978) Nature (Lond.) 274: 535.
7. Friend, C., Scher, W., Holland, J. W., and Sato, T. (1971) Proc. Natl. Acad. Sci. (USA) 68: 378-382.
8. Tanaka, M., Levy, J., Terada, M., Breslow, R., Rifkind, R. A., and Marks, P. A. (1975) Proc. Natl. Acad. Sci. (USA) 72: 1003-1006.
9. Reuben, R. C., Wife, R. L., Breslow, R., Rifkind, R. A., and Marks, P. A. (1976) Proc. Natl. Acad. Sci. (USA) 73: 862-866.
10. Abe, E., Miyaura, C., Sakagami, H., Takeda, M., Konno, K., Yamazaki, T., Yoshika, S., and Suda, T. (1981) Proc. Natl, Acad, Sci. (USA) 78: 4990-4994.
11. Schwartz, E. L., Snoddy, J. R., Kreutter, D., Rasmussen, H., and Sartorelli, A. C. (1983) Proc. Am. Assoc. Cancer Res. 24: 18.
12. Tanenaga, K., Hozumi, M., and Sakagami, Y. (1980) Cancer Res. 40: 914-919.
13. Lotem, J. and Sachs, L. (1975) Int. J. Cancer 15: 731-740.
14. Metcalf, D. (1985) Science, 229: 16-22.
15. Scher, W., Scher, B. M., and Waxman, S. (1983) Exp. Hematol. 11: 490-498.
16. Scher, W., Scher, B. M., and Waxman, S. (1982) Biochem. & Biophys. Res. Comm. 109: 348-354.
17. Huberman, E. and Callaham, M. F. (1979) Proc. Natl. Acad. Sci. (USA) 76: 1293-1297.

18. Lottem, J. and Sachs, L. (1979) Proc. Natl. Acad. Sci. (USA) 76: 5158-5162.
19. Terada, M., Epner, E., Nudel, U., Salmon, J., Fibach, E., Rifkind, R. A., and Marks, P. A. (1978) Proc. Natl. Acad. Sci. (USA) 75: 2795-2799.
20. Morin, M. J. and Sartorelli, A. C. (1984) Cancer Res. 44: 2807-2812.
21. Schwartz, E. L., Brown, B. J., Nierenberg, M., Marsh, J. C., and Sartorelli, A. C. (1983) Cancer Res. 43: 2725-2730.
22. Sugano, H., Furusawa, M., Kawaguchi, T., and Ikawa, Y. (1973) Bibl. Hematol. 39: 943-954.
23. Ebert, P. S., Wars, I., and Buell, D. N. (1976) Cancer Res. 36: 1809-1813.
24. Hayashi, M., Okabe, J., and Hozumi, M. (1979) Gann 70: 235-238.
25. Richon, V. M., Webb, Y., Merger, R., et al. (1996) PNAS 93:5705-8.
26. Cohen, L. A., Amin, S., Marks, P. A., Rifkind, R. A., Desai, D., and Richon, V. M. (1999) Anticancer Research 19:4999-5006.
27. Grunstein, M. (1997) Nature 389:349-52.
28. Finnin, M. S., Donigian, J. R., Cohen, A., et al. (1999) Nature 401:188-193.
29. Van Lint, C., Emiliani, S., Verdin, E. (1996) Gene Expression 5:245-53.
30. Archer, S. Shufen, M. Shei, A., Hodin, R. (1998) PNAS 95:6791-96.
31. Dressel, U., Renkawitz, R., Baniahmad, A. (2000) Anticancer Research 20(2A):1017-22.
32. Parker, Vigoroux, Reed, AIChE J. (2000) pp. 1290-99.
33. Nunez, Espiell, Chem. Eng. Sci. (1986) pp. 2075-83.
34. O. Levenspiel: Chemical Reaction Engineering, 2nd Ed., p. 373.
35. M. Vanni: J. of Colloid and Interface Sci. (2000) pp. 143-160.
36. P. J. Hill and K. M. Ng, AIChE J. (1995) pp. 1204-1216.

What is claimed is:

1. A pharmaceutical composition for oral administration comprising about 100 mg suberoylanilide hydroxamic acid or a pharmaceutically acceptable salt or hydrate thereof as an active ingredient in solid form, wherein the entire active ingredient has an in vitro dissolution profile with a similarity factor (f2) of at least 56 to 100 compared to the reference dissolution profile of 52.7% dissolved at 10 minutes, 61.7% dissolved at 15 minutes, 67.7% dissolved at 20 minutes, 75.5% dissolved at 30 minutes, 82.6% dissolved at 45 minutes, and 87.0% dissolved at 60 minutes in vitro, and optionally a pharmaceutically acceptable excipient, wherein the dissolution profile is measured using a USP Dissolution Apparatus II with a helical sinker in 900 mL of 2.0% Tween at a temperature of 37±0.5° C., and paddles rotated at 100 rpm.

2. The pharmaceutical composition of claim 1 that is formulated as a powder in a single capsule or tablet, wherein the amount of the active ingredient is about 100 mg of suberoylanilide hydroxamic acid; or that is formulated as a powder in two capsules or tablets, wherein the amount of active ingredient in each capsule or tablet is about 50 mg of suberoylanilide hydroxamic acid.

3. The pharmaceutical composition of claim 1, wherein f2 is 60 to 100.

4. The pharmaceutical composition of claim 3 that is formulated as a powder in a single capsule or tablet, wherein the amount of the active ingredient is about 100 mg of suberoylanilide hydroxamic acid; or that is formulated as a powder in two capsules or two tablets, wherein the amount of active ingredient in each capsule or tablet is about 50 mg of suberoylanilide hydroxamic acid.

5. The pharmaceutical composition of claim 3, that is formulated as a powder blend of the active ingredient with or without the excipient in capsule form.

6. The pharmaceutical composition of claim 5, wherein the active ingredient is crystalline suberoylanilide hydroxamic acid.

7. The pharmaceutical composition of claim 5, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

8. The pharmaceutical composition of claim 5, wherein the active ingredient is crystalline suberoylanilide hydroxamic acid with unit cell parameters of a=10.9 Å, b=7.9 Å, c=16.4 Å, α=90°, β=97.8°, γ=90°, space group $P2_1/n$.

9. The pharmaceutical composition of claim 1, wherein f2 is 65 to 100.

10. The pharmaceutical composition of claim 9 that is formulated as a powder in two capsules or tablets, wherein the amount of active ingredient in each capsule or tablet is about 50 mg of suberoylanilide hydroxamic acid; or that is formulated as a powder in a single capsule or tablet, wherein the amount of the active ingredient is about 100 mg of suberoylanilide hydroxamic acid.

11. The pharmaceutical composition of claim 9, that is formulated as a powder blend of the active ingredient with or without the excipient in capsule form.

12. The pharmaceutical composition of claim 11, wherein the active ingredient is crystalline suberoylanilide hydroxamic acid.

13. The pharmaceutical composition of claim 11, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

14. The pharmaceutical composition of claim 11, wherein the active ingredient is crystalline suberoylanilide hydroxamic acid with unit cell parameters of a=10.9 Å, b=7.9 Å, c=16.4 Å, α=90°, β=97.8°, γ=90°, space group $P2_1/n$.

15. The pharmaceutical composition of claim 1, wherein the active ingredient is crystalline suberoylanilide hydroxamic acid of Form I.

16. The pharmaceutical composition of claim 1, wherein f2 is 70 to 100.

17. The pharmaceutical composition of claim 16 that is formulated as a powder in two capsules or tablets, wherein the amount of active ingredient in each capsule or tablet is about 50 mg of suberoylanilide hydroxamic acid; or that is formulated as a powder in a single capsule or tablet, wherein the amount of the active ingredient is about 100 mg of suberoylanilide hydroxamic acid.

18. The pharmaceutical composition of claim 16, wherein the active ingredient is crystalline suberoylanilide hydroxamic acid of Form I.

19. The pharmaceutical composition of claim 16, that is formulated as a powder blend of the active ingredient with or without the excipient in capsule form.

20. The pharmaceutical composition of claim 19, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ, and lacking peaks at 13.4-14.0 and 22.7-23.0 degrees 2θ using a Copper X-ray source.

21. The pharmaceutical composition of claim 19, wherein the active ingredient is crystalline suberoylanilide hydroxamic acid.

22. The pharmaceutical composition of claim 19, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

23. The pharmaceutical composition of claim 19, wherein the active ingredient is crystalline suberoylanilide hydroxamic acid with unit cell parameters of a=10.9 Å, b=7.9 Å, c=16.4 Å, α=90°, β=97.8°, γ=90°, space group P2$_1$/n.

24. The pharmaceutical composition of claim 1, that is formulated as a powder blend of the active ingredient with or without the excipient in capsule form.

25. The pharmaceutical composition of claim 24, wherein the active ingredient is crystalline suberoylanilide hydroxamic acid.

26. The pharmaceutical composition of claim 24, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

27. The pharmaceutical composition of claim 26 obtained by the process of:
(a) blending 40-20% of a first batch of crystalline suberoylanilide hydroxamic acid having a mean particle size of 25 to 45 µm and 60-80% of a second batch of crystalline suberoylanilide hydroxamic acid having a mean particle size of 130-180 µm; and
(b) encapsulating a portion of the blended crystalline suberoylanilide hydroxamic acid to produce the pharmaceutical composition.

28. The pharmaceutical composition of claim 27, wherein step (a) comprises the step of:
blending 30% of a first batch of crystalline suberoylanilide hydroxamic acid having a mean particle size of 25 to 45 µm and 70% of a second batch of crystalline suberoylanilide hydroxamic acid having a mean particle size of 130-180 µm.

29. The pharmaceutical composition of claim 24, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ, and lacking peaks at 13.4-14.0 and 22.7-23.0 degrees 2θ using a Copper X-ray source.

30. The pharmaceutical composition of claim 24, wherein the active ingredient is crystalline suberoylanilide hydroxamic acid with unit cell parameters of a=10.9 Å, b=7.9 Å, c=16.4 Å, α=90°, β=97.8°, γ=90°, space group P2$_1$/n.

31. The pharmaceutical composition of claim 24 obtained by the process of:
(a) blending about 60-5% of a first batch of crystalline suberoylanilide hydroxamic acid having a mean particle size of less than about 60 µm and about 40-95% of a second batch of crystalline suberoylanilide hydroxamic acid having a mean particle size of about 100-250 µm; and
(b) encapsulating a portion of the blended crystalline suberoylanilide hydroxamic acid to produce the pharmaceutical composition.

32. The pharmaceutical composition of claim 24 or 11, wherein the % volume of active ingredient with particle size less than about 105 microns is about 45-85% and the % volume of active ingredient with particle size more than about 105 microns is about 55-15%.

33. The pharmaceutical composition of claim 24 or 11, wherein the % volume of active ingredient with particle sizes from about 120 to about 250 microns is in the range of about 4.0% to about 12%, and the % volume of active ingredient with particle sizes from about 35 to about 40 microns is in the range of about 3.0% to about 7%.

34. A single pharmaceutical oral dosage unit form comprising about 120 mg to about 600 mg of suberoylanilide hydroxamic acid or a pharmaceutically acceptable salt or hydrate thereof as an active ingredient in solid form, wherein a portion of said dosage unit form comprising about 100 mg of the active ingredient has an in vitro dissolution profile with a similarity factor (f2) of at least 56 to 100 compared to the reference dissolution profile of 52.7% dissolved at 10 minutes, 61.7% dissolved at 15 minutes, 67.7% dissolved at 20 minutes, 75.5% dissolved at 30 minutes, 82.6% dissolved at 45 minutes, and 87.0% dissolved at 60 minutes in vitro, and optionally a pharmaceutically acceptable excipient, wherein the dissolution profile is measured using a USP Dissolution Apparatus II with a helical sinker in 900 mL of 2.0% Tween at a temperature of 37±0.5° C., and paddles rotated at 100 rpm.

35. The single pharmaceutical oral dosage unit form of claim 34, wherein a portion of said dosage unit form comprising about 100 mg of the active ingredient has an in vitro dissolution profile with a similarity factor (f2) of at least 70 to 100 compared to the reference dissolution profile.

36. The single pharmaceutical oral dosage unit form of claim 35, wherein the active ingredient is crystalline suberoylanilide hydroxamic acid of Form I.

37. The single pharmaceutical oral dosage unit form of claim 35, that is formulated as a powder blend of the active ingredient with or without the excipient in capsule form.

38. The single pharmaceutical oral dosage unit form of claim 37, wherein the active ingredient is crystalline suberoylanilide hydroxamic acid.

39. The single pharmaceutical oral dosage unit form of claim 37, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

40. The single pharmaceutical oral dosage unit form of claim 37, wherein the active ingredient is crystalline suberoylanilide hydroxamic acid with unit cell parameters of a=10.9 Å, b=7.9 Å, c=16.4 Å, α=90°, β=97.8°, γ=90°, space group P2$_1$/n.

41. The single pharmaceutical oral dosage unit form of claim 35 that is formulated as a powder in a single capsule or tablet, wherein the amount of active ingredient in the capsule or tablet is about 200 mg of suberoylanilide hydroxamic acid.

42. The single pharmaceutical oral dosage unit form of claim 34, wherein a portion of said dosage unit form comprising about 100 mg of the active ingredient has an in vitro dissolution profile with a similarity factor (f2) of at least 60 to 100 compared to the reference dissolution profile.

43. The single pharmaceutical oral dosage unit form of claim 42, that is formulated as a powder blend of the active ingredient with or without the excipient in capsule form.

44. The single pharmaceutical oral dosage unit form of claim 43, wherein the active ingredient is crystalline suberoylanilide hydroxamic acid.

45. The single pharmaceutical oral dosage unit form of claim 43, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

46. The single pharmaceutical oral dosage unit form of claim 43, wherein the active ingredient is crystalline suberoylanilide hydroxamic acid with unit cell parameters of a=10.9 Å, b=7.9 Å, c=16.4 Å, α=90°, β=97.8°, γ=90°, space group $P2_1/n$.

47. The single pharmaceutical oral dosage unit form of claim 42 that is formulated as a powder in a single capsule or tablet, wherein the amount of active ingredient in the capsule or tablet is about 200 mg of suberoylanilide hydroxamic acid.

48. The single pharmaceutical oral dosage unit form of claim 34, wherein a portion of said dosage unit form comprising about 100 mg of the active ingredient has an in vitro dissolution profile with a similarity factor (f2) of at least 65 to 100 compared to the reference dissolution profile.

49. The single pharmaceutical oral dosage unit form of claim 48, that is formulated as a powder blend of the active ingredient with or without the excipient in capsule form.

50. The single pharmaceutical oral dosage unit form of claim 49, wherein the active ingredient is crystalline suberoylanilide hydroxamic acid.

51. The single pharmaceutical oral dosage unit form of claim 49, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

52. The single pharmaceutical oral dosage unit form of claim 49, wherein the active ingredient is crystalline suberoylanilide hydroxamic acid with unit cell parameters of a=10.9 Å, b=7.9 Å, c=16.4 Å, α=90°, β=97.8°, γ=90°, space group $P2_1/n$.

53. The single pharmaceutical oral dosage unit form of claim 48 that is formulated as a powder in a single capsule or tablet, wherein the amount of active ingredient in the capsule or tablet is about 200 mg of suberoylanilide hydroxamic acid.

54. The single pharmaceutical oral dosage unit form of claim 34, that is formulated as a powder blend of the active ingredient with or without the excipient in capsule form.

55. The single pharmaceutical oral dosage unit form of claim 54, wherein the active ingredient is crystalline suberoylanilide hydroxamic acid.

56. The single pharmaceutical oral dosage unit form of claim 54, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ using a Copper X-ray source.

57. The single pharmaceutical oral dosage unit form of claim 54, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ, and lacking peaks at 13.4-14.0 and 22.7-23.0 degrees 2θ using a Copper X-ray source.

58. The single pharmaceutical oral dosage unit form of claim 37, wherein the active ingredient is crystalline suberoylanilide hydroxamic acid and characterized by an X-ray diffraction pattern comprising characteristic peaks at 9.4, 17.5, 19.4, 20.0, 24.0 and 28.0 degrees 2θ, and lacking peaks at 13.4-14.0 and 22.7-23.0 degrees 2θ using a Copper X-ray source.

59. The single pharmaceutical oral dosage unit form of claim 54, wherein the active ingredient is crystalline suberoylanilide hydroxamic acid with unit cell parameters of a=10.9 Å, b=7.9 Å, c=16.4 Å, α=90°, β=97.8°, γ=90°, space group $P2_1/n$.

60. The single pharmaceutical oral dosage unit of claim 56 obtained by the process of:
(a) blending 40-20% of a first batch of crystalline suberoylanilide hydroxamic acid having a mean particle size of 25 to 45 μm and 60-80% of a second batch of crystalline suberoylanilide hydroxamic acid having a mean particle size of 130-180 μm; and
(b) encapsulating a portion of the blended crystalline suberoylanilide hydroxamic acid to produce the single pharmaceutical oral dosage unit.

61. The single pharmaceutical oral dosage unit of claim 60, wherein step (a) comprises the step of:
blending 30% of a first batch of crystalline suberoylanilide hydroxamic acid having a mean particle size of 25 to 45 μm and 70% of a second batch of crystalline suberoylanilide hydroxamic acid having a mean particle size of 130-180 μm.

62. The single pharmaceutical oral dosage unit of claim 54 obtained by the process of:
(a) blending about 60-5% of a first batch of crystalline suberoylanilide hydroxamic acid having a mean particle size of less than about 60 μm and about 40-95% of a second batch of crystalline suberoylanilide hydroxamic acid having a mean particle size of about 100-250 μm; and
(b) encapsulating a portion of the blended crystalline suberoylanilide hydroxamic acid to produce the single pharmaceutical oral dosage unit.

63. The single pharmaceutical oral dosage unit form of claim 54 or 37, wherein the % volume of active ingredient with particle sizes from about 120 to about 250 microns is in the range of about 4.0% to about 12%, and the % volume of active ingredient with particle sizes from about 35 to about 40 microns is in the range of about 3.0% to about 7%.

64. The single pharmaceutical oral dosage unit form of claim 54 or 37, wherein the % volume of active ingredient with particle size less than about 105 microns is about 45-85% and the % volume of active ingredient with particle size more than about 105 microns is about 55-15%.

65. The single pharmaceutical oral dosage unit form of claim 34, wherein the active ingredient is crystalline suberoylanilide hydroxamic acid of Form I.

66. The single pharmaceutical oral dosage unit form of claim 34 that is formulated as a powder in a single capsule or tablet, wherein the amount of active ingredient in the capsule or tablet is about 200 mg of suberoylanilide hydroxamic acid.

67. A pharmaceutical composition for oral administration comprising about 100 mg of suberoylanilide hydroxamic acid or a pharmaceutically acceptable salt or hydrate thereof as an active ingredient in solid form, wherein the entire active ingredient has an in vitro dissolution profile of:
46-60% dissolved at 10 minutes, 55-69% dissolved at 15 minutes, 61-75% dissolved at 20 minutes, 69-83% dissolved at 30 minutes, 76-90% dissolved at 45 minutes, and 80-94% dissolved at 60 minutes in vitro, and optionally a pharmaceutically acceptable excipient, wherein the dissolution profile is measured using a USP Dissolution Apparatus II with a helical sinker in 900 mL of 2.0% Tween at a temperature of 37±0.5° C., and paddles rotated at 100 rpm.

68. A single pharmaceutical oral dosage unit form comprising about 120 mg to about 600 mg of suberoylanilide hydroxamic acid or a pharmaceutically acceptable salt or hydrate thereof as an active ingredient in solid form, wherein a portion of said dosage unit form comprising about 100 mg of the active ingredient has an in vitro dissolution profile of: 46-60% dissolved at 10 minutes, 55-69% dissolved at 15 minutes, 61-75% dissolved at 20 minutes, 69-83% dissolved at 30 minutes, 76-90% dissolved at 45 minutes, and 80-94% dissolved at 60 minutes in vitro, and optionally a pharmaceutically acceptable excipient, wherein the dissolution profile is measured using a USP Dissolution Apparatus II with a helical sinker in 900 mL of 2.0% Tween at a temperature of 37±0.5° C., and paddles rotated at 100 rpm.

* * * * *